United States Patent
Higashi et al.

(10) Patent No.: US 8,470,054 B2
(45) Date of Patent: Jun. 25, 2013

(54) AZO COMPOUND, AZO PIGMENT, PIGMENT DISPERSION, COLORING COMPOSITION, COLOR FILTER, INK FOR INKJET RECORDING, AND PRINTING INK

(75) Inventors: Masahiro Higashi, Shizuoka (JP); Yoshihiro Jimbo, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/571,125

(22) Filed: Aug. 9, 2012

(65) Prior Publication Data

US 2013/0036938 A1    Feb. 14, 2013

(30) Foreign Application Priority Data

Aug. 11, 2011    (JP) .................. 2011-176390

(51) Int. Cl.
*C09B 67/22*    (2006.01)
*C09D 11/02*    (2006.01)

(52) U.S. Cl.
USPC ............ 8/637.1; 8/639; 8/690; 106/31.8

(58) Field of Classification Search
USPC ............ 8/637.1, 639, 690; 106/31.8
See application file for complete search history.

(56) References Cited

U.S. PATENT DOCUMENTS

2006/0229439 A1* 10/2006 Ueno ..................... 534/573
2011/0143270 A1    6/2011 Seto et al.

FOREIGN PATENT DOCUMENTS

| JP | 01-152449 A | 6/1989 |
| JP | 05-005067 A | 1/1993 |
| JP | 6-75375 A | 3/1994 |

(Continued)

OTHER PUBLICATIONS

STIC Search Report dated Nov. 13, 2012.*

*Primary Examiner* — Eisa Elhilo
(74) *Attorney, Agent, or Firm* — Sughrue Mion, PLLC

(57) ABSTRACT

Provided are an azo compound represented by the following formula (1), a tautomer thereof, and a salt or hydrate of the azo compound or the tautomer:

wherein in the formula (1),
A represents a heterocyclic group; G represents a hydrogen atom, an aliphatic group, an aromatic group, or a heterocyclic group; $R_1$ and $R_2$ each independently represent a group represented by the following formula (2) or (3):

24 Claims, 6 Drawing Sheets

| FOREIGN PATENT DOCUMENTS | | |
|---|---|---|
| JP | 2592271 B2 | 3/1997 |
| JP | 9-511278 A | 11/1997 |
| JP | 2004-123866 A | 4/2004 |
| JP | 3894726 B2 | 3/2007 |
| JP | 2008-007732 A | 1/2008 |
| JP | 2008-013472 A | 1/2008 |
| WO | 00/23525 A1 | 4/2000 |
| WO | 2005/052074 A1 | 6/2005 |

* cited by examiner

AZO COMPOUND, AZO PIGMENT, PIGMENT DISPERSION, COLORING COMPOSITION, COLOR FILTER, INK FOR INKJET RECORDING, AND PRINTING INK

BACKGROUND OF THE INVENTION

1. Field of the Invention

The present invention relates to an azo compound, an azo pigment, a pigment dispersion, a coloring composition, a coloring composition for color filters, a color filter, a method for preparing a coloring composition for color filters, an ink for inkjet recording, a printing ink, a coating material, a dye, and a resist ink.

2. Description of the Related Art

In recent years, materials for forming color images in particular are the mainstream image recording materials, and specifically, recording materials for an inkjet system, recording materials for a thermosensitive transfer system, recording materials for an electrophotographic system, transfer-type silver halide photosensitive materials, printing inks, recording pens, and the like are in active use. Furthermore, color filters are used to record and reproduce color images in image pickup elements such as a charge-coupled device (CCD) among imaging apparatuses, and in liquid crystal displays (LCDs) or plasma display panels (PDPs) among display apparatuses. In these color image recording materials or color filters, colorants (dyes or pigments) of the three primary colors of a so-called additive color mixing method or a so-called subtractive color mixing method are used to display or record full color images. However, in the current situation, there is no colorant which has absorption characteristics capable of realizing a preferable color reproduction gamut, and also has fastness that can withstand various use conditions and environmental conditions. Thus, there is a strong demand for an improvement.

The dyes and pigments that are used in the various applications described above need to have properties such as described below in common. That is, the properties include absorption characteristics that are preferable in terms of color reproducibility, and fastness under the environmental conditions used, for example, satisfactory light fastness, satisfactory heat resistance, and satisfactory resistance to oxidative gases such as ozone. In addition, when the colorant is a pigment, the pigment needs to have properties such as that the pigment substantially is insoluble in water or organic solvents and has satisfactory chemical resistant fastness, and that preferable absorption characteristics in a molecular dispersion state are not impaired even if the pigment is used in the form of particles. The requested characteristics described above can be controlled by the intensity of the intermolecular interaction, but since the two properties are in a trade-off relationship, it is difficult to achieve a balance between the two properties.

Furthermore, in addition to that, when such a pigment is put to use, there is also a need for properties such as that the pigment has a particle size and a particle shape necessary to exhibit desired transparency, that the pigment has satisfactory fastness under the environmental conditions used, for example, satisfactory light fastness, satisfactory heat resistance, satisfactory resistance to oxidative gases such as ozone, and satisfactory chemical resistant fastness against organic solvents or sulfurous acid gas, and that the pigment is dispersed even to a state of very fine particles in the medium used and maintains a stable dispersion state. Particularly, there is a strong demand for a pigment which has satisfactory hue, has high tinctorial strength even in the presence of light, heat and humidity, and an active gas in the environment, and has fastness to light.

That is, the performance required from a pigment extends over a variety of fields as compared with dyes of which having performance as coloring molecules is demanded, and the pigment needs to satisfy not only the performance as coloring molecules, but also the performance requested as a solid (fine particle dispersion) as aggregates of coloring molecules. Consequently, the group of compounds that can be used as pigments is extremely limited as compared with dyes, and even if high performance dyes are converted to pigments, not many of the dyes can satisfy the performance required as fine particle dispersions, and such pigments cannot be easily developed. This is verified from the fact that the number of pigments registered with the Color Index does not make up even $\frac{1}{10}$ of the number of dyes.

Since azo pigments have excellent color and tinctorial strength, which are chromatic characteristics, azo pigments are widely used in printing inks, inkjet inks, electrophotographic materials, and the like. Among these, azo pigments that are most typically used include diarylide yellow pigments and naphthol red azo pigments. Examples of diarylide pigments include C.I. Pigment Yellow 12, Yellow 13, and Yellow 17. Examples of naphthol azo pigments include C.I. Pigment Red 208, and Red 242. However, since these pigments have very inferior fastness, particularly light fastness, when print materials are exposed to light, the pigments are degraded and discolorized, so that the pigments are not suitable for long-term storage of print materials.

In order to ameliorate such defects, there have been disclosed azo pigments having improved fastness by increasing the molecular weight or by introducing a group having a strong intermolecular interaction (see, for example, WO 2005/052074 A, WO 00/023525 A, and JP 2008-013472A). However, even for the improved pigments, for example, the pigment described in WO 2005/052074 A has light fastness that has been improved but is not yet sufficient, and for example, the pigments described in WO 00/023525A and JP 2008-013472A have a defect that the pigments have greenish color, low tinctorial strength, and inferior chromatic characteristics.

Furthermore, JP 1997-511278T (JP H09-511278T), JP 2008-007732A, JP 2004-123866A, and JP 3894726B disclose colorants having absorption characteristics with excellent color reproducibility and sufficient fastness. However, the specific compounds described in these patent documents either have satisfactory hues with inferior fastness, or satisfactory fastness with inferior hues. Also, the compounds easily dissolve in organic solvents or water, and do not therefore have sufficient chemical resistant fastness.

In the case of expression of full color by using a subtractive color mixing method based on three colors of yellow, magenta and cyan, or based on four colors of the three colors plus black, if a pigment of only one color having inferior fastness is used, the grey balance of the print material changes with a lapse of time. Also, if a pigment having inferior chromatic characteristics is used, color reproducibility at the time of printing is deteriorated. Therefore, in order to obtain a print material which maintains high color reproducibility for a long time period, a pigment and a pigment dispersion which can achieve a balance between chromatic characteristics and fastness are desirable.

Azo colorants have conventionally been utilized as colorants in various fields, since many of azo colorants have various visible light absorptions. For example, they have come into use in various fields such as coloration of synthetic resins, printing inks, colorants for sublimation type thermosensitive transfer materials, inks for inkjet recording, and colorants for color filters. Major performances required from azo colorants as colorants include the absorption spectrum. The hue of a colorant exerts a great influence on the tint and the tactile feeling of a body colored with the colorant, and gives a large effect on visual sensation. Therefore, studies have been conducted for a long time on the absorption spectra of colorants.

Conventionally known azo dyes containing a nitrogen-containing, 5-membered ring as an azo component are also disclosed in JP 2008-007732A. Furthermore, JP 2004-123866A, JP 3894726B, and JP 2592271B disclose naphthol-based azo pigments and dyes in which a benzene ring and a naphthalene ring are bonded through an azo group.

Furthermore, in recent years, there has been a demand for image display apparatuses to have miniaturization, thickness reduction, weight reduction, screen enlargement, definition enhancement and the like. Also, the range of applications of the image display apparatuses has expanded to displays for personal computers, television sets, game machines and the like, and the demand for color liquid crystal displays is rapidly increasing.

Under such circumstances, there are demands for the color filters used in liquid crystal display elements to have high color purity.

Known examples of color filters that are formed on elements in order to chromatize solid-state image pickup elements or liquid crystal display elements, include a color filter composed of a yellow filter layer, a magenta filter layer and a cyan filter layer that are formed adjacently to each other in the same plane on a substrate, and a color filter composed of a red filter layer, a green filter layer, and a blue filter layer.

In recent years, a further increase in definition has become desirable in color filters. However, since conventional pigment dispersion systems have a problem that the resolution does not improve, and unevenness occurs due to coarse particles of the pigment, the conventional pigment dispersion systems are not suitable for the applications where fine patterns are required, such as in solid-state image pickup elements. In order to solve this problem, it has been traditionally suggested to use dyes (see, for example, JP 1994-075375A (JP H06-75375A)).

Also, it is known that a red dye is used in the red filter array of a color filter (see, for example, JP 1993-005067A (JP H05-005067A)).

However, colored patterns obtained by using dyes do not exhibit sufficient heat resistance and light fastness. Therefore, investigations have been conducted on color filters using organic pigments which have excellent heat resistance and light fastness.

Examples of the method for producing a color filter which uses an organic pigment include a photolithographic method (see, for example, JP 1989-152449A (JP H01-152449A)) in which a process of performing patterning by exposing and developing a composition having an organic pigment dispersed in a photosensitive resin is repeated a necessary number of times, and printing methods such as offset printing and inkjet printing, in which an ink containing an organic pigment is used.

Use of organic pigments having excellent heat resistance and light fastness, such as anthraquinone-based pigments, diketopyrrolopyrrole-based pigments, quinacridone-based pigments, isoindoline-based pigments, perinone-based pigments, perylene-based pigments, and condensed azo-based pigments, has been taken into consideration. However, there is a problem that these pigments are generally not easily dispersed in color filters, and it is difficult to obtain a color filter having high transparency.

Similarly, for color filters composed of a yellow filter layer, a magenta filter layer and a cyan filter layer, a further improvement of fastness is desirable for the yellow colorant used in yellow filter layers.

Furthermore, WO 05/052074 A proposes a red ink composition for color filters containing a monoazo compound containing a naphthalene ring. However, a color filter using the compound described in WO 05/052074 A is not satisfactory in terms of contrast, and an increase in contrast is desired.

SUMMARY OF THE INVENTION

It is an object of the present invention to provide an azo compound and an azo pigment, which has excellent fastness such as light fastness, heat resistance and solvent resistance, and can exhibit excellent dispersion stability (stability of a dispersion over time) when incorporated into a liquid; a pigment dispersion, a coloring composition, a coloring composition for color filters, an ink for inkjet recording, a printing ink, a coating material, a dye, and a resist ink, which use the azo compound and the azo pigment; and a method for preparing the coloring composition for color filters described above.

Another object of the present invention is to provide a color filter having excellent fastness such as light fastness, heat resistance and solvent resistance and having excellent contrast, which is obtained by using the coloring composition for color filters described above.

The inventors of the present invention conducted thorough investigations, and as a result, they found that a specific nitrogen-containing heterocyclic azo pigment has a satisfactory hue and exhibits satisfactory fastness against light, heat and solvents. Specific means for addressing the objects described above will be described below.

[1] An azo compound represented by the following formula (1), a tautomer thereof, and a salt or hydrate of the azo compound or the tautomer:

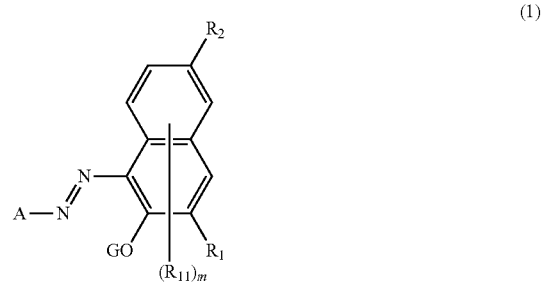

wherein in the formula (1),

A represents a heterocyclic group; G represents a hydrogen atom, an aliphatic group, an aromatic group, or a heterocyclic group; $R_1$ and $R_2$ each independently represent a group represented by the following formula (2) or (3):

(3)

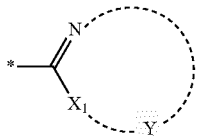

wherein R₃ represents an amino group, an aliphatic oxy group, an aliphatic group, an aromatic group, an aromatic oxy group, or a heterocyclic group;

$X_1$ represents —O—, —S—, —NR— or —N=; R represents a hydrogen atom or an aliphatic group;

Y represents a divalent group which forms a heterocyclic ring together with the nitrogen atom and $X_1$;

$R_{11}$ represents a substituent, and when there are plural $R_{11}$'s, $R_{11}$'s may be identical with or different from each other;

* represents a bond that is bonded to the naphthalene ring in the formula (1); and m's each independently represent an integer of 0 to 4.

[2] The azo compound, the tautomer thereof, and the salt or hydrate of the azo compound or the tautomer as described in the above item [1], wherein the compound represented by the formula (1) is represented by the following formula (4):

(4)

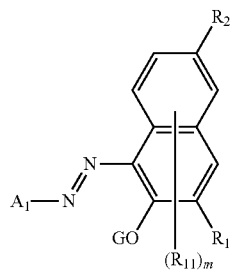

wherein in the formula (4), $A_1$ represents a 5-membered or 6-membered aromatic heterocyclic group represented by any one of the following formulae (A-1) to (A-34);

G, $R_1$, $R_2$, $R_{11}$ and m have the same meanings as G, $R_1$, $R_2$, $R_{11}$ and m, respectively, defined in the formula (1);

(A-1)

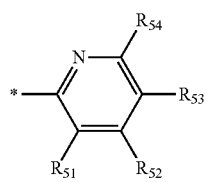

(A-2)

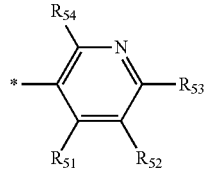

(A-3)

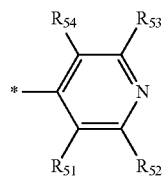

(A-4)

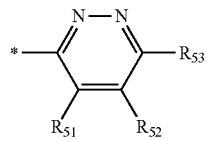

(A-5)

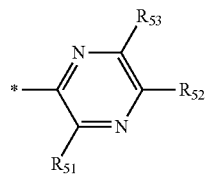

(A-6)

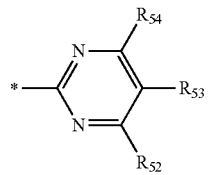

(A-7)

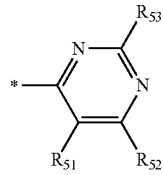

(A-8)

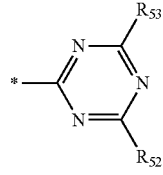

(A-9)

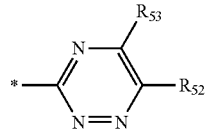

(A-10)

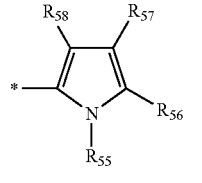

(A-11)

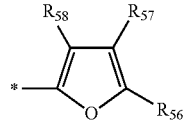

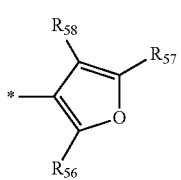 (A-12)
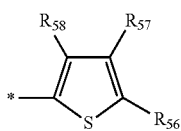 (A-13)
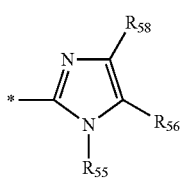 (A-14)
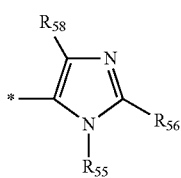 (A-15)
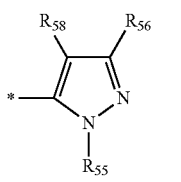 (A-16)
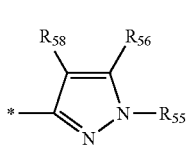 (A-17)
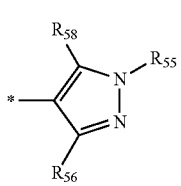 (A-18)
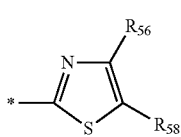 (A-19)
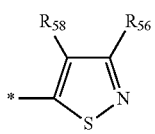 (A-20)
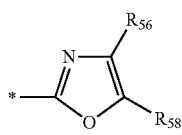 (A-21)
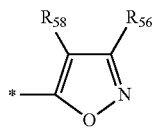 (A-22)
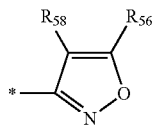 (A-23)
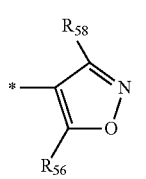 (A-24)
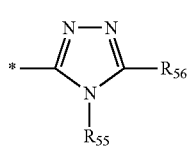 (A-25)
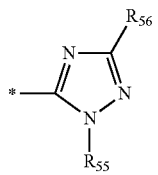 (A-26)
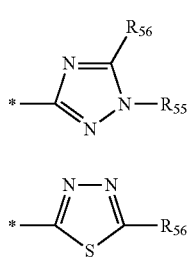 (A-27)
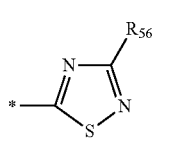 (A-28)
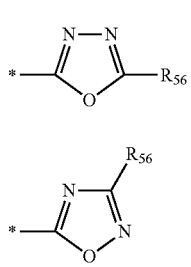 (A-29)
(A-30)
(A-31)

-continued

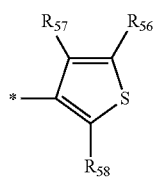
(A-32)

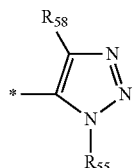
(A-33)

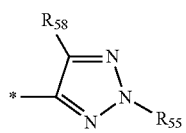
(A-34)

wherein in the formulae (A-1) to (A-34), $R_{51}$ to $R_{58}$ each represent a hydrogen atom, or a substituent, while adjacent substituents may be bonded to each other to form a 5-membered or 6-membered ring; and * represents the bonding position with the azo group of the formula (4).

[3] The azo compound, the tautomer thereof, and the salt or hydrate of the azo compound or the tautomer as described in the above item [2], wherein in the azo compound represented by the formula (4), $A_1$ represents any one of the above formulae (A-14) to (A-16), (A-25) and (A-26).

[4] The azo compound, the tautomer thereof, and the salt or hydrate of the azo compound or the tautomer as described in the above item [3], wherein the azo compound represented by the formula (1) is represented by the following formula (5):

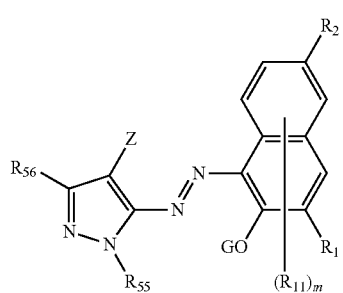
(5)

wherein in the formula (5), G, $R_1$, $R_2$, $R_{11}$, $R_{55}$, $R_{56}$ and m have the same meanings as G, $R_1$, $R_2$, $R_{11}$, $R_{55}$, $R_{56}$ and m, respectively, defined in the formula (4); and Z represents an electron-withdrawing group having a Hammett σp value of 0.2 or greater.

[5] The azo compound, the tautomer thereof, and the salt or hydrate of the azo compound or the tautomer as described in the above item [2], wherein in the azo compound represented by the formula (4), $A_1$ represents any one of the formulae (A-17), (A-18), (A-20), (A-22) to (A-24), (A-27), (A-28), (A-31), and (A-32).

[6] The azo compound, the tautomer thereof, and the salt or hydrate of the azo compound or the tautomer as described in the above item [5], wherein the azo compound represented by the formula (4) is represented by the following formula (6):

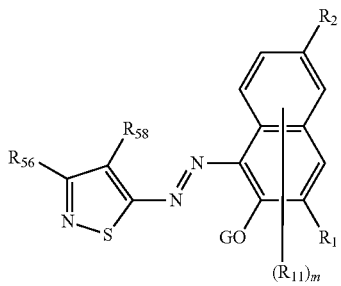
(6)

wherein in the formula (6), G, $R_1$, $R_2$, $R_{11}$, $R_{56}$, $R_{58}$ and m have the same meanings as G, $R_1$, $R_2$, $R_{11}$, $R_{56}$, $R_{58}$ and m, respectively, defined in the formula (4); and $R_{56}$ and $R_{58}$ may be bonded to each other to form a 5-membered or 6-membered ring.

[7] The azo compound, the tautomer thereof, and the salt or hydrate of the azo compound or the tautomer as described in any one of the above items [1] to [6], wherein in the formula (2), $R_3$ represents an amino group or an aliphatic oxy group; in the formula (3), $X_1$ represents —S— or —NR—; R represents a hydrogen atom or an aliphatic group; and in the formula (1), G represents a hydrogen atom.

[8] The azo compound, the tautomer thereof, and the salt or hydrate of the azo compound or the tautomer as described in any one of the above items [1] to [7], wherein in the formula (1), $R_1$ and $R_2$ each represent a group represented by the formula (3).

[9] An azo pigment using the azo compound, the tautomer thereof, and the salt or hydrate of the azo compound or the tautomer as described in any one of the above items [1] to [8].

[10] A pigment dispersion containing at least one kind of the azo pigment described in the above item [9].

[11] A coloring composition containing at least one kind of the azo pigment described in the above item [9].

[12] A coloring composition for color filters, using the coloring composition described in the above item [11] for a color filter application.

[13] The coloring composition for color filters as described in the above item [12], further containing a polymerizable compound and a solvent.

[14] The coloring composition for color filters as described in the above item [13], wherein the polymerizable compound is a photosensitive compound.

[15] The coloring composition for color filters as described in the above item [13] or [14], wherein the solvent is a fatty acid ester.

[16] The coloring composition for color filters as described in any one of the above items [12] to [15], further containing one or more dispersants selected from a surfactant, a silicone-based additive, a pigment-based additive, a silane-based coupling agent, and a titanium-based coupling agent.

[17] A color filter formed by using the coloring composition for color filters as described in any one of the above items [12] to [16].

[18] The color filter as described in the above item [17], formed by a photolithographic method or an inkjet method.

[19] A method for preparing the coloring composition for color filters as described in any one of the above items [12] to [16], the method including a step of dispersing one or more dispersants selected from the group consisting of a surfactant, a silicone-based additive, a pigment-based additive, a silane coupling agent and a titanium coupling agent, and an azo compound represented by the formula (1), a tautomer, a salt or hydrate of the azo compound or the tautomer, in a portion of a solvent to obtain a pigment dispersion; and a step of mixing the pigment dispersion with a polymerizable compound and the rest of the solvent.

[20] An ink for inkjet recording utilizing the pigment dispersion as described in the above item [10].

[21] A printing ink containing the azo compound, the tautomer thereof, and the salt or hydrate of the azo compound or the tautomer as described in any one of the above items [1] to [8], or the azo pigment as described in the above item [9].

[22] A coating material containing the azo compound, the tautomer thereof, and the salt or hydrate of the azo compound or the tautomer as described in any one of the above items [1] to [8], or the azo pigment as described in the above item [9].

[23] A dye containing the azo compound, the tautomer thereof, and the salt or hydrate of the azo compound or the tautomer as described in any one of the above items [1] to [8], or the azo pigment as described in the above item [9].

[24] A resist ink containing the azo compound, the tautomer thereof, and the salt or hydrate of the azo compound or the tautomer as described in any one of the above items [1] to [8], or the azo pigment as described in the above item [9].

According to the present invention, an azo compound and an azo pigment, which has excellent fastness such as light fastness, heat resistance or solvent resistance, and can exhibit excellent dispersion stability (stability of the dispersion over time) when incorporated in a liquid; a pigment dispersion, a coloring composition, a coloring composition for color filters, an ink for inkjet recording, a printing ink, a coating material, a dye, and a resist ink, which use the azo compound and the azo pigment; and a method for preparing a coloring composition for color filters, can be provided.

Furthermore, according to the present invention, a color filter having excellent fastness such as light fastness, heat resistance or solvent resistance and having excellent contrast, which is obtained by using the coloring composition for color filters, can be provided.

DESCRIPTION OF THE PREFERRED EMBODIMENTS

Figure 1:
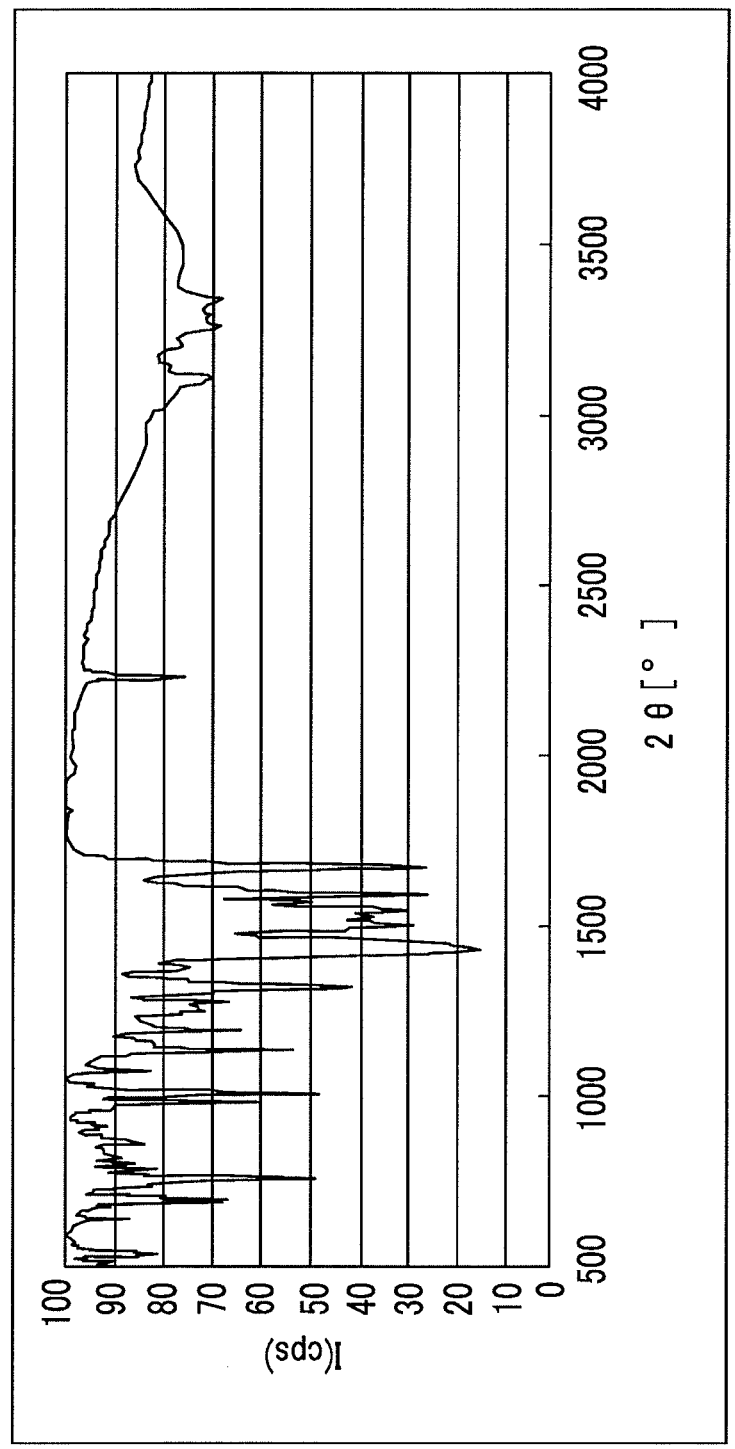
FIG. 1 is a diagram of the infrared absorption spectrum of specific exemplary compound D-21 synthesized according to Synthesis Example 1.
Figure 2:
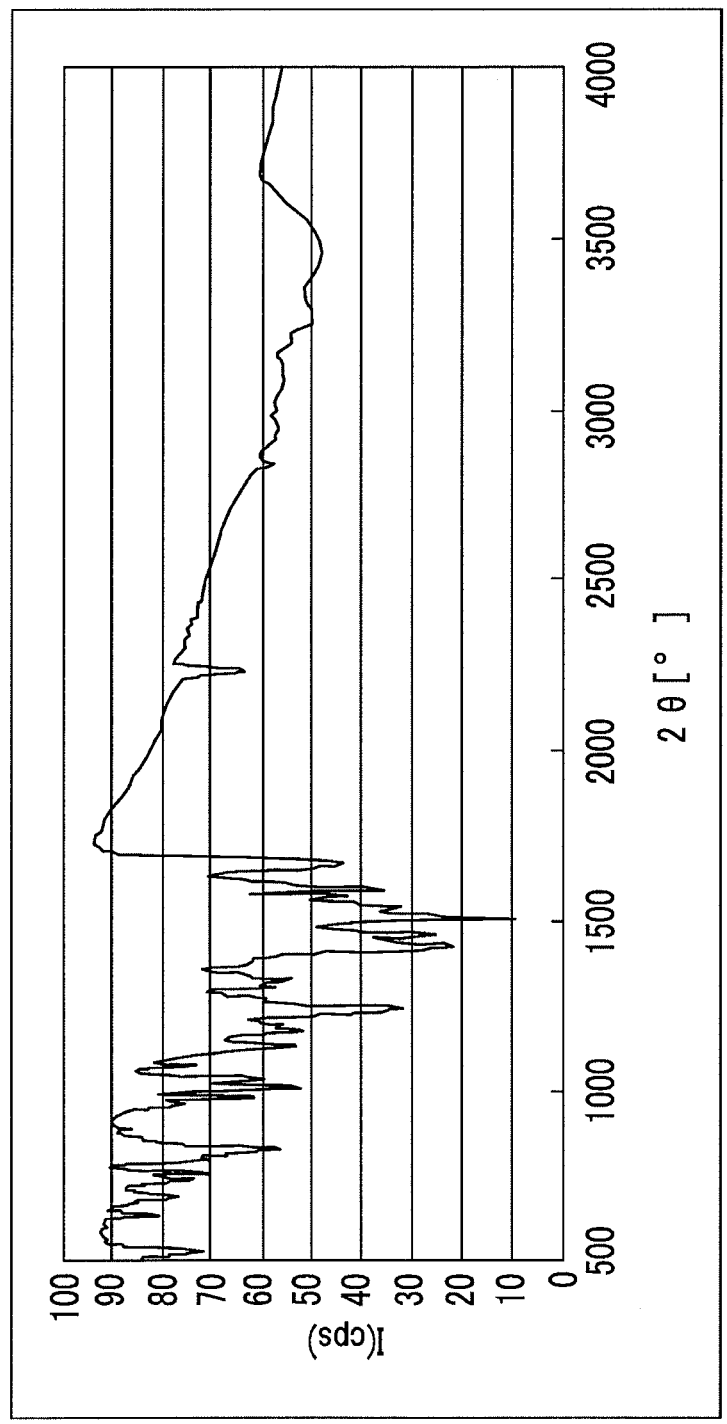
FIG. 2 is a diagram of the infrared absorption spectrum of specific exemplary compound D-22 synthesized according to Synthesis Example 2.
Figure 3:
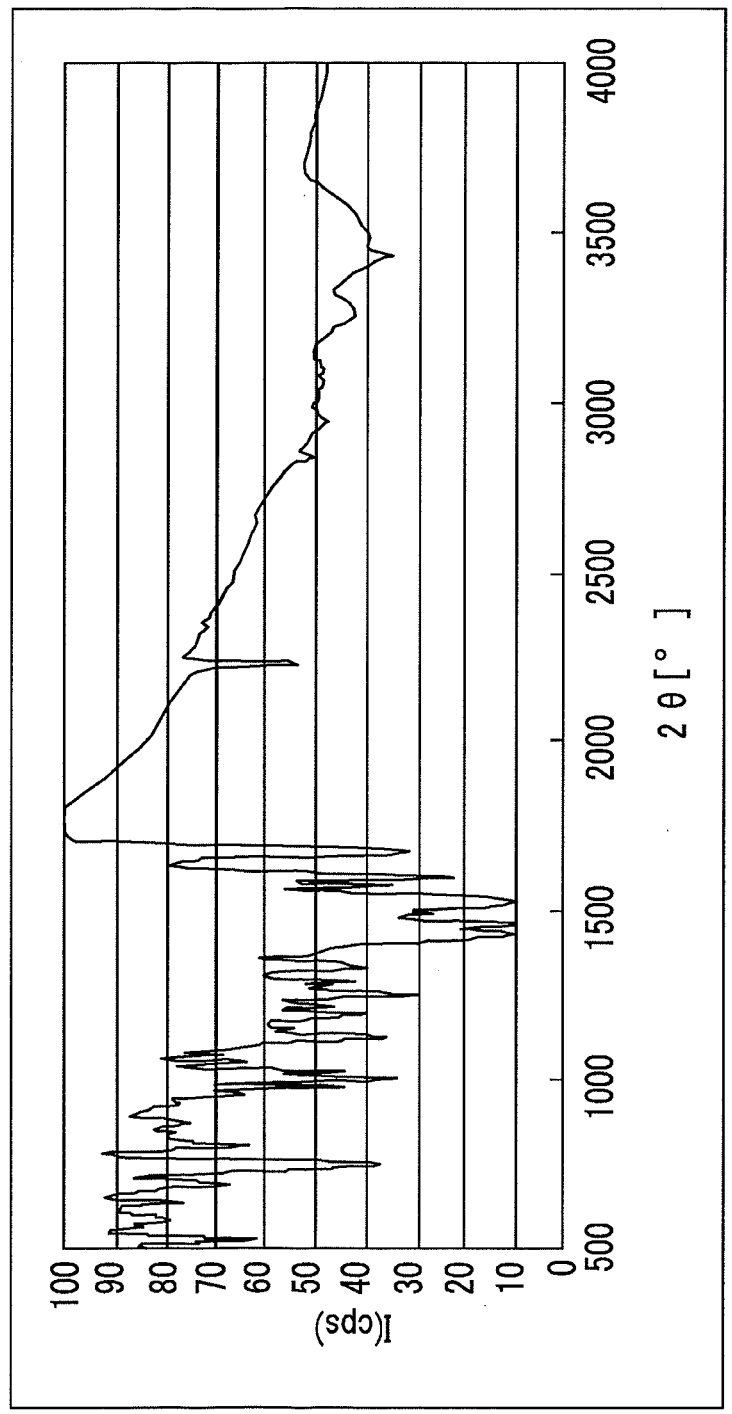
FIG. 3 is a diagram of the infrared absorption spectrum of specific exemplary compound D-23 synthesized according to Synthesis Example 3.
Figure 4:
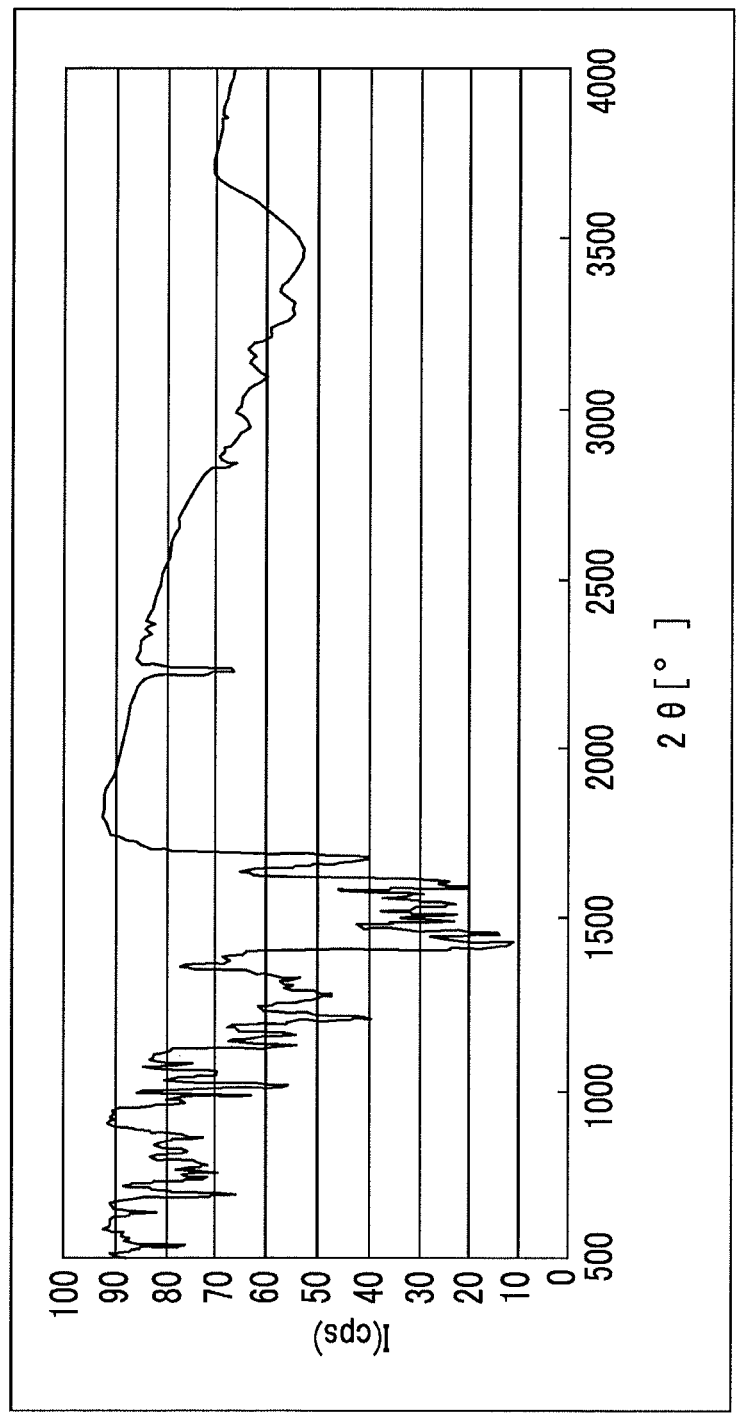
FIG. 4 is a diagram of the infrared absorption spectrum of specific exemplary compound D-24 synthesized according to Synthesis Example 4.
Figure 5:
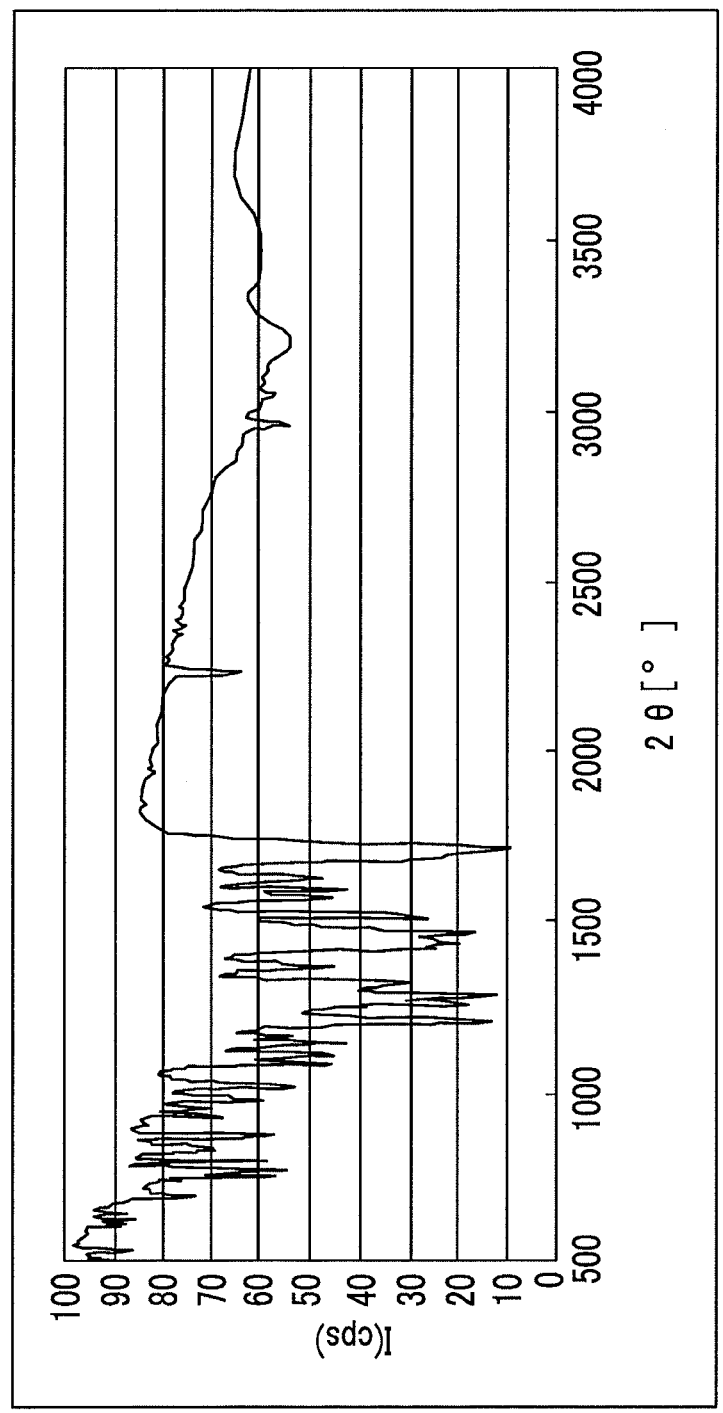
FIG. 5 is a diagram of the infrared absorption spectrum of specific exemplary compound D-26 synthesized according to Synthesis Example 6.
Figure 6:
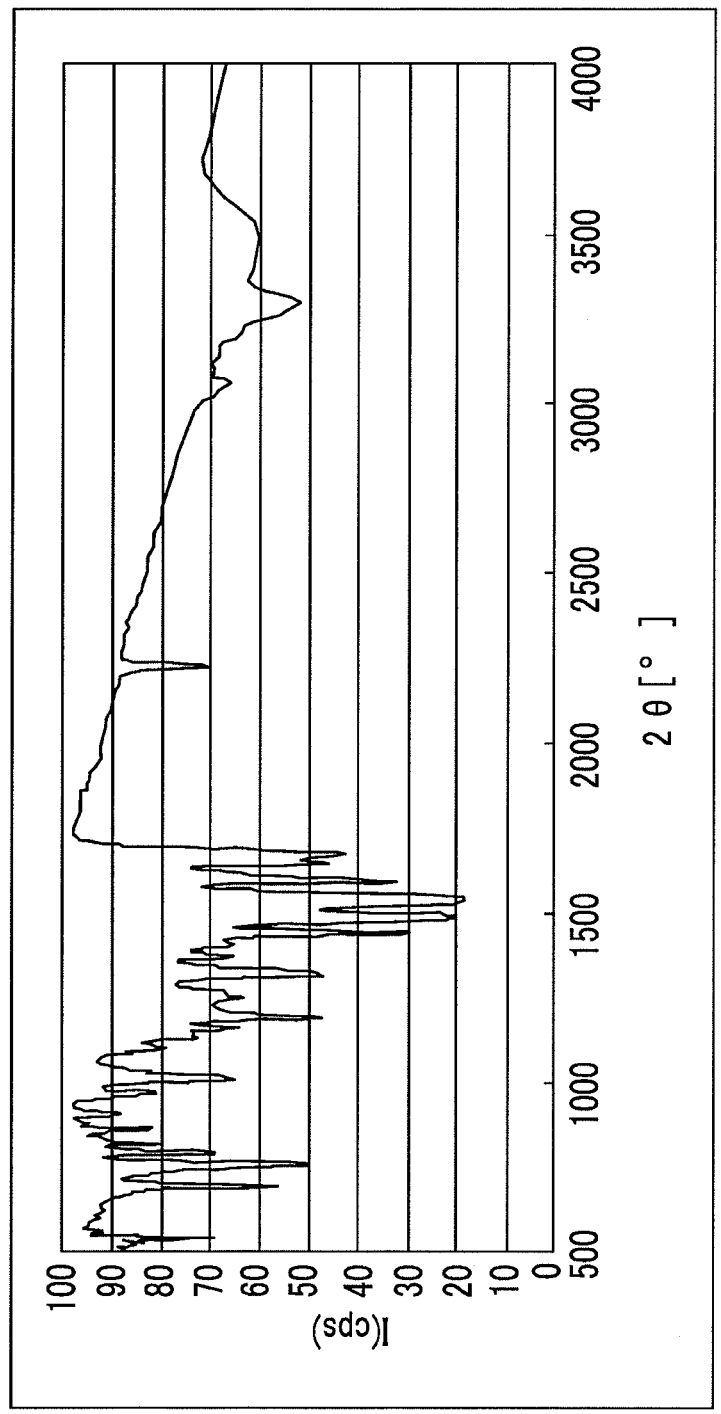
FIG. 6 is a diagram of the infrared absorption spectrum of specific exemplary compound D-28 synthesized according to Synthesis Example 7.

First, the aliphatic group, aromatic group, heterocyclic group and substituents according to the present invention will be described.

In the aliphatic group according to the present invention, the aliphatic moiety may be any of a linear moiety, a branched moiety and a cyclic moiety. Furthermore, the aliphatic moiety may be saturated or unsaturated. Specific examples thereof include an alkyl group, an alkenyl group, a cycloalkyl group, and a cycloalkenyl group. Furthermore, the aliphatic group may be unsubstituted or may have a substituent.

Furthermore, the aromatic group may be monocyclic or a fused ring. Also, the aromatic group may be unsubstituted or may have a substituent. The heterocyclic group may be such that the heterocyclic moiety may have a heteroatom (for example, a nitrogen atom, a sulfur atom, or an oxygen atom) in the ring, and may be a saturated ring or an unsaturated ring. Also, the heterocyclic moiety may be monocyclic or a fused ring, and may also be unsubstituted or may have a substituent.

Furthermore, the substituent according to the present invention is preferably a group capable of substitution, and examples thereof include an aliphatic group, an aromatic group, a heterocyclic group, an acyl group, an acyloxy group, an acylamino group, an aliphatic oxy group, an aromatic oxy group, a heterocyclic oxy group, an aliphatic oxycarbonyl group, an aromatic oxycarbonyl group, a heterocyclic oxycarbonyl group, a carbamoyl group, an aliphatic sulfonyl group, an aromatic sulfonyl group, a heterocyclic sulfonyl group, an aliphatic sulfonyloxy group, an aromatic sulfonyloxy group, a heterocyclic sulfonyloxy group, a sulfamoyl group, an aliphatic sulfonamide group, an aromatic sulfonamide group, a heterocyclic sulfonamide group, an amino group, an aliphatic amino group, an aromatic amino group, a heterocyclic amino group, an aliphatic oxycarbonylamino group, an aromatic oxycarbonylamino group, a heterocyclic oxycarbonylamino group, an aliphatic sulfinyl group, an aromatic sulfinyl group, an aliphatic thio group, an aromatic thio group, a hydroxyl group, a cyano group, a sulfo group, a carboxyl group, an aliphatic oxyamino group, an aromatic oxyamino group, a carbamoylamino group, a sulfamoylamino group, a halogen atom, a sulfamoylcarbamoyl group, a carbamoylsulfamoyl group, a di-aliphatic oxyphosphinyl group, and a di-aromatic oxyphosphinyl group.

The azo pigment according to the present invention preferably does not contain an ionic hydrophilic group (for example, a carboxyl group, a sulfo group, a phosphono group or a quaternary ammonium group) as a substituent from the viewpoint of solubility. When the azo pigment contains an ionic hydrophilic group, the azo pigment is preferably a salt with a polyvalent metal cation (for example, magnesium, calcium or barium), and more preferably a lake pigment.

Here, the Hammett substituent constant σp value used in the present specification will be briefly explained.

Hammett's Rule is an empirical rule proposed by L. P. Hammett in 1935 in order to quantitatively define the influence of a substituent on the reaction or equilibrium of a benzene derivative, but today, this rule is recognized to be valid in a wide range of applications. The substituent constants determined by the Hammett's Rule include the σp value and the σm value, and these values can be found in many common textbooks, but these constants are described in detail in, for example, J. A. Dean, ed., "Lange's Handbook of Chemistry", 12$^{th}$ Edition, 1979 (McGraw-Hill) or "Kagaku no Ryoiki (Realm of Chemistry)", Special Issue, No. 122, p. 96-103, 1979 (Nankodo Co., Ltd.). Meanwhile, it is redundant to say that various substituents will be defined or described by means of the Hammett substituent constant σp in the present invention, but this does not imply that the substituents are limited only to those substituents having Hammett substituent values that are already known in the literature, which can be found in the textbooks described above, and that even though the Hammett substituent constant value of a certain substituent is not known in the literature, the present invention includes the substituent as long as the substituent has a Hammett substituent constant that is included in the scope when measured based on the Hammett's Rule. The compound represented by the formula (1) of the present invention is not a benzene derivative, but the σp value is used as a measure that represents the electronic effect of the substituent, regardless of the position of substitution. In the present invention, the σp value will be used in this sense in the following descriptions.

<Azo Compound>

The azo compound of the present invention is represented by the following formula (1):

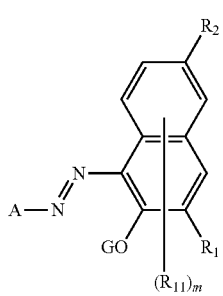
(1)

In the formula (1),

A represents a heterocyclic group; G represents a hydrogen atom, an aliphatic group, an aromatic group, or a heterocyclic group; $R_1$ and $R_2$ each independently represent a group represented by the following formula (2) or formula (3):

$$*\!\!-\!\!\overset{O}{\overset{\|}{C}}\!\!-\!\!R_3 \quad (2)$$

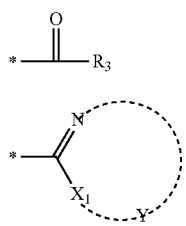
(3)

$R_3$'s each independently represent an amino group, an aliphatic oxy group, an aliphatic group, an aromatic group, an aromatic oxy group, or a heterocyclic group.

$X_1$ represents —O—, —S—, —NR— or —N═; R represents a hydrogen atom or an aliphatic group.

Y represents a divalent group that forms a heterocyclic ring together with the nitrogen atom and $X_1$.

$R_{11}$'s each independently represent a substituent, and when there are plural $R_{11}$'s, $R_{11}$'s may be identical with or different from each other.

* represents a single bond that is bonded to the naphthalene ring in the formula (1).

m's each independently represent an integer of 0 to 4.

The aliphatic group represented by G may have a substituent, and may be saturated or unsaturated. The substituent which may be substituted may be any group mentioned in the section for substituents described above, and may be any group capable of substitution. Preferred examples of the substituent include a hydroxyl group, an aliphatic oxy group, a carbamoyl group, an aliphatic oxycarbonyl group, an aliphatic thio group, an amino group, an aliphatic amino group, an acylamino group, and a carbamoylamino group. The aliphatic group represented by G is preferably an aliphatic group having 1 to 8 carbon atoms in total, and more preferably an alkyl group having 1 to 4 carbon atoms in total, and examples thereof include methyl, ethyl, vinyl, cyclohexyl, and carbamoylmethyl.

The aromatic group represented by G may be fused, and may have a substituent. The substituent which may be substituted may be any group mentioned in the section for substituents described above, and may be any group capable of substitution. Preferred examples of the substituent include a nitro group, a halogen atom, an aliphatic oxy group, a carbamoyl group, an aliphatic oxycarbonyl group, an aliphatic thio group, an amino group, an aliphatic amino group, an acylamino group, and a carbamoylamino group. The aromatic group represented by G is preferably an aromatic group having 6 to 12 carbon atoms in total, and more preferably an aromatic group having 6 to 10 carbon atoms in total. Examples thereof include phenyl, 4-nitrophenyl, 4-acetylaminophenyl, and 4-methanesulfonylphenyl.

The heterocyclic group represented by G may have a substituent, and may be saturated or unsaturated, and may have a fused ring. The substituent which may be substituted may be any group mentioned in the section for substituents described above, and may be any group capable of substitution. Preferred examples of the substituent include a halogen atom, a hydroxyl group, an aliphatic oxy group, a carbamoyl group, an aliphatic oxycarbonyl group, an aliphatic thio group, an amino group, an aliphatic amino group, an acylamino group, and a carbamoylamino group. The heterocyclic group represented by G is preferably a heterocyclic group having 2 to 12 carbon atoms in total that is bonded to a carbon atom, and more preferably a 5-membered or 6-membered heterocyclic ring having 2 to 10 carbon atoms in total that is bonded to a carbon atom. Examples thereof include 2-tetrahydrofuryl, and 2-pyrimidyl.

G is preferably a hydrogen atom. This is because intramolecular hydrogen bonding or intramolecular cross-hydrogen bonding can be easily formed.

As described above, $R_1$ and $R_2$ each independently represent a group represented by the formula (2) or formula (3). $R_1$ and $R_2$ are each preferably a group represented by the formula (3).

The amino group represented by $R_3$ in the formula (2) may have a substituent. The group which may be substituted may be any group mentioned in the section for substituents described above, and may be any group capable of substitution. Preferred examples of the substituent include an aliphatic group, an aromatic group, and a heterocyclic group.

These substituents may each further have a substituent, and this substituent is preferably an aliphatic group, a hydroxyl group, or a substituent having an amide bond, an ether bond, an oxycarbonyl bond, a thioether bond or the like. A substituent having a bond between a heteroatom and a hydrogen atom is more preferred from the viewpoint of facilitating the intermolecular interaction such as intermolecular hydrogen bonding.

The amino group which may have a substituent, as represented by $R_3$, is preferably an unsubstituted amino group, an alkylamino group having 1 to 10 carbon atoms in total, a dialkylamino group having 2 to 10 carbon atoms in total, an aromatic amino group having 6 to 13 carbon atoms in total, or a heterocyclic amino group having 2 to 12 carbon atoms in total, which may be saturated or unsaturated. The amino group represented by $R_3$ is more preferably an unsubstituted amino group, an alkylamino group having 1 to 8 carbon atoms in total, an aromatic amino group having 6 to 13 carbon atoms in total, or a heterocyclic amino group having 2 to 12 carbon atoms, which may be saturated or unsaturated. Examples thereof include methylamino, N,N-dimethylamino, N-phenylamino, and N-(2-pyrimidyl)amino.

The amino group represented by $R_3$ is even more preferably an aromatic amino group having 6 to 13 carbon atoms in total which may have a substituent, or a heterocyclic amino group having 2 to 12 carbon atoms in total, which may have a substituent, and may be saturated or unsaturated.

When $R_3$ is an aromatic amino group, it is preferable that the substituent on the aromatic group have a substituent at the para-position from the bonding position with the amino group, and it is most preferable that the substituent on the aromatic group have a substituent only at the para-position. The substituent may be any group mentioned in the section for substituents described above, and may be any group capable of substitution. Preferred examples of the substituent include an aliphatic group which may have a substituent having 1 to 7 carbon atoms in total, and more preferably 1 to 4 carbon atoms in total (for example, methyl, ethyl, allyl, (i)-propyl, (t)-butyl, or trifluoromethyl); an aliphatic oxy group which may have a substituent having 1 to 7 carbon atoms in total, and more preferably 1 to 4 carbon atoms in total (for example, methoxy, ethoxy, (i)-propyloxy, or allyloxy); a halogen atom (for example, fluorine, chlorine, or bromine); a carbamoyl group which may have a substituent having 1 to 7 carbon atoms in total, and more preferably 1 to 4 carbon atoms in total (for example, carbamoyl, N-phenylcarbamoyl, or N-methylcarbamoyl); a ureido group which may have a substituent having 1 to 7 carbon atoms in total, and more preferably 1 to 4 carbon atoms in total (for example, ureido, N-methylureido, N,N-dimethylureido, N-4-pyridylureido, or N-phenylureido); a nitro group; a cyano group; a heterocyclic ring fused with the aromatic group having 1 to 7 carbon atoms in total (for example, imidazolone); a hydroxyl group; an aliphatic thio group which may have a substituent having 1 to 7 carbon atoms in total, and more preferably 1 to 4 carbon atoms in total (for example, methylthio, ethylthio, (i)-propylthio, allylthio, or (t)-butylthio); an acylamino group which may have a substituent having 2 to 7 carbon atoms in total, and more preferably 2 to 4 carbon atoms in total (for example, acetamino, propionylamino, pivaloylamino, or benzoylamino); an aliphatic oxycarbonylamino group which may have a substituent having 1 to 7 carbon atoms in total, and more preferably 1 to 4 carbon atoms in total (for example, methoxycarbonylamino, or propyloxycarbonylamino); an aliphatic oxycarbonyl group which may have a substituent having 2 to 7 carbon atoms in total, and more preferably 2 to 4 carbon atoms in total (for example, methoxycarbonyl or ethoxycarbonyl); and an acyl group which may have a substituent having 2 to 7 carbon atoms in total, and more preferably 2 to 4 carbon atoms in total (may be an aliphatic carbonyl group, an aromatic carbonyl group, or a heterocyclic carbonyl group, and may have a substituent; the group which may be substituted may be any group mentioned in the section for substituents described above, and may be any group capable of substitution. The acyl group is preferably an acyl group having 2 to 7 carbon atoms in total, and more preferably an acyl group having 2 to 4 carbon atoms, and examples thereof include acetyl, propanoyl, benzoyl, and 3-pyridinecarbonyl).

When the substituent on the aromatic group is substituted at the para-position from the bonding position of the amino group, since the substituent is present at the ends of the molecule, intermolecular interaction such as intermolecular hydrogen bonding is likely to occur, and therefore, a vivid color is obtained. When the substituent on the aromatic group further has a substituent, an aliphatic group, a hydroxyl group, or a substituent having an amide bond, an ether bond, an oxycarbonyl bond, a thioether bond or the like is preferred, and a substituent having a bond between a heteroatom and a hydrogen atom is more preferred from the viewpoint of facilitating intermolecular interaction such as intermolecular hydrogen bonding.

When $R_3$ is a heterocyclic amino group, the substituent thereof may be any group mentioned in the section for substituents described above, and may be any group capable of substitution. The substituent is preferably the same substituent as in the case of the aromatic amino group described above. When the substituent on the heterocyclic group further has a substituent, an aliphatic group, a hydroxyl group, or a substituent having an amide bond, an ether bond, an oxycarbonyl bond, a thioether bond or the like is preferred, and a substituent having a bond between a heteroatom and a hydrogen atom is more preferred from the viewpoint of facilitating intermolecular interaction such as intermolecular hydrogen bonding.

When $R_3$ is an aromatic amino group or heterocyclic amino group, more preferred examples of the substituent include an aliphatic group, an aliphatic oxy group, a halogen atom, a carbamoyl group, a heterocyclic ring fused with the aromatic group, and an aliphatic oxycarbonyl group. Even more preferred examples of the substituent include an aliphatic group having 1 to 4 carbon atoms in total, an aliphatic oxy group having 1 to 4 carbon atoms in total, a halogen atom, a carbamoyl group having 1 to 4 carbon atoms in total, a nitro group, and an aliphatic oxycarbonyl group having 2 to 4 carbon atoms in total.

The aliphatic oxy group represented by $R_3$ in the formula (2) may have a substituent, and may be saturated or unsaturated. The substituent may be any group mentioned in the section for substituents described above, and may be any group capable of substitution. Preferred examples of the substituent include a hydroxyl group, an aliphatic oxy group, a carbamoyl group, an aliphatic oxycarbonyl group, an aliphatic thio group, an amino group, an aliphatic amino group, and a carbamoylamino group. The aliphatic oxy group of $R_3$ is preferably an alkoxy group having 1 to 8 carbon atoms in total, more preferably an alkoxy group having 1 to 4 carbon atoms in total, and even more preferably an alkoxy group having 1 to 2 carbon atoms in total, and examples thereof include methoxy, ethoxy, (t)-butoxy, methoxyethoxy, and carbamoylmethoxy.

The aliphatic group represented by $R_3$ in the formula (2) may have a substituent, and may be saturated or unsaturated. The substituent may be any group mentioned in the section for substituents described above, and may be any group capable of substitution. Preferred examples of the substituent include a hydroxyl group, an aliphatic oxy group, a carbamoyl group, an aliphatic oxycarbonyl group, an aliphatic thio group, an amino group, an aliphatic amino group, an acylamino group, and a carbamoylamino group. The aliphatic group of $R_3$ is preferably an alkyl group having 1 to 8 carbon atoms in total, and more preferably an alkyl group having 1 to 4 carbon atoms in total, and examples thereof include methyl, ethyl, (s)-butyl, methoxyethyl, and carbamoylmethyl.

The aromatic group represented by $R_3$ in the formula (2) may have a substituent, and may be saturated or unsaturated. The substituent may be any group mentioned in the section for substituents described above, and may be any group capable of substitution. Preferred examples of the substituent include an aliphatic group, an aliphatic oxy group, a halogen atom, a carbamoyl group, a heterocyclic ring fused with the aromatic group, and an aliphatic oxycarbonyl group. The aromatic group of $R_3$ is preferably an aromatic group having 6 to 12 carbon atoms in total, and more preferably an aromatic group having 6 to 10 carbon atoms in total, and examples thereof include phenyl, 4-methylphenyl, and 3-chlorophenyl.

The aromatic oxy group represented by $R_3$ in the formula (2) may have a substituent, and may be saturated or unsaturated. The substituent may be any group mentioned in the section for substituents described above, and may be any group capable of substitution. Preferred examples of the substituent include an aliphatic group, an aliphatic oxy group, a halogen atom, a carbamoyl group, a heterocyclic ring fused with the aromatic group, and an aliphatic oxycarbonyl group. The aromatic group in the aromatic oxy group may be an aromatic group represented by $R_3$ as described above.

The heterocyclic group represented by $R_3$ in the formula (2) may be a saturated heterocyclic group or an unsaturated heterocyclic group, and may have a substituent or may be a fused group. The substituent may be any group mentioned in the section for substituents described above, and may be any group capable of substitution. Preferred examples of the substituent include an aliphatic group, an aliphatic oxy group, a carbamoyl group, a heterocyclic ring fused with the heterocyclic group, and an aliphatic oxycarbonyl group. The heterocyclic group of $R_1$ is preferably a heterocyclic group having 2 to 10 carbon atoms in total, and more preferably a saturated heterocyclic group having 2 to 8 carbon atoms in total and bonded to the nitrogen atom. Examples thereof include 1-piperidyl, 4-morpholinyl, 2-pyrimidyl, and 4-pyridyl.

$R_3$ is preferably an amino group which may have a substituent, an aliphatic oxy group, or a saturated heterocyclic group bonded to the nitrogen atom, more preferably an amino group which may have a substituent, or an aliphatic oxy group, and even more preferably an amino group which may have a substituent.

$R_3$ is also preferably an amino group represented by $-N(R_{O1})-R_{O2}-N(R_{O3})(R_{O4})$ or $-N(R_{O1})-R_{O5}$.

Here, $R_{O1}$ represents a hydrogen atom, an aliphatic group, an aromatic group, or a heterocyclic group, and preferably represents a hydrogen atom. $R_{O2}$ represents an alkylene group, an arylene group, a carbonyl group, or a thiocarbonyl group, and preferably represents a carbonyl group. $R_{O3}$ to $R_{O5}$ each independently represent a hydrogen atom, an aliphatic group, an aromatic group, or a heterocyclic group, and $R_{O1}$ with $R_{O5}$, or $R_{O3}$ with $R_{O4}$ may be joined together to form a heterocyclic ring. Examples of the heterocyclic ring which may be formed include rings of cyclic amino groups, such as pyrrole, pyrroline, pyrrolidine, pyrrolidone, indole, indoline, isoindole, carbazole, benzoindole, imidazole, pyrazole, pyrazoline, oxazine, phenoxazine, benzocarbazole, and thiomorpholine.

The respective groups as $R_{O1}$ to $R_{O5}$ may further have substituents.

$R_{O3}$ is preferably a hydrogen atom because intramolecular hydrogen bonding or intramolecular cross-hydrogen bonding can be easily formed.

$R_{O4}$ is preferably an alkyl group or an aromatic group from the viewpoints of color and durability (heat resistance and light fastness), more preferably an aromatic group, and even more preferably a phenyl group.

$R_{O5}$ is preferably an aromatic group or a heterocyclic group. The aromatic group and heterocyclic group are preferably unsubstituted groups, or groups substituted with an aliphatic group, an alkoxy group, a halogen atom, or an alkylthio group. The aromatic group is preferably a phenyl group or a naphthyl group. The heterocyclic group is preferably a nitrogen-containing heteroaromatic group, and more preferably a pyridyl group.

Furthermore, as described above, $X_1$ in the formula (3) represents $-O-$, $-S-$, $-NR-$ or $-N=$, and R represents a hydrogen atom or an aliphatic group. $X_1$ preferably represents $-S-$ or $-NR-$. The aliphatic group of R may be the same as the aliphatic group for $R_3$. R is preferably a hydrogen atom.

Y is a divalent group forming a heterocyclic ring together with the nitrogen atom and $X_1$, and examples thereof include an alkylene group (preferably having 1 to 5 carbon atoms), an alkenylene group (preferably 2 to 5 carbon atoms), an arylene group (preferably having 6 to 10 carbon atoms), and a heteroarylene group (preferably having 4 to 10 carbon atoms).

Y is preferably an alkenylene group or an arylene group, and more preferably an arylene group.

The heterocyclic ring that is formed by Y together with the nitrogen atom and $X_1$ is preferably a ring composed of nitrogen atoms, oxygen atoms and carbon atoms, or a ring composed of nitrogen atoms and carbon atoms, preferably a 5-membered or 6-membered ring, and more preferably an oxazole ring, a benzoxazole ring, an imidazole ring, or a benzimidazole ring.

The substituent represented by $R_{11}$ may be any group mentioned in the section for substituents described above, and may be any group capable of substitution. The substituent represented by $R_{11}$ is preferably an aliphatic group, an aromatic group, a heterocyclic group, an aliphatic oxycarbonyl group, a carboxyl group, a carbamoyl group which may have a substituent, an acylamino group, a sulfonamide group, a carbamoylamino group which may have a substituent, a sulfamoyl group which may have a substituent, an aliphatic oxy group, an aliphatic thio group, a cyano group, a halogen atom, or a hydroxyl group; more preferably an aliphatic oxycarbonyl group, a carbamoyl group which may have a substituent, an acylamino group, a carbamoylamino group which may have a substituent, an aliphatic oxy group, or a halogen atom; and most preferably an aliphatic oxy group.

When these substituents each further have a substituent, the substituent is preferably an aliphatic group, a hydroxyl group, or a substituent having an amide bond, an ether bond, an oxycarbonyl bond, a thioether bond, or the like, and more preferably a substituent having a bond between a heteroatom and a hydrogen atom, from the viewpoint of facilitating intermolecular interaction such as intermolecular hydrogen bonding.

The aliphatic group represented by $R_{11}$ may have a substituent, and may be saturated or unsaturated. The group which may be substituted may be any group mentioned in the section for substituents described above, and may be any group capable of substitution. The aliphatic group of $R_{11}$ is preferably an alkyl group having 1 to 8 carbon atoms in total, and more preferably an alkyl group having 1 to 6 carbon atoms in total, and examples thereof include methyl, ethyl, (i)-propyl, cyclohexyl, and (t)-butyl.

The aromatic group represented by $R_{11}$ may have a substituent, and may be saturated or unsaturated. The group which may be substituted may be any group mentioned in the section for substituents described above, and may be any group capable of substitution. The aromatic group of $R_{11}$ is preferably an aromatic group having 6 to 12 carbon atoms in total, and more preferably an aromatic group having 6 to 10 carbon atoms in total, and examples thereof include phenyl, 3-methoxyphenyl, and 4-carbamoylphenyl.

The heterocyclic group represented by $R_{11}$ may have a substituent, and may be saturated or unsaturated. The group which may be substituted may be any group mentioned in the section for substituents described above, and may be any group capable of substitution. The heterocyclic group of $R_{11}$ is preferably a heterocyclic group having 2 to 16 carbon atoms in total, and more preferably a 5-membered or 6-membered heterocyclic group having 2 to 12 carbon atoms in total, and examples thereof include 1-pyrrolidinyl, 4-morpholinyl, 2-pyridyl, 1-pyrrolyl, 1-imidazolyl, and 1-benzimidazolyl.

The aliphatic oxycarbonyl group represented by $R_{11}$ may have a substituent, and may be saturated or unsaturated. The group which may be substituted may be any group mentioned in the section for substituents described above, and may be any group capable of substitution. The aliphatic oxycarbonyl group of $R_{11}$ is preferably an alkoxycarbonyl group having 1 to 8 carbon atoms in total, and more preferably an alkoxycarbonyl group having 1 to 6 carbon atoms in total, and examples thereof include methoxycarbonyl, i-propyloxycarbonyl, and carbamoylmethoxycarbonyl.

The carbamoyl group represented by $R_{11}$ may have a substituent. The group which may be substituted may be any group mentioned in the section for substituents described above, and may be any group capable of substitution. Preferred examples include an aliphatic group, an aromatic group, and a heterocyclic group. The carbamoyl group which may have a substituent of $R_{11}$ is preferably a carbamoyl group, an alkylcarbamoyl group having 2 to 9 carbon atoms in total, a dialkylcarbamoyl group having 3 to 10 carbon atoms in total, an arylcarbamoyl group having 7 to 13 carbon atoms in total, or a heterocyclic carbamoyl group having 3 to 12 carbon atoms; and more preferably a carbamoyl group, an alkylcarbamoyl group having 2 to 7 carbon atoms, a dialkylcarbamoyl group having 3 to 6 carbon atoms, an arylcarbamoyl group having 7 to 11 carbon atoms, or a heterocyclic carbamoyl group having 3 to 10 carbon atoms. Examples thereof include carbamoyl, methylcarbamoyl, dimethylcarbamoyl, phenylcarbamoyl, and 4-pyridinecarbamoyl.

The acylamino group represented by $R_{11}$ may have a substituent, and may be aliphatic, aromatic or heterocyclic. The group which may be substituted may be any group mentioned in the section for substituents described above, and may be any group capable of substitution. The acylamino group of $R_{11}$ is preferably an acylamino group having 2 to 12 carbon atoms in total, more preferably an acylamino group having 2 to 8 carbon atoms in total, and even more preferably an alkylcarbonylamino group having 2 to 8 carbon atoms in total. Examples thereof include acetylamino, benzoylamino, 2-pyridinecarbonylamino, and propanoylamino.

The sulfonamide group represented by $R_{11}$ may have a substituent, and may be aliphatic, aromatic, or heterocyclic. The group which may be substituted may be any group mentioned in the section for substituents described above, and may be any group capable of substitution. The sulfonamide group of $R_{11}$ is preferably a sulfonamide group having 1 to 12 carbon atoms in total, more preferably a sulfonamide group having 1 to 8 carbon atoms in total, and even more preferably an alkylsulfonamide group having 1 to 8 carbon atoms in total. Examples thereof include methanesulfonamide, benzenesulfonamide, and 2-pyridinesulfonamide.

The carbamoylamino group represented by $R_{11}$ may have a substituent. The group which may be substituted may be any group mentioned in the section for substituents described above, and may be any group capable of substitution. Preferred examples thereof include an aliphatic group, an aromatic group, and a heterocyclic group. The carbamoylamino group which may have a substituent of $R_{11}$ is preferably a carbamoylamino group, an alkylcarbamoylamino group having 2 to 9 carbon atoms in total, a dialkylcarbamoylamino group having 3 to 10 carbon atoms in total, an arylcarbamoylamino group having 7 to 13 carbon atoms in total, or a heterocyclic carbamoylamino group having 3 to 12 carbon atoms in total; and more preferably a carbamoylamino group, an arylcarbamoylamino group having 2 to 7 carbon atoms in total, a dialkylcarbamoylamino group having 3 to 6 carbon atoms in total, an arylcarbamoylamino group having 7 to 11 carbon atoms in total, or a heterocyclic carbamoylamino group having 3 to 10 carbon atoms in total. Examples thereof include carbamoylamino, methylcarbamoylamino, N,N-dimethylcarbamoylamino, phenylcarbamoylamino, and 4-pyridinecarbamoylamino.

The group which may be substituted as the sulfamoyl group which may have a substituent represented by $R_{11}$ may be any group mentioned in the section for substituents described above, and may be any group capable of substitution. Preferred examples thereof include an aliphatic group, an aromatic group, and a heterocyclic group. The sulfamoyl group which may have a substituent of $R_{11}$ is preferably a sulfamoyl group, an alkylsulfamoyl group having 1 to 9 carbon atoms in total, a dialkylsulfamoyl group having 2 to 10 carbon atoms in total, an arylsulfamoyl group having 7 to 13 carbon atoms in total, or a heterocyclic sulfamoyl group having 2 to 12 carbon atoms in total; more preferably a sulfamoyl group, an alkylsulfamoyl group having 1 to 7 carbon atoms in total, a dialkylsulfamoyl group having 3 to 6 carbon atoms in total, an arylsulfamoyl group having 6 to 11 carbon atoms in total, or a heterocyclic sulfamoyl group having 2 to 10 carbon atoms in total. Examples thereof include sulfamoyl, methylsulfamoyl, N,N-dimethylsulfamoyl, phenylsulfamoyl, and 4-pyridinesulfamoyl.

The aliphatic oxy group represented by $R_{11}$ may have a substituent, and may be saturated or unsaturated. The group which may be substituted may be any group mentioned in the section for substituents described above, and may be any group capable of substitution. The aliphatic oxy group of $R_{11}$ is preferably an alkoxy group having 1 to 8 carbon atoms in total, and more preferably an alkoxy group having 1 to 6 carbon atoms in total. Examples thereof include methoxy, ethoxy, i-propyloxy, cyclohexyloxy, and methoxyethoxy.

The aliphatic thio group represented by $R_{11}$ may have a substituent, and may be saturated or unsaturated. The group which may be substituted may be any group mentioned in the section for substituents described above, and may be any group capable of substitution. The aliphatic thio group of $R_{11}$ is preferably an alkylthio group having 1 to 8 carbon atoms in total, and more preferably an alkylthio group having 1 to 6 carbon atoms in total. Examples thereof include methylthio, ethylthio, carbamoylmethylthio, and t-butylthio.

The halogen atom represented by $R_{11}$ is preferably a fluorine atom, a chlorine atom, or a bromine atom, and more preferably a chlorine atom.

In view of the effects of the present invention, $R_{11}$ is preferably an aliphatic oxy group, an aliphatic oxycarbonyl group, or a carbamoyl group which may have a substituent, and more preferably an aliphatic oxy group.

m represents an integer of 0 to 4, and is preferably an integer of 0 to 3, more preferably 0 or 1, and even more preferably 0.

In view of the effects of the present invention, the azo compound represented by the formula (1) is preferably an azo compound represented by the following formula (4):

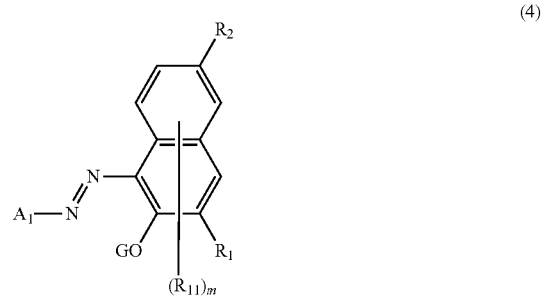

(4)

wherein in the formula (4), $A_1$ represents a 5-membered or 6-membered aromatic heterocyclic group represented by any one of the following formulae (A-1) to (A-34); and G, $R_1$, $R_2$, $R_{11}$ and m have the same meanings as G, $R_1$, $R_2$, $R_{11}$ and m defined in the formula (1).
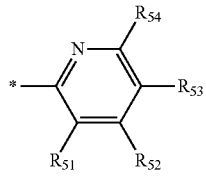 (A-1)
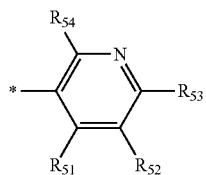 (A-2)
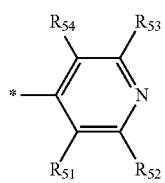 (A-3)
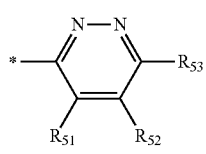 (A-4)
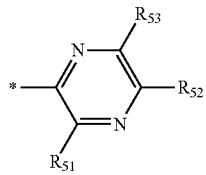 (A-5)
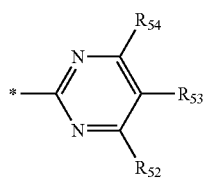 (A-6)
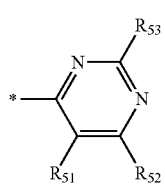 (A-7)
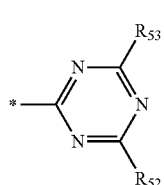 (A-8)
-continued
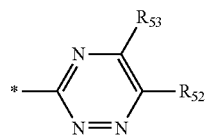 (A-9)
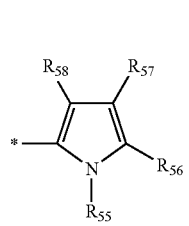 (A-10)
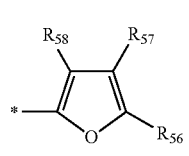 (A-11)
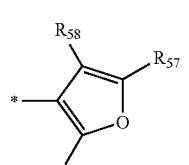 (A-12)
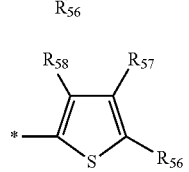 (A-13)
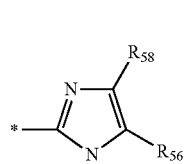 (A-14)
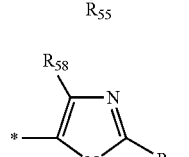 (A-15)
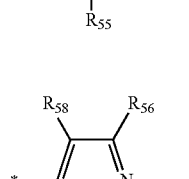 (A-16)
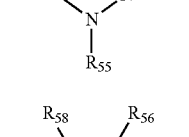 (A-17)
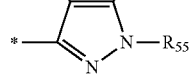

(A-18) 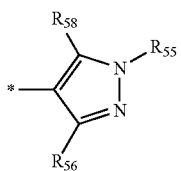

(A-19) 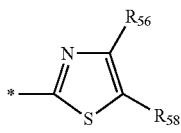

(A-20) 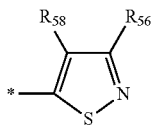

(A-21) 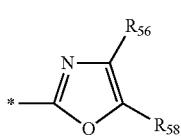

(A-22) 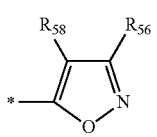

(A-23) 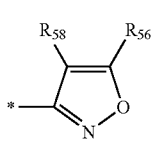

(A-24) 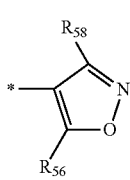

(A-25) 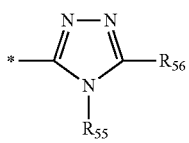

(A-26) 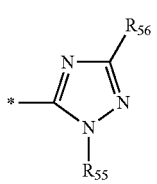

(A-27) 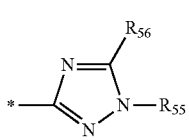

(A-28) 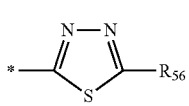

(A-29) 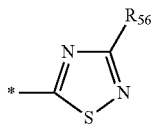

(A-30) 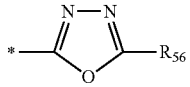

(A-31) 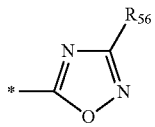

(A-32) 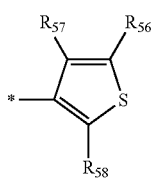

(A-33) 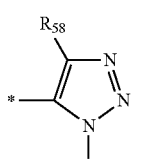

(A-34) 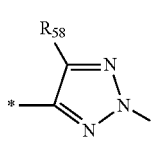

wherein in the formulae (A-1) to (A-34), $R_{51}$ to $R_{58}$ each represent a hydrogen atom or a substituent, and adjacent substituents may be bonded to each other to form a 5-membered or 6-membered ring; * represents the bonding position with the azo group of the formula (4).

The substituent represented by $R_{51}$ to $R_{54}$ may be any group mentioned in the section for substituents described above, and may be any group capable of substitution. The substituent of $R_{51}$ to $R_{54}$ is preferably an aliphatic group, an aromatic group, a heterocyclic group, an aliphatic oxycarbonyl group, a carbamoyl group which may have a substituent, an acylamino group, a sulfonamide group, an aliphatic oxy group, an aliphatic thio group, or a cyano group; and more preferably an aliphatic group, an aliphatic oxycarbonyl group, a carbamoyl group which may have a substituent, an aliphatic oxy group, or a cyano group.

In view of the effects of the present invention, $R_{51}$ to $R_{54}$ are each preferably a hydrogen atom, an aliphatic group, an aromatic group, a heterocyclic group, an aliphatic oxycarbonyl group, a carbamoyl group which may have a substituent, an acylamino group, a sulfonamide group, an aliphatic oxy group, an aliphatic thio group, or a cyano group; and more preferably a hydrogen atom, an aliphatic group, an aliphatic oxycarbonyl group, a carbamoyl group which may have a substituent, an aliphatic oxy group, or a cyano group.

The substituent represented by $R_{55}$ may be any group mentioned in the section for substituents described above, and may be any group capable of substitution. The substituent of $R_{55}$ is preferably an aliphatic group, an aromatic group, a heterocyclic group or the like, and more preferably an aliphatic group, an aromatic group, or a 5-membered or 6-membered aromatic heterocyclic group containing a nitrogen atom at a position adjacent to the bonding site with the nitrogen atom.

In view of the effects of the present invention, $R_{55}$ is preferably an aliphatic group, an aromatic group, or a heterocyclic group; more preferably an aliphatic group, an aromatic group, or a 5-membered or 6-membered aromatic heterocyclic group containing a nitrogen atom at a position adjacent to the bonding site with the nitrogen atom; and even more preferably a 5-membered or 6-membered aromatic heterocyclic group containing a nitrogen atom at a position adjacent to the bonding site with the nitrogen atom. When $R_{55}$ is a 5-membered or 6-membered aromatic heterocyclic group containing a nitrogen atom at a position adjacent to the bonding site with the nitrogen atom, the intermolecular interaction as well as the intramolecular interaction of the colorant molecules is likely to be strongly established. Thereby, a pigment having a stable molecular arrangement can be easily constructed, and it is preferable from the viewpoint of exhibiting a satisfactory hue and high fastness (light fastness, and fastness to gases, heat, water and the like).

In view of the effects of the present invention, the 5-membered or 6-membered aromatic heterocyclic group containing a nitrogen atom at a position adjacent to the bonding site with the nitrogen atom, which is preferred as $R_{55}$, may have a substituent, and the group which may be substituted may be any group mentioned in the section for substituents described above, and may be any group capable of substitution. Preferred examples of the substituent include a hydroxyl group, an aliphatic oxy group, a carbamoyl group, an aliphatic oxycarbonyl group, an aliphatic thio group, an amino group, an aliphatic amino group, an acylamino group, and a carbamoylamino group, and the substituent may be a saturated heterocyclic ring or an unsaturated heterocyclic ring, or may be a fused heterocyclic ring. The 5-membered or 6-membered aromatic heterocyclic group is preferably a 5-membered or 6-membered aromatic heterocyclic group having 2 to 12 carbon atoms in total and containing a nitrogen atom at a position adjacent to the bonding site with the nitrogen atom; and more preferably a 5-membered or 6-membered aromatic heterocyclic group having 2 to 10 carbon atoms in total and containing a nitrogen atom at a position adjacent to the bonding site with the nitrogen atom. Examples thereof include 2-thiazolyl, 2-benzothiazolyl, 2-oxazolyl, 2-benzoxazolyl, 2-pyridyl, 2-pyrazinyl, 3-pyridazinyl, 2-pyrimidinyl, 4-pyrimidinyl, 2-imidazolyl, 2-benzimidazolyl, and 2-triazinyl, and these heterocyclic groups may form tautomeric structures with the substituents.

In view of the effects of the present invention, the aromatic group preferred as $R_{55}$ may have a substituent, and the group which may be substituted may be any group mentioned in the section for substituents described above, and may be any group capable of substitution. Preferred examples of the substituent include a hydroxyl group, a nitro group, an aliphatic oxy group, a carbamoyl group, an aliphatic oxycarbonyl group, an aliphatic thio group, an amino group, an aliphatic amino group, an acylamino group, and a carbamoylamino group. The aromatic group of $R_{55}$ is preferably an aromatic group having 6 to 12 carbon atoms in total, and more preferably an aromatic group having 6 to 10 carbon atoms in total, and examples thereof include phenyl, 3-methoxyphenyl, and 4-carbamoylphenyl. Among these, a phenyl group is preferred.

In the formula (4), $R_{55}$ is preferably any one of the groups of the following formulae (Y-1) to (Y-15), and in order to obtain a structure which is likely to adopt an intramolecular hydrogen bonding structure, $R_{55}$ is more preferably any one of the groups of the following formulae (Y-1) to (Y-6), even more preferably any one of the following (Y-1), (Y-3), (Y-4) and (Y-6), and particularly preferably the following (Y-1) or (Y-4). Symbol * in the formulae (Y-1) to (Y-15) represents the site of bonding with the N atom of the heterocyclic ring. $Y_1$ to $Y_{11}$ each represent a hydrogen atom or a substituent. $G_{11}$ in the formulae (Y-13) and (Y-15) represents a non-metal atomic group which can constitute a 5-membered or 6-membered heterocyclic ring, and the heterocyclic ring represented by $G_{11}$ may be unsubstituted or may have a substituent. The heterocyclic ring may be monocyclic or may be a fused ring. The groups of the formulae (Y-1) to (Y-15) may form tautomeric structures with the substituents.

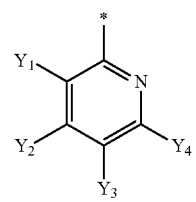

(Y-1)

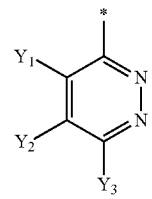

(Y-2)

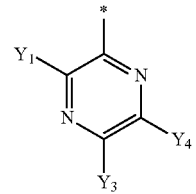

(Y-3)

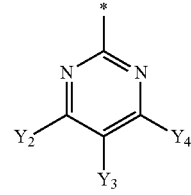

(Y-4)

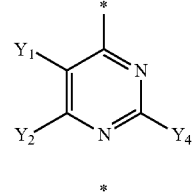

(Y-5)

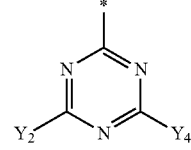

(Y-6)

-continued (Y-7) 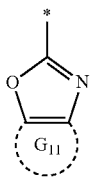

(Y-8) 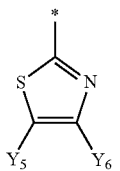

(Y-9) 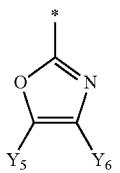

(Y-10) 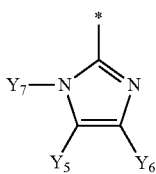

(Y-11) 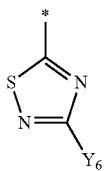

(Y-12) 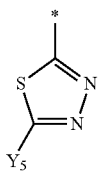

(Y-13) 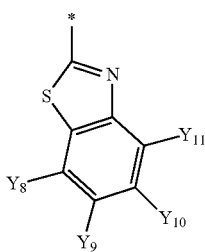

(Y-14) 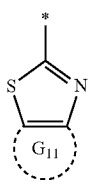

(Y-15) 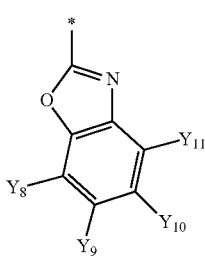

In view of the effects of the present invention, $Y_1$ to $Y_{11}$ are each preferably a hydrogen atom, an aliphatic group, an aromatic group, a heterocyclic group, an aliphatic oxycarbonyl group, a carbamoyl group which may have a substituent, an acylamino group, a sulfonamide group, an aliphatic oxy group, an aliphatic thio group, a cyano group or the like; and more preferably a hydrogen atom, an aliphatic group, an aliphatic oxycarbonyl group, a carbamoyl group which may have a substituent, an aliphatic oxy group, or a cyano group.

The substituent represented by $R_{56}$ or $R_{57}$ may be any group mentioned in the section for substituents described above, and may be any group capable of substitution. The substituent of $R_{56}$ and $R_{57}$ is preferably an aliphatic group, an aromatic group, a heterocyclic group, an aliphatic oxycarbonyl group, a carbamoyl group which may have a substituent, an acylamino group, a sulfonamide group, an aliphatic oxy group, an aliphatic thio group, a cyano group or the like; and more preferably an aliphatic group, an aliphatic oxy group, an aliphatic thio group, a cyano group or the like.

In view of the effects of the present invention, $R_{56}$ and $R_{57}$ are each preferably a hydrogen atom, an aliphatic group, an aromatic group, a heterocyclic group, an aliphatic oxycarbonyl group, a carbamoyl group which may have a substituent, an acylamino group, a sulfonamide group, an aliphatic oxy group, an aliphatic thio group, a cyano group or the like; and more preferably a hydrogen atom, an aliphatic group, an aliphatic oxy group, an aliphatic thio group, or a cyano group.

The substituent represented by $R_{58}$ may be any group mentioned in the section for substituents described above, and may be any group capable of substitution. In view of the effects of the present invention, $R_{58}$ is preferably a heterocyclic group, or an electron-withdrawing group having a Hammett substituent constant σp value of 0.2 or greater; and more preferably an electron-withdrawing group having a σp value of 0.3 or greater. As the upper limit, $R_{58}$ is an electron-withdrawing group having a σp value of 1.0 or less. When the σp value of $R_{58}$ is in this range, the substituents can be synthesized by the same synthesis method, and the same effect in terms of increasing the wavelength of the hue can be obtained.

Specific examples of $R_{58}$ which is an electron-withdrawing group having a σp value of 0.2 or greater include an acyl group, an acyloxy group, a carbamoyl group, an alkyloxycarbonyl group, an aryloxycarbonyl group, a cyano group, a nitro group, a dialkylphosphono group, a diarylphosphono group, a diarylphosphinyl group, an alkylsulfinyl group, an arylsulfinyl group, an alkylsulfonyl group, an arylsulfonyl group, a sulfonyloxy group, an acylthio group, a sulfamoyl group, a thiocyanate group, a thiocarbonyl group, a halogenated alkyl group, a halogenated alkoxy group, a halogenated aryloxy group, a halogenated alkylamino group, a halogenated alkylthio group, an aromatic group substituted with another electron-withdrawing group having a σp value of 0.2 or greater, a heterocyclic group, a halogen atom, an azo group, and a selenocyanate group.

According to an embodiment, the azo compound represented by the formula (4) is preferably such that $A_1$ represents any one of (A-14) to (A-16), (A-25) and (A-26); more preferably, $A_1$ represents any one of (A-14) to (A-16) and (A-26); and even more preferably, $A_1$ represents (A-16).

In view of the effects of the present invention, the azo compound represented by the formula (4) is preferably an azo compound represented by the following formula (5):

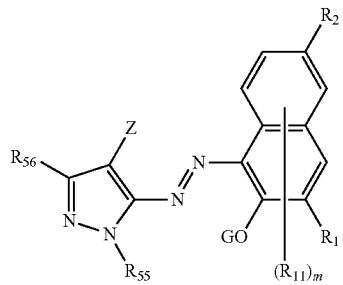

(5)

wherein in the formula (5), G, $R_1$, $R_2$, $R_{11}$, $R_{55}$, $R_{56}$ and m have the same meanings as G, $R_1$, $R_2$, $R_{11}$, $R_{55}$, $R_{56}$ and m defined in the formula (4); and Z represents an electron-withdrawing group having a Hammett σp value of 0.2 or greater.

Examples of the substituent having a Hammett σp value of 0.2 or greater as represented by Z include the groups described above in connection with $R_{58}$ of the formula (4).

The substituents for G, $R_1$, $R_2$, $R_{11}$, $R_{55}$, $R_{56}$ and m of the compound represented by the formula (5) have the same preferred ranges as the substituents for the formula (4).

In view of the effects of the present invention, Z is preferably an acyl group, a carbamoyl group, an alkyloxycarbonyl group, a cyano group, an alkylsulfonyl group, or a sulfamoyl group; more preferably a carbamoyl group, an alkyloxycarbonyl group, or a cyano group; and most preferably a cyano group.

In view of the effects of the present invention, the compound represented by the formula (4) is such that the "total number of carbon atoms/number of azo groups" is preferably 40 or less, and more preferably 30 or less. In view of the effects of the present invention, the compound represented by the formula (4) is preferably such that the "molecular weight/number of azo groups" is 700 or less. In view of the effects of the present invention, the compound represented by the formula (1) is preferably not substituted with an ionic substituent such as a sulfo group or a carboxyl group.

According to another embodiment, the azo compound represented by the formula (4) is such that $A_1$ represents any one of the formulae (A-17), (A-18), (A-20), (A-22) to (A-24), (A-27), (A-28), (A-31) and (A-32).

It is also preferable that the azo compound represented by the formula (4) be represented by the following formula (6):

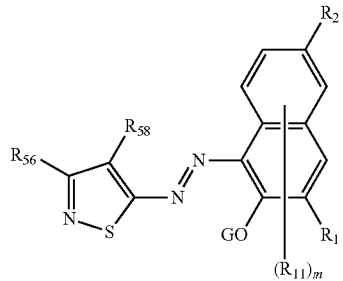

(6)

wherein in the formula (6), G, $R_1$, $R_2$, $R_{11}$, $R_{56}$, $R_{58}$ and m have the same meanings as G, $R_1$, $R_2$, $R_{11}$, $R_{56}$, $R_{58}$ and m defined in the formula (4); and $R_{56}$ and $R_{58}$ may be bonded to each other to form a 5-membered or 6-membered ring.

The substituents for G, $R_1$, $R_2$, $R_{11}$, $R_{56}$, $R_{58}$ and m of the compound represented by the formula (6) have the same preferred ranges as the substituents for the formula (4).

The present invention also includes the tautomers of the azo compounds represented by formula (1), formula (4), formula (5) and formula (6). The formula (1), formula (4), formula (5) and formula (6) are each indicated in the form of the extreme structure among the various kinds of tautomers that can be adopted by the chemical structure; however, tautomers having structures other than the described structures may also be used, or a mixture containing plural tautomers may also be used.

The present invention also includes an azo compound represented by the following formula (1'), which is a tautomer of the azo compound represented by the formula (1), in the scope of the invention.

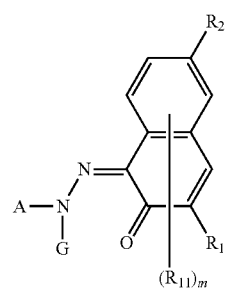

(1')

wherein in the formula (1'), A, G, $R_1$, $R_2$, $R_{11}$ and m have the same meanings as A, G, $R_1$, $R_2$, $R_{11}$ and m defined in the formula (1).

Furthermore, according to the present invention, the azo compound represented by the formula (1) preferably has a substituent which forms intramolecular hydrogen bonding or intramolecular cross-hydrogen bonding. The azo compound more preferably has a substituent which forms at least one or more intramolecular hydrogen bonds, and particularly preferably has a substituent which forms at least one or more intramolecular cross-hydrogen bonds.

The reason why this structure is preferred is that the nitrogen atom constituting the heterocyclic group contained in the azo compound structure, the hydrogen atom and oxygen atom of the hydroxyl group of the naphthalene substituent, and the nitrogen atom of the azo group or a hydrazone group, which is a tautomer of an azo group; or the hydrogen atom and oxygen atom of the carbonyl group substituted in the azo compound or the hydroxyl group of the naphthalene substituent, and the nitrogen atom of the azo group or a hydrazone group, which is a tautomer of an azo group, are likely to easily form intramolecular cross-hydrogen bonding.

As a result, planarity of the molecule increases, the intramolecular/intermolecular interaction is enhanced, and crystallinity of the azo compound increases (more likely to form a higher-order structure). Thus, light fastness, thermal stability, wet thermal stability, water resistance, gas resistance and/or solvent resistance, which also constitute the performance required in pigments, are also enhanced to a large extent, which is more preferable.

In the formula (2), $R_3$ represents an amino group, or an aliphatic oxy group. In the formula (3), $X_1$ represents —S— or —NR—, and R represents a hydrogen atom or an aliphatic group. In the formula (1), G is preferably a hydrogen atom.

The azo compounds represented by the formula (1), formula (4), formula (5) and formula (6) of the present invention may be tautomers thereof, salts thereof, or hydrates thereof.

Furthermore, the present invention also relates to a printing ink, a coating material, a dye and a resist ink, which all contain the azo compound of the present invention described above.

The printing ink, coating material and resist ink of the present invention may contain a resin and/or a liquid medium, if necessary. The resin is not particularly limited because any resin that has been conventionally used in various applications such as the various inks and coating materials described above can all be used. The liquid medium may be water or an organic solvent, and is not particularly limited because any liquid medium that has been conventionally used can be used.

Furthermore, the azo compounds represented by the formula (1), formula (4), formula (5) and formula (6) of the present invention are useful as azo pigments.

<Azo Pigment>

A pigment is in a state in which molecules are firmly bonded to each other by the aggregation energy caused by strong interaction between colorant molecules. It is described in, for example, Journal of the Imaging Society of Japan, Vol. 43, p. 10 (2004) and the like that achieving this state requires van der Waals force between molecules and hydrogen bonding between molecules.

As a method of strengthening the van der Waals force between molecules, a method of introducing an aromatic group, a polar group and/or a heteroatom to the molecules may be considered. Furthermore, as a method of forming hydrogen bonding between molecules, a method of introducing a substituent containing a hydrogen atom bonded to a heteroatom into the molecules, and/or a method of introducing an electron-donating substituent into the molecules may be considered. Further, it is believed that higher overall polarity of the molecules is preferred. For this purpose, for example, it is thought that a group having a shorter chain length, such as an alkyl group, is preferred, and a smaller value of the ratio of the molecular weight/number of azo groups is preferred.

From this point of view, it is preferable that pigment molecules contain an amide bond, a sulfonamide bond, an ether bond, a sulfone group, an oxycarbonyl group, an imide group, a carbamoylamino group, a heterocyclic ring, a benzene ring and the like.

The azo compound of the present invention is represented by the formula (1), formula (4), formula (5) or formula (6).

The compound represented by the formula (1) can easily form intermolecular interaction between colorant molecules due to the particular structure of the compound, has low solubility in water or organic solvents, and can be used as an azo pigment.

A pigment is different from a dye which is used by being dissolved in water or an organic solvent in a molecular dispersion state, and a pigment is used by being finely dispersed as sliding particles such as molecular aggregates in a solvent.

Furthermore, since the compound has a particular structure represented by the formula (1), the compound exhibits excellent characteristics in terms of chromatic characteristics such as tinctorial strength and hue, and can also exhibit excellent characteristics in terms of durability such as light fastness and heat resistance.

In the present invention, a tautomer of the azo compound represented by the formula (1), a salt or hydrate of the azo compound or the tautomer may also be used as an azo pigment.

Now, specific examples of the azo compound represented by the formula (1), which can be suitably used as azo pigments, will be listed below, but the examples are not limited to the following examples. Furthermore, the structures of the following specific examples are indicated in the form of extreme structures among various kinds of tautomers that can be adopted by the chemical structure, but a tautomeric structure other than the structures described below may also be used.

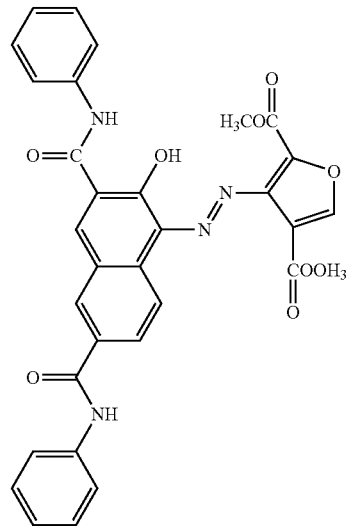

D-1

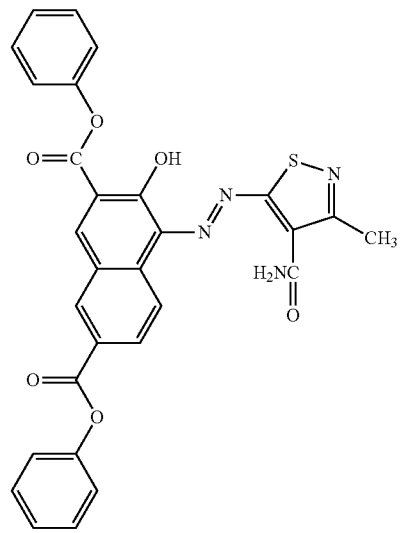

D-2

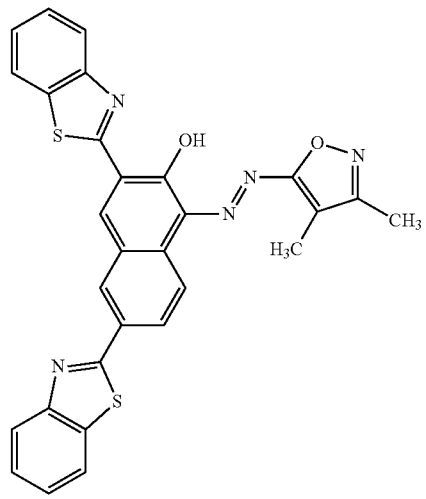

D-3

-continued
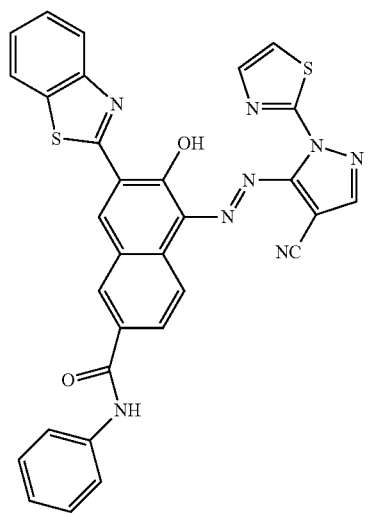 D-4
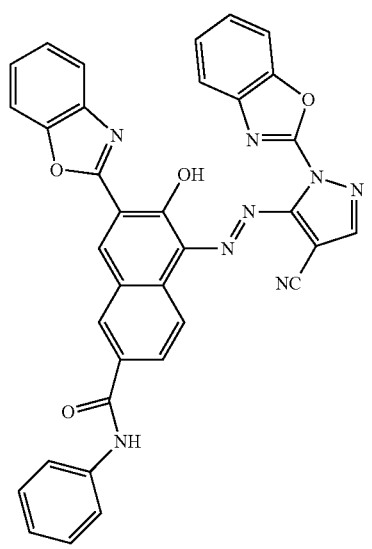 D-5
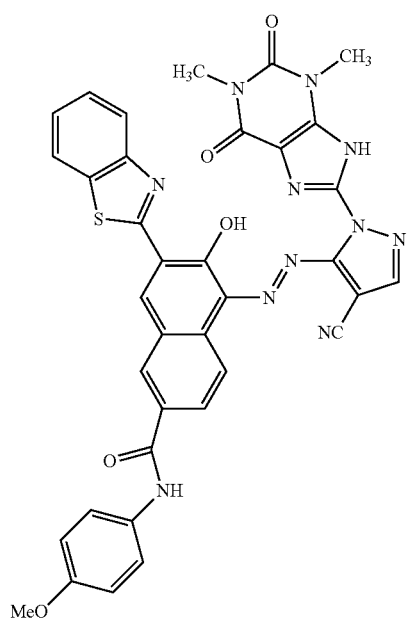 D-6
-continued
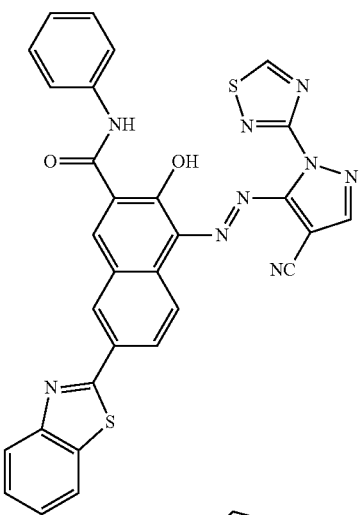 D-7
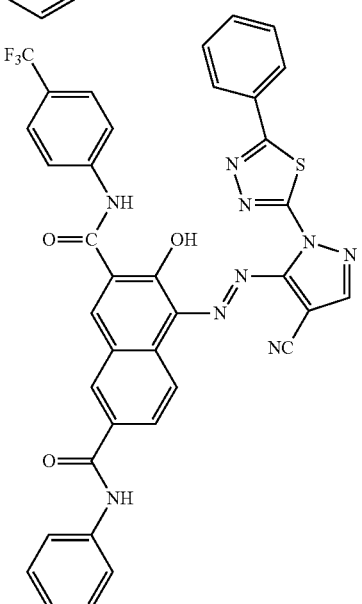 D-8
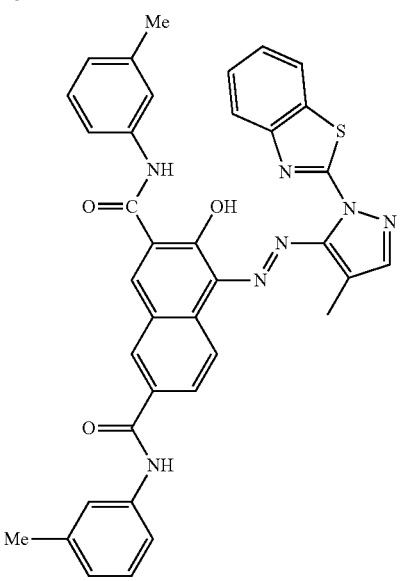 D-9

-continued
D-10
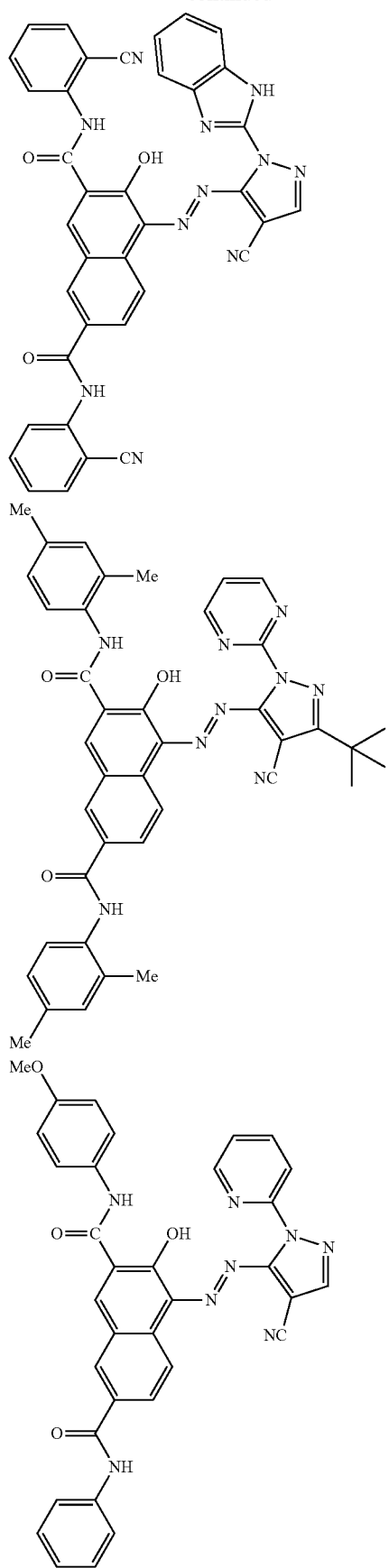
D-11
D-12
-continued
D-13
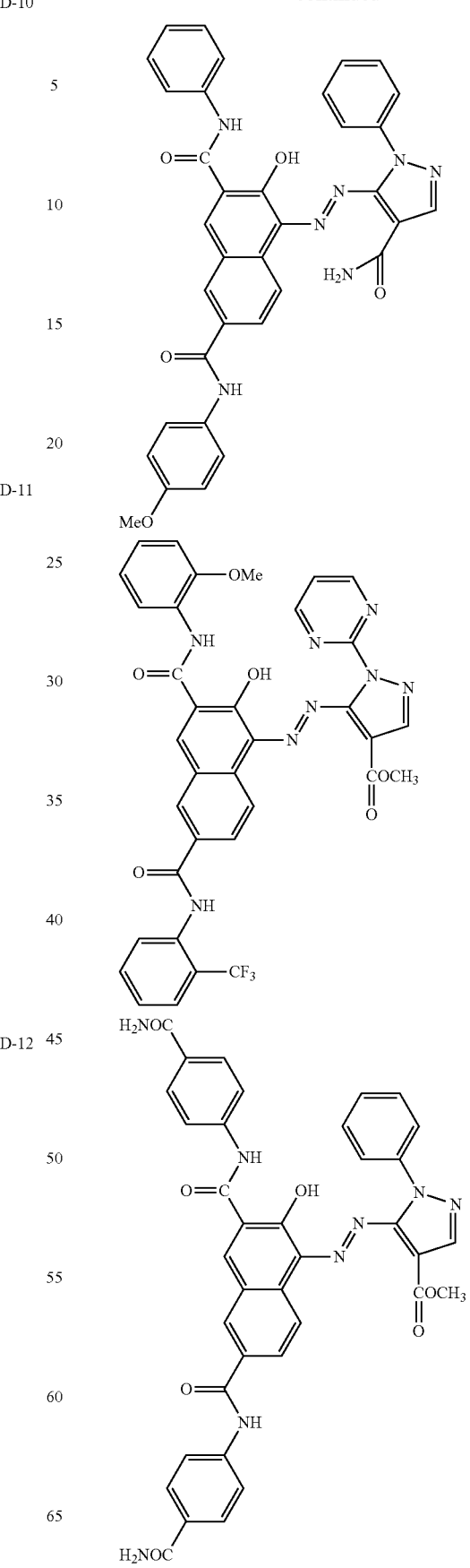
D-14
D-15

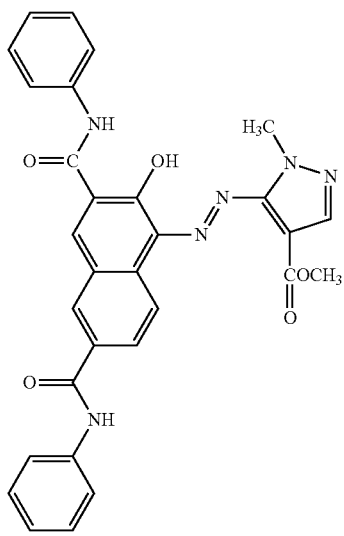
D-16
D-17
D-18
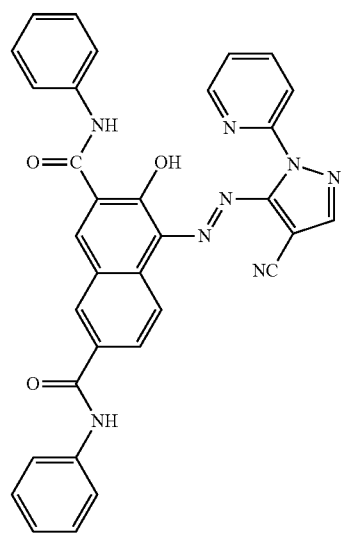
D-19
D-20
D-21

-continued
D-22
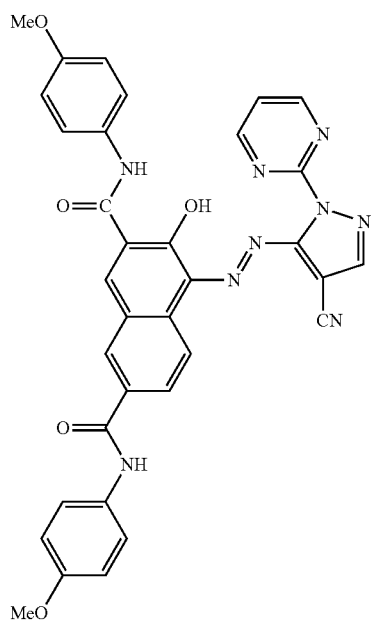
D-23
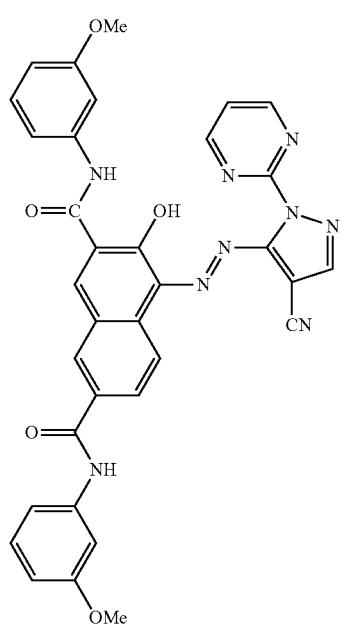
D-24
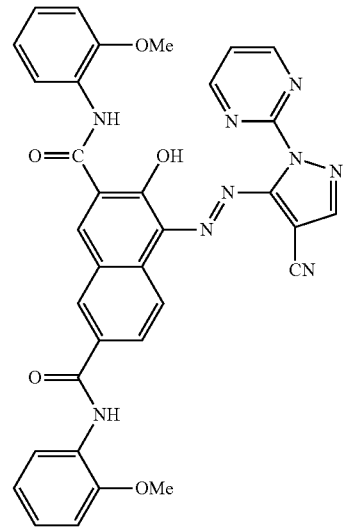
D-25
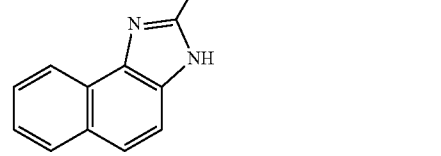
D-26
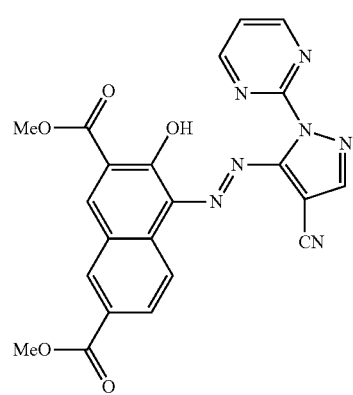

-continued
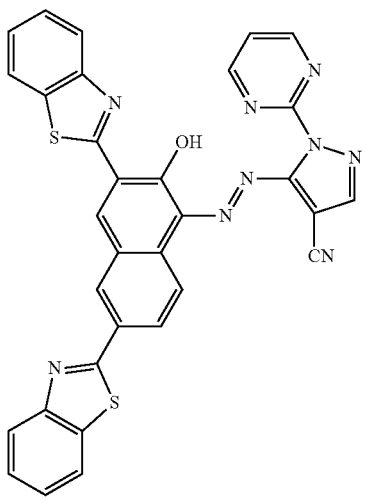
D-27
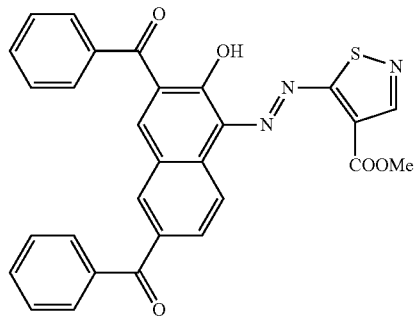
D-30
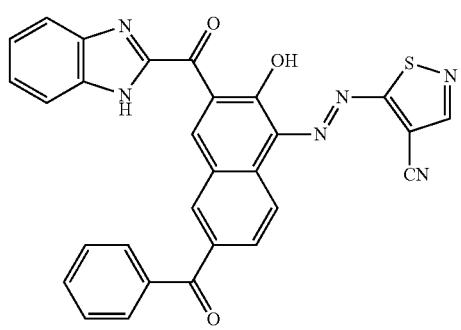
D-31
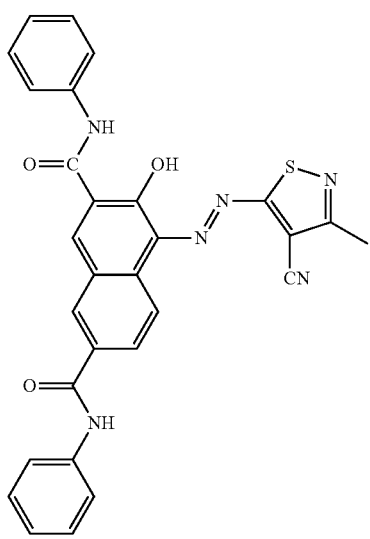
D-28
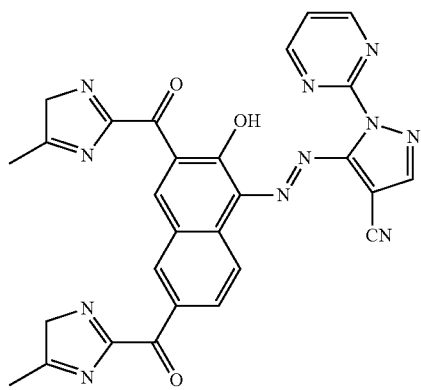
D-32
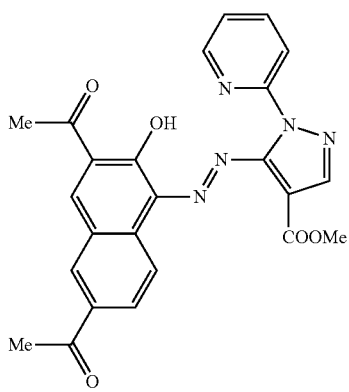
D-29
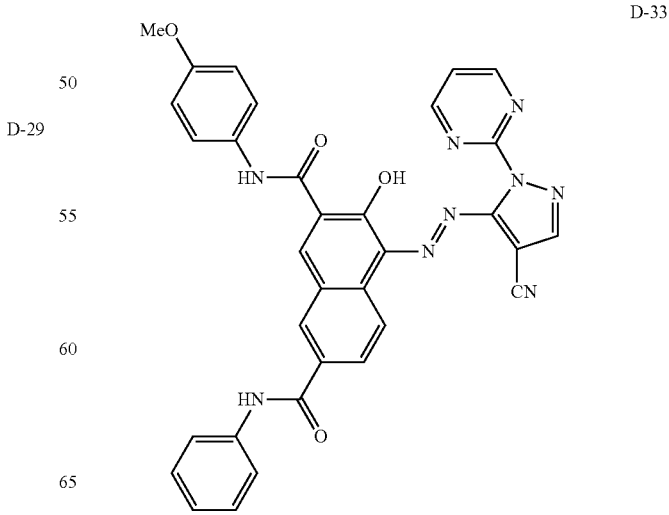
D-33

The compound represented by the formula (1) of the present invention may be such that the chemical structure may be formula (1) or a tautomer thereof, or the compound of the formula (1) may be a compound of any crystal form called a polymorph.

Crystal polymorphism means that compounds have the same chemical composition but have different configurations of the building blocks (molecules or ions) in the crystal. The chemical and physical properties are determined based on the crystal structure, and the respective polymorphs can be distinguished by rheological properties, color, and other color chromatic characteristics. Furthermore, different polymorphs can also be confirmed by X-ray diffraction (powder X-ray diffraction analysis results) or X-ray analysis (X-ray crystallographic analysis results).

When crystal polymorphs are present in the compound represented by the formula (1) of the present invention, any polymorph may be used, and a mixture of two or more kinds of polymorphs may also be used. However, a compound having a single crystal form as a main component is preferred. That is, crystal polymorphs are preferably not present as a mixture, and the content of the azo compound having a single crystal form is 70% to 100%, preferably 80% to 100%, more preferably 90% to 100%, even more preferably 95% to 100%, and particularly preferably 100%, based on the entirety of the azo compound. When an azo compound having a single crystal form is contained as a main component, regularity in the configuration of colorant molecules is increased, the intramolecular/intermolecular interaction is strengthened, and a three-dimensional network of higher order can be easily formed. As a result, the performance required from a pigment, such as hue, light fastness, heat fastness, moisture fastness, fastness to oxidizing gases, and solvent resistance, can be enhanced.

The mixing ratio of crystal polymorphs in the azo compound can be checked from the physicochemical analyses of solids, such as single crystal X-ray crystallographic analysis, powder X-ray diffraction (XRD), microscopic photography of crystals (TEM), and IR (KBr method).

The control of tautomerism and/or crystal polymorphism as described above can be achieved by the production conditions used in the coupling reaction.

Furthermore, according to the present invention, the azo compound represented by the formula (1) is such that when the azo compound has acid groups, a part or all of the acid groups may be in a salt form, or compounds in a salt form and compounds in a free acid form may be present in mixture. Examples of the salt form include salts of alkali metals such as Na, Li and K; salts of ammonium which may be substituted with an alkyl group or a hydroxyalkyl group; and salts of organic amines. Examples of the organic amines include lower alkylamines, hydroxy-substituted lower alkylamines, carboxy-substituted lower alkylamines, and polyamines having 2 to 10 alkyleneimine units each having 2 to 4 carbon atoms. In the case of these salt forms, the salt type is not limited to one kind, but a mixture of plural kinds may also be used.

Furthermore, in the structure of the compound used in the present invention, when plural acid groups are contained in one molecule of the compound, the plural acid groups may be in a salt form or an acid form, and different groups may be in different forms.

According to the present invention, the azo compound represented by the formula (1) may be a hydrate containing water molecules in the crystals.

Next, the method for producing the azo compound represented by the formula (1) will be described.

The compound represented by the formula (1) can be obtained by subjecting an amine compound corresponding to A in the formula (1) and a compound corresponding to the naphthalene moiety to a diazo coupling reaction.

For example, a heterocyclic amine compound represented by A-NH$_2$ (wherein A represents A in the formula (1)) is diazotization in non-aqueous acidity. This and a compound represented by the following formula (1″) (wherein G, R$_1$, R$_2$, R$_{11}$ and m respectively have the same meanings as G, R$_1$, R$_2$, R$_{11}$ and m defined in the formula (1)) are subjected to a coupling reaction in an acidic state, and the resultant product is subjected to a post-treatment according to a routine method. Thus, the azo compound represented by the formula (1) of the present invention can be produced.

The heterocyclic amine corresponding to the amino body of A of the formula (1) may be available as commercial products, but in general, the heterocyclic amine can be produced by a conventionally known method, for example, a method described in JP 4022271B.

The coupler represented by the formula (1″) may be available as commercial products, but can also be produced by a method described in JP 4515384B or a method equivalent thereto.

The diazotization reaction of the heterocyclic amine represented by the above reaction scheme can be carried out by, for example, performing the reaction at a temperature of 15° C. or lower for about 10 minutes to 6 hours, using reagents such as sodium nitrite, nitrosyl sulfate or isoamyl nitrite in an acidic solvent such as sulfuric acid, phosphoric acid or acetic acid.

The coupling reaction can be carried out by subjecting the diazonium salt obtained by the method described above and a compound represented by the formula (1″) to a reaction at or below 40° C., and preferably at or below 25° C., for about 10 minutes to 12 hours.

The reaction product thus obtained may be precipitated as crystals; however, in general, water or an alcohol-based solvent is added to the reaction liquid, crystals are caused to precipitate out, and the crystals can be collected by filtration. Furthermore, an alcohol-based solvent, water or the like is added to the reaction liquid to precipitate out crystals, and the precipitated crystals can be collected by filtration. The filtered crystals may be washed and dried as necessary, and thus the azo compound (for example, azo pigment) represented by the formula (1) can be obtained.

A compound represented by the formula (1) can be usually obtained as a crude azo compound (crude) by the production method described above, and particularly, in the case of using the compound as the azo pigment of the present invention, it is preferable to perform a post-treatment. Examples of this post-treatment include pigment particle control processes by means of milling treatments such as solvent salt milling, salt milling, dry milling, solvent milling and acid pasting, a solvent heating treatment, or the like; and surface treatment processes by means of resins, surfactants and dispersants.

For the azo compound (for example, azo pigment) represented by the formula (1) of the present invention, it is preferable to perform a solvent heating treatment and/or solvent salt milling as the post-treatment.

Examples of the solvent used in the solvent heating treatment include water; aromatic hydrocarbon-based solvents such as toluene and xylene; halogenated hydrocarbon-based solvents such as chlorobenzene and o-dichlorobenzene; alcohol-based solvents such as isopropanol and isobutanol; aprotic polar organic solvents such as N,N-dimethylformamide, N,N-dimethylacetamide, and N-methyl-2-pyrrolidone; glacial acetic acid, pyridine, and mixtures thereof. An inorganic or organic acid or base may be further added to the solvents listed above. The temperature of the solvent heating treatment may vary with the desired primary particle size of the pigment, but the temperature is preferably 40° C. to 150° C., and more preferably 60° C. to 100° C. The process time is preferably 30 minutes to 24 hours.

The solvent salt milling process may be carried out by, for example, introducing the crude azo compound, an inorganic salt, and an organic solvent which does not dissolve the azo compound and the salt into a kneading machine, and performing kneading and grinding therein. A water-soluble inorganic salt can be suitably used as the inorganic salt, and for example, it is preferable to use an inorganic salt such as sodium chloride, potassium chloride, or sodium sulfate. Furthermore, it is more preferable to use an inorganic salt having an average particle size of 0.5 μm to 50 μm. The amount of use of the inorganic salt is preferably set to 3 to 20 times, and more preferably 5 to 15 times, the mass of the crude azo compound. As the organic solvent, a water-soluble organic solvent can be suitably used, and since the temperature elevation at the time of kneading causes the solvent to be easily evaporable, a high boiling point solvent is preferred in view of safety. Examples of such an organic solvent include diethylene glycol, glycerin, ethylene glycol, propylene glycol, liquid polyethylene glycol, liquid polypropylene glycol, 2-(methoxymethoxy) ethanol, 2-butoxyethanol, 2-(isopentyloxy)ethanol, 2-(hexyloxy)ethanol, diethylene glycol monomethyl ether, diethylene glycol monoethyl ether, diethylene glycol monobutyl ether, triethylene glycol, triethylene glycol monomethyl ether, 1-methoxy-2-propanol, 1-ethoxy-2-propanol, dipropylene glycol, dipropylene glycol monomethyl ether, dipropylene glycol monomethyl ether, dipropylene glycol, and mixtures thereof. The use amount of the water-soluble organic solvent is preferably 0.1 to 5 times the mass of the crude azo compound. The kneading temperature is preferably 20° C. to 130° C., and particularly preferably 40° C. to 110° C. As the kneading machine, for example, a kneader or a mix-muller can be used.

[Coloring Composition]

The coloring composition of the present invention means a coloring composition containing at least one kind of the azo pigment of the present invention described above. The coloring composition of the present invention may contain a medium, but when a solvent is used as the medium, the coloring composition is suitable as a color composition for color filters or an ink for inkjet recording in particular, and is particularly suitable as a coloring composition for color filters. The coloring composition of the present invention can be prepared by using an oleophilic medium or an aqueous medium as the medium, and dispersing the azo pigment of the present invention therein. It is preferable to use an aqueous medium. The coloring composition of the present invention also includes an ink composition in which a medium is excluded. The coloring composition of the present invention may contain other additives as necessary, to the extent that the effects of the present invention are not impaired. Examples of the other additives include known additives (described in JP 2003-306623A) such as a drying preventing agent (moisturizing agent), a discolorization preventing agent, an emulsion stabilizer, a penetration enhancer, an ultraviolet absorbent, an antiseptic, an antimicrobial, a pH adjusting agent, a surface tension adjusting agent, a defoamant, a viscosity adjusting agent, a dispersant, a dispersion stabilizer, an anti-rust agent, and a chelating agent. In the case of a water-soluble ink, these various additives are added directly to the ink liquid. In the case of an oil-soluble ink, it is common to prepare an azo pigment dispersion and then to add the additives to the dispersion. However, the additives may also be added to the oil phase or the aqueous phase during the preparation.

[Coloring Composition for Color Filters]

The coloring composition for color filters of the present invention contains an azo pigment. The coloring composition for color filters of the present invention (hereinafter, may be referred simply as a coloring composition) means a coloring composition containing at least one kind of the azo pigment of the present invention described above.

The coloring composition of the present invention preferably further contains a polymerizable compound and a solvent.

Furthermore, when the coloring composition of the present invention is prepared, the azo pigment obtained as described above may be incorporated directly, or may be incorporated as a pigment dispersion in which the azo pigment is dispersed in a solvent. When the azo pigment is prepared into a pigment dispersion, the chromatic characteristics, durability, dispersion stability, light fastness and weather resistance become excellent, which is preferable.

The use amount of the azo pigment of the present invention described above (the total amount of pigments used in the case of using another pigment in combination) in the coloring composition of the present invention is preferably 0.01 parts to 2 parts by mass, and particularly preferably 0.1 parts to 1 part by mass, relative to 1 part by mass of the polymerizable compound.

[Polymerizable Compound]

The polymerizable compound may be appropriately selected in consideration of the production process for color filters. The polymerizable compound may be a photosensitive compound and/or a thermosetting compound, but a photosensitive compound is particularly preferred.

As the photosensitive compound, at least one or more are selected from a photopolymerizable resin, a photopolymerizable monomer and a photopolymerizable oligomer, and the photosensitive compound is preferably a compound having an ethylenically unsaturated bond. The coloring composition for color filters may contain a compound which turns into a resin in a cured state, and the coloring composition includes the case where only a photosensitive compound which does not turn into a resin in an uncured state is included.

Examples of the photopolymerizable compound, photopolymerizable monomer and photopolymerizable oligomer include (meth)acrylic acid esters such as 2-hydroxyethyl (meth)acrylate, 2-hydroxypropyl (meth)acrylate, 2-ethylhexyl (meth)acrylate, ethylene glycol di(meth)acrylate, diethylene glycol di(meth)acrylate, triethylene glycol di(meth)acrylate, polyethylene glycol di(meth)acrylate, pentaerythritol di(meth)acrylate, dipentaerythritol tetra(meth)acrylate, dipentaerythritol hexa(meth)acrylate, bisphenol A type epoxy di(meth)acrylate, bisphenol F type epoxy di(meth)acrylate, and bisphenol-fluorene type epoxy di(meth)acrylate. Further examples include vinyl resins such as acrylic acid (co)polymers, (meth)acrylic acid (co)polymers, and maleic acid (co)polymers; and resins having ethylenic double bonds in the side chains such as polyethylene oxide, polyvinylpyrrolidone, polyamides, polyurethane, polyethers, and polyesters. These may be used individually, or two or more kinds may be used in combination.

The incorporation ratio of the polymerizable compound is preferably 40% to 95% by mass, and more preferably 50% to 90% by mass, relative to the total solids content of the coloring composition for color filters. Other resins and the like can be incorporated into the composition as necessary, but in this case, it is preferable that the total amount of other combined resins be included in the range described above. Meanwhile, the total solids content means the components remaining as solids after drying and curing, and does not include the solvent, but includes monomers.

[Photopolymerization Initiator]

In the case of using a photosensitive compound as the polymerizable compound, a photopolymerization initiator is used together with the photosensitive compound (for example, a monomer and/or an oligomer). The photopolymerization initiator may be one or more selected from compounds such as oxime derivatives, benzophenone derivatives, acetophenone derivatives, benzoin derivatives, benzoin ether derivatives, thioxanthone derivatives, anthraquinone derivatives, naphthoquinone derivatives, and triazine derivatives. A known photosensitizer may also be used together with these photopolymerization initiators.

Particularly preferred specific examples of oxime derivatives include 2-(O-benzoyloxime)-1-[4-(phenylthio)phenyl]-1,2-octanedione, and 1-(0-acetyloxime)-1-[9-ethyl-6-(2-methylbenzoyl)-9H-carbazol-3-yl]ethanone. Examples of these oxime derivatives include CGI-124 and CGI-242 (all manufactured by BASF Corp.).

Examples of the thermosetting compound include thermosetting resins such as melamine resins, urea resins, alkyd resins, epoxy resins, phenolic resins, and cyclopentadiene resins.

Together with the photosensitive compound and/or thermosetting compound described above, a binder resin having an acidic group and a resin that is generally used in inks, such as an acrylic resin or a urethane resin, may also be used as other polymerizable compounds.

[Solvent]

The pigment dispersion may be an aqueous system or a non-aqueous system, but the pigment dispersion may be varied depending on the color filter production method. For example, a non-aqueous system is preferred in a photolithographic method, while any system may be used in an inkjet method.

Examples of the solvent used in the coloring composition of the present invention include fatty acid esters such as ethyl acetate, butyl acetate, ethylene glycol monomethyl ether acetate, and propylene glycol monomethyl ether acetate (PGMEA; also known as 1-methoxy-2-acetoxypropane); ketones such as acetone, methyl ethyl ketone, methyl isobutyl ketone, cyclohexanone, and diacetone alcohol; aromatics such as benzene, toluene and xylene; alcohols such as methanol, ethanol, n-propanol, isopropanol, and n-butanol; glycols such as ethylene glycol, diethylene glycol, triethylene glycol, tetraethylene glycol, polyethylene glycol, propylene glycol, dipropylene glycol, tripropylene glycol, polypropylene glycol, trimethylene glycol, and hexanetriol; glycerin; alkylene glycol monoalkyl ethers such as ethylene glycol monomethyl ether, ethylene glycol monoethyl ether, diethylene glycol monomethyl ether, diethylene glycol monoethyl ether, propylene glycol monomethyl ether (PGME; also known as 1-methoxy-2-propanol), and propylene glycol monoethyl ether; alkylene glycol dialkyl ethers such as triethylene glycol dimethyl ether, triethylene glycol diethyl ether, tetraethylene glycol dimethyl ether, and tetraethylene glycol diethyl ether; ethers such as tetrahydrofuran, dioxane, and diethylene glycol diethyl ether; alkanolamines such as monoethanolamine, diethanolamine, and triethanolamine; nitrogen-containing polar organic solvents such as N,N-dimethylformamide, N,N-dimethylacetamide, N-methyl-2-pyrrolidone, 2-pyrrolidone, and 1,3-dimethyl-2-imidazolidinone; and water.

The solvent is preferably an aliphatic ester.

Among these solvents, a water-soluble solvent may be mixed with water, and the mixture may be used as an aqueous medium. Also, two or more kinds selected from the solvents described above, except water, may be mixed and used as an oily medium.

The azo pigment prepared into a pigment dispersion acquires excellent light fastness or weather resistance, as compared with azo pigments that are not prepared into pigment dispersions.

The coloring composition of the present invention may contain two or more kinds of the azo pigment of the present invention described above.

Furthermore, other kinds of pigments, for example, one or more pigments selected from azo-based pigments, disazo-based pigments, benzimidazolone-based pigments, condensed azo-based pigments, azo lake-based pigments, anthraquinone-based pigments, diketopyrrolopyrrole-based pigments, quinacridone-based pigments, isoindoline-based pigments, isoindolinone-based pigments, perinone-based pigments and perylene-based pigments, or derivatives thereof may also be used together with the azo pigment of the present invention described above, to the extent that the purpose of the present invention is not impaired.

The pigment that may be used in combination in the present invention is not particularly limited. Specific examples include the compounds classified as pigments in the Color Index (C.I.: published by The Society of Dyers and Colourists), that is, compounds to which Color Index (C.I.) numbers such as shown below are assigned.

Examples include yellow pigments such as C.I. Pigment Yellow 1, C.I. Pigment Yellow 3, C.I. Pigment Yellow 12, C.I. Pigment Yellow 13, C.I. Pigment Yellow 83, C.I. Pigment Yellow 138, C.I. Pigment Yellow 139, C.I. Pigment Yellow 150, C.I. Pigment Yellow 180, and C.I. Pigment Yellow 185; red pigments such as C.I. Pigment Red 1, C.I. Pigment Red 2, C.I. Pigment Red 3, C.I. Pigment Red 177, and C.I. Pigment Red 254; blue pigments such as C.I. Pigment Blue 15, C.I. Pigment Blue 15:3, C.I. Pigment Blue 15:4, and C.I. Pigment Blue 15:6; green pigments such as C.I. Pigment Green 7, C.I. Pigment Green 36, and C.I. Pigment Green 58; and violet pigments such as C.I. Pigment Violet 23 and C.I. Pigment Violet 23:19.

Furthermore, inorganic pigments such as titanium oxide, barium sulfate, calcium carbonate, zinc nitrate, lead sulfate, yellow lead, zinc yellow, rouge (red iron(III) oxide), cadmium red, ultramarine blue, Prussian blue, chromium oxide green, cobalt green, amber, titanium black, synthetic iron black, and carbon black may also be used in combination. The pigment according to the present invention can be used individually, or two or more kinds can be used as a mixture.

In the case of using another pigment other than the azo pigment of the present invention described above in combination, the content is preferably 50% by mass or less, and particularly preferably 20% by mass or less, relative to the total mass of the pigment in the coloring composition.

Meanwhile, in the present specification, the term "azo pigment of the present invention" is used to mean one kind of the azo compound represented by the formula (1) as well as a combination of two or more kinds of the azo compound represented by the formula (1), and a combination of the azo compound represented by the formula (1) and another pigment.

[Pigment Dispersion (1)]

The pigment dispersion is preferably obtained by dispersing the azo pigment described above and an aqueous or non-aqueous medium using a dispersing apparatus. Examples of the dispersing apparatus that can be used include a simple stirrer or impeller-stirring system, an in-line stirring system, a mill system (for example, a colloid mill, a ball mill, a sand mill, a bead mill, an attritor, a roll mill, a jet mill, a paint shaker, and an agitator mill), an ultrasonication system, a high pressure emulsification dispersion system (high pressure homogenizer; specific commercially available apparatuses include a Gaulin homogenizer, a microfluidizer, DeBEE 2000, and the like).

According to the present invention, the volume average particle size of the pigment is preferably equal to or greater than 10 nm and equal to or less than 250 nm. Meanwhile, the volume average particle size of the pigment particles means the particle size of the pigment itself, or in the case where additive substances such as a dispersant are adhering to the pigment, the volume average particle size means the size of the particles to which the additive substances are attached. According to the present invention, a NanoTrack UPA particle size distribution analyzer (UPA-EX150; manufactured by Nikkiso Co., Ltd.) was used as the analyzer for the volume average particle size of the pigment. The measurement was carried out according to a predetermined measurement method, by placing 3 ml of a pigment dispersion in a measurement cell. Meanwhile, as the parameter to be input at the time of analysis, an ink viscosity was used as the viscosity, and a pigment density was used as the density of dispersed particles.

A more preferred volume average particle size is from 20 nm to 250 nm, and more preferably from 30 nm to 230 nm. If the volume average particle size of the particles in the pigment dispersion is less than 20 nm, there may be instances in which storage stability cannot be secured, and if the volume average particle size is greater than 250 nm, there may be instances in which the optical density is lowered.

The concentration of the pigment contained in the pigment dispersion of the present invention is preferably in the range of 1% to 35% by mass, and more preferably in the range of 2% to 25% by mass. When the pigment concentration is in the range described above, the properties of the dispersion such as surface tension and viscosity can be easily adjusted, which is preferable.

The azo pigment of the present invention is used after the properties such as solvent resistance, dispersibility and heat transfer properties are adjusted by means of substituents, to be appropriate for the applications. Furthermore, the azo pigment of the present invention can be used in an emulsified dispersion state, or in a solid dispersion state, in accordance with the system used.

Furthermore, a dispersant may also be incorporated into the composition in order to satisfactorily disperse the components in a short time.

It is preferable that the coloring composition for color filters according to the present invention further contain one or more dispersants selected from a surfactant, a silicone-based additive, a pigment-based additive, a silane-based coupling agent, and a titanium-based coupling agent. These dispersants may be used in combination of two or more kinds.

Specific examples of the dispersants described above will be described below.

Any surfactant having a surface active action may be used without particular limitations, but cationic, anionic, nonionic or amphoteric surfactants may be used. Specific examples thereof include anionic surfactants such as alkanesulfonates, linear alkylbenzenesulfonates, branched alkylbenzenesulfonates, alkylnaphthalenesulfonates, naphthalenesulfonate-formaldehyde condensates, alkylsulfates, polyoxyethylene alkyl ether sulfates, alkylphosphates, polyoxyethylene alkyl ether phosphates, and aliphatic monocarboxylates; cationic surfactants such as alkylamine salts, and quaternary amine salts; nonionic surfactants such as glycerin fatty acid esters, sorbitan fatty acid esters, polyoxyethylene alkyl ethers, polyoxyethylene alkyl phenyl ethers, polyethylene glycol fatty acid esters, and polyoxyethylene sorbitan fatty acid esters; amphoteric surfactants such as alkylbetaines; and polymeric surfactants which may be any of cationic, anionic, nonionic and amphoteric.

Specific examples of the silicone-based additives include polyalkylsiloxane, polyalkylphenylsiloxane, polyorganosiloxane, polydimethylsiloxane, polyorganosiloxane polyether copolymers, polyfluorosiloxane, and organosilanes. These silicone-based additives may be used in combination of two or more kinds.

A pigment-based additive is a pigment derivative in which a substituent such as a basic group, an acidic group, a linear alkyl group, a branched alkyl group, or a polyoxyethylene group is introduced into a pigment skeleton. Preferred examples of the pigment skeleton include monoazo-based pigments, disazo-based pigments, benzimidazolone-based pigments, condensed azo-based pigments, azo lake-based pigments, anthraquinone-based pigments, diketopyrrolopyrrole-based pigments, quinacridone-based pigments, isoindoline-based pigments, isoindolinone-based pigments, perinone-based pigments, and perylene-based pigments.

Among these pigment-based additives, compounds in which a substituent such as described above is introduced into the skeleton of an azo-based pigment have good affinity to the azo compound represented by the formula (1), which is preferable.

Specific examples of the silane-based coupling agent include vinyltrimethoxysilane, vinyltriethoxysilane, vinyltris(β-methoxyethoxy)silane, β-(3,4-epoxycyclohexyl)ethyltrimethoxysilane, γ-glycidoxypropyltrimethoxysilane, γ-glycidoxypropylmethyldiethoxysilane, γ-aminopropyltriethoxysilane, N-phenyl-γ-aminopropyltrimethoxysilane, γ-methacryloxypropyltrimethoxysilane, vinyltriacetoxysilane, methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, n-butyltrimethoxysilane, isobutyltrimethoxysilane, trimethylmethoxysilane, hydroxypropyltrimethoxysilane, n-hexadecyltrimethoxysilane, and n-octadecyltrimethoxysilane.

Specific examples of the titanium-based coupling agent include isopropyltri(N-aminoethylaminoethyl)titanate, and dibutoxybistriethanolamine titanate.

The use amount of the dispersant described above may vary depending on the type of the dispersant used, but it is preferable to use the dispersant in an amount of 0.1 parts to 100 parts by mass, and particularly preferably 0.5 parts to 80 parts by mass, relative to 100 parts by mass of the azo compound represented by the formula (1).

The method of using the dispersant is not particularly limited, and a method for preparing a known coloring composition for photolithographic methods may be used.

The present invention also relates to the method for preparing a coloring composition for color filters. The method for preparing a coloring composition for color filters of the present invention includes a step of dispersing one or more dispersants selected from a surfactant, a silicone-based additive, a pigment-based additive, a silane-based coupling agent, and a titanium-based coupling agent, and an azo compound represented by the formula (1) in a portion of a solvent to obtain a pigment dispersion; and a step of mixing the pigment dispersion with a polymerizable compound and the remaining solvent.

As the method for preparing a coloring composition for color filters, it is preferable to use the method of the present invention.

The present invention also provides a color filter that is formed by using the coloring composition for color filters described above. The color filter exhibits high contrast and satisfactory light transmissivity. Specifically, the color filter exhibits light transmissivity of preferably 85% or higher, and more preferably 90% or higher, to the wavelength of 650 nm.

In order to produce a color filter of the present invention, any known method may be used, and suitably, a photolithographic method and an inkjet method may be used. Hereinafter, a photolithographic method and an inkjet method will be described in detail.

1) Photolithographic Method

In the case of forming a color filter by a photolithographic method, a photosensitive compound is used as the polymerizable compound of the coloring composition for color filters of the present invention. The photosensitive compound is incorporated as a monomer and/or an oligomer into the coloring composition together with a photopolymerization initiator, and is cured by light irradiation, thereby forming a film on a transparent substrate.

As the photosensitive compound, a polymerizable monomer having one or more ethylenic double bonds, or a polymer or copolymer thereof (here, this polymer or copolymer has ethylenic double bonds) is suitably used.

Such a photosensitive compound (polymerizable monomer) is preferably an acrylic acid ester or a methacrylic acid ester in particular, and specific examples thereof include methyl acrylate, methyl methacrylate, butyl methacrylate, butyl acrylate, pentaerythritol tetraacrylate, pentaerythritol tetramethacrylate, pentaerythritol triacrylate, pentaerythritol trimethacrylate, dipentaerythritol hexaacrylate, dipentaerythritol hexamethacrylate, dipentaerythritol pentaacrylate, dipentaerythritol pentamethacrylate, glycerol diacrylate, glycerol dimethacrylate, 1,4-butanediol diacrylate, 1,4-butanediol dimethacrylate, bisphenol A diacrylate, and bisphenol A dimethacrylate.

In the case of using a photolithographic method, a binder resin having an acidic group is used in addition to the photosensitive compound described above, in the coloring composition of the present invention. Examples of the binder resin having an acidic group include resins having a carboxyl group, a hydroxyl group, a sulfonic acid group and the like, and a binder resin having a carboxyl group and/or a hydroxyl group is preferred.

As the binder resin having an acidic group described above, a copolymer of a monomer having an ethylenic double bond selected from acrylic acid esters, methacrylic acid esters, styrene, vinyl acetate, vinyl chloride, N-vinylpyrrolidone and acrylamide, and a monomer having an acidic group and an ethylenic double bond selected from acrylic acid, methacrylic acid, p-styrenecarboxylic acid, p-styrenesulfonic acid, p-hydroxystyrene and maleic anhydride, is preferably used.

The binder resin having an acidic group is preferably used in an amount of 0.5 parts to 4 parts by mass, and particularly preferably in an amount of 1 part to 3 parts by mass, relative to 1 part by mass of the photosensitive compound (polymerizable monomer).

The solvent used in the coloring composition for photolithographic methods may be one or more oily media selected from fatty acid esters, ketones, aromatics, alcohols, glycols, glycerin, alkylene glycol monoalkyl ethers, alkylene glycol dialkyl ethers, ethers, and nitrogen-containing polar organic solvents.

The use amount of these solvents is preferably 3 to 30 times, and particularly preferably 4 to 15 times, the total mass of the components other than the solvent in the coloring composition.

Furthermore, in the coloring composition for photolithographic methods according to the present invention, known additives such as a wetting agent, a discolorization preventing agent, an emulsion stabilizer, an ultraviolet absorbent, an antiseptic, an antifungal agent, a pH adjusting agent, a surface tension adjusting agent, a defoamant, a viscosity adjusting agent, a dispersion stabilizer, an antirust agent, and a chelating agent (described in JP 2003-306623A) may be incorporated as necessary, in addition to the components described above. These various additives may be added to the oil phase or to the aqueous phase during the preparation.

The coloring composition for color filters of the present invention can be prepared by a method which includes a step of uniformly mixing and dispersing an azo compound represented by the formula (1), a polymerizable compound, a solvent, and other various additives by using, for example, an instrument such as a bead mill, a ball mill, a sand mill, a double-roll mill, a three-roll mill, a homogenizer, a kneader or a shaking dispersing machine; and a step of adjusting the viscosity using the solvent described above or the like.

The method of forming a color filter on a substrate by using the coloring composition for color filters of the present invention may be achieved by using a known photolithographic method. For example, a color filter may be obtained by a method which includes a step of uniformly applying the coloring composition of the present invention on a display substrate by a known method such as a printing method, a spraying method, a bar coating method, a roll coating method, or a spin coating method; a step of removing the solvent in the composition by heating; a step of exposing the color filter pattern on the display substrate by using a high pressure mercury lamp or the like; an alkali development step; a washing step; and a baking step.

As the developer solution used in the method for producing a color filter of the present invention, any composition which dissolves the composition of the present invention but does not dissolve radiation-irradiated parts can be used. Specifically, combinations of various organic solvents or alkaline aqueous solutions can be used.

As the organic solvent, the solvents described above that are used to prepare the composition of the present invention may be used.

As the alkaline aqueous solution, for example, an alkaline aqueous solution in which an alkaline compound such as sodium hydroxide, potassium hydroxide, sodium carbonate, sodium silicate, sodium metasilicate, aqueous ammonia, ethylamine, diethylamine, dimethylethanolamine, tetramethylammonium hydroxide, tetraethylammonium hydroxide, choline, pyrrole, piperidine, or 1,8-diazabicyclo[5.4.0]-7-undecene at a concentration of 0.001% to 10% by mass, and preferably 0.01% to 1% by mass, is used. Meanwhile, when a developer solution formed from such an alkaline aqueous solution is used, generally the color filter is developed, and then washed with water.

2) Inkjet Method

When a color filter is formed by using an inkjet method, the polymerizable compound of the coloring composition for color filters of the present invention is not particularly limited as long as the polymerizable compound is conventionally used in inks for inkjet systems, and any polymerizable compound may be used. A photosensitive compound and/or a thermosetting compound is suitably used.

The photosensitive compound may be a photopolymerizable monomer selected from acrylic acid esters, methacrylic acid esters, urethane acrylate, urethane methacrylate, acrylic acid amide, methacrylic acid amide, alkyl acrylate, benzyl methacrylate, benzyl acrylate, aminoalkyl methacrylate and the like. These photopolymerizable monomers are preferably used in combination with a photopolymerization initiator selected from compounds such as benzophenone derivatives, acetophenone derivatives, benzoin derivatives, benzoin ether derivatives, thioxanthone derivatives, anthraquinone derivatives, naphthoquinone derivatives, and triazine derivatives. Furthermore, in addition to the photopolymerizable monomers described above, a photopolymerizable monomer having a hydrophilic group, such as acrylic acid, methacrylic acid, maleic acid or vinyl acetate may also be added.

Examples of the thermosetting compound include thermosetting resins such as a melamine resin, a urea resin, an alkyd resin, an epoxy resin, a phenolic resin, and a cyclopentadiene resin.

In the case of using an inkjet method, the solvent used in the coloring composition may be an oil medium or an aqueous medium, but an aqueous medium is more suitably used. As the aqueous medium, water, or a mixed solvent of water and a water-soluble organic solvent is used, but a mixed solvent of water and a water-soluble organic solvent is preferred. Furthermore, it is desirable to use a solvent that has been deionization treated.

The oily medium that is used in the coloring composition described above is not particularly limited, but for example, those listed as the solvents for the coloring composition used in a photolithographic method can be used.

The solvent used in the aqueous medium may be a solvent selected from alcohols, ketones, ethers, glycols, glycerin, alkylene glycol monoalkyl ethers, alkylene glycol dialkyl ethers, alkanolamines, and nitrogen-containing polar organic solvents, and having water-solubility. These water-soluble organic solvents may be used individually, or two or more kinds may be used as a mixture.

The use amount of these solvents is not particular limited, but it is desirable to appropriately adjust the use amount such that the viscosity of the coloring composition is 20 mPa·s or less, and preferably 10 mPa·s or less at room temperature.

The coloring composition for inkjet of the present invention can be prepared by a method which includes a step of dispersing and mixing the components in the same manner as for the coloring composition for photolithographic methods. At the time of dispersion, a dispersant may also be incorporated in the same manner as in a photolithographic method, according to necessity.

Furthermore, various known additives such as a wetting agent, a discolorization preventing agent, an emulsion stabilizer, an ultraviolet absorbent, an antiseptic, an antifungal agent, a pH adjusting agent, a surface tension adjusting agent, a defoamant, a viscosity adjusting agent, and a dispersion stabilizer may also be added to the coloring composition, as necessary in addition to the components described above.

The method for forming a color filter using the coloring composition obtained as described above is not particularly limited as long as the method is a method for forming a color filter based on a known inkjet system. For example, a color filter can be formed by a method which includes a step of forming a predetermined color filter pattern in the form of liquid droplets on a substrate; a step of drying this color filter pattern; and a step of performing a heat treatment, light irradiation or both of them to cure the color filter pattern on the substrate, and thereby forming a film.

Thus, a photolithographic method and an inkjet method were described, but the color filter of the present invention may also be obtained according to other methods.

Even in the case of using a color filter forming method other than described above (for example, various printing methods such as an offset printing method), as long as the coloring composition contains the polymerizable compound and solvent described above and uses an azo compound represented by formula (1) as an azo pigment, the resulting coloring composition for color filters and the resulting color filter are both included in the scope of the present invention.

For example, the components such as polymerizable compound, solvent and additives, and the formulation at the time of forming a color filter may be selected according to conventional examples, and are not limited to those mentioned in the description of the photolithographic method and inkjet method described above.

The color filter of the present invention obtainable as described above can have pixels formed, together with a color filter pattern of G (green) and B (blue), by a known method. Such a filter has very high transparency and excellent spectral characteristics, and thus a liquid crystal display capable of displaying clear images with a small depolarization action can be provided. Furthermore, when a device in which this color filter is formed is used, a camera module having satisfactory spectral characteristics can be provided.

The color filter of the present invention can be used in liquid crystal display elements, organic EL display elements, or solid-state image pickup elements such as a charge coupled device (CCD) or a complementary metal oxide semiconductor (CMOS), and it is preferable to use the color filter in solid-state image pickup elements (high resolution CCD elements or CMOS elements having more than one million pixels). The color filter for solid-state image pickup elements of the present invention can be used, for example, as a color filter that is disposed between the light-receiving unit of each pixel constituting a CCD or a CMOS and a microlens for collecting light.

Hereinafter, the color filter for solid-state image pickup elements obtainable by using the coloring composition for color filters of the present invention, and a method for producing the color filter will be described.

[Color Filter for Solid-State Image Pickup Elements and Method for Producing the Same]

The method for producing a color filter for solid-state image pickup elements includes a step of forming a coloring composition layer by applying the coloring composition of the present invention described above on a support (hereinafter, also referred to as "coloring composition layer forming step"); a step of exposing the coloring composition layer through a mask (hereinafter, also referred to as "exposure step"); and a step of developing the coloring composition layer after exposure (hereinafter, also referred to as "developing step") and thereby forming a colored pattern (hereinafter, also referred to as "colored pixels").

Furthermore, the color filter for solid-state image pickup elements is a color filter formed by using the coloring composition for color filters of the present invention.

The color filter for solid-state image pickup elements may have at least a red pattern (red pixels) formed by using the coloring composition for color filters of the present invention. As a specific form of the color filter for solid-state image pickup elements of the present invention, for example, a form of a multicolor color filter in which the red pattern and other colored patterns are combined (for example, a color filter of three or more colors having at least the red pattern, a blue pattern and a green pattern) is suitable.

Hereinafter, the color filter for solid-state image pickup elements may be simply referred to as a "color filter".

<Coloring Composition Layer Forming Step>

In the coloring composition layer forming step, the coloring composition is applied on a support, and thereby a coloring composition layer is formed.

As the support that can be used in the present step, for example, a substrate for solid-state image pickup elements, in which an image pickup element (light-receiving element) such as a charge coupled device (CCD) or a complementary metal oxide semiconductor (CMOS) is provided on a substrate (for example, a silicon substrate), can be used.

The colored pattern according to the present invention may be formed on an image pickup element-formed surface side (front surface) of the substrate for solid-state image pickup elements, or may be formed on a non-image pickup element-formed surface side (back surface).

A light shielding film may be provided between the respective image pickup elements on a substrate for solid-state image pickup elements, or on the back surface of the substrate for solid-state image pickup elements.

Furthermore, an undercoat layer may also be provided on the support as necessary, for an improvement of adhesion with upper layers, prevention of diffusion of substances, or flattening of the substrate surface.

As a method for applying the coloring composition of the present invention on a support, various coating methods such as slit coating, an inkjet method, rotary coating, flow cast coating, roll coating, and a screen printing method can be applied.

The thickness of the coloring composition layer is preferably 0.1 µm to 10 µm, more preferably 0.2 µm to 5 µm, and even more preferably 0.2 µm to 3 µm.

Drying (prebake) of the coloring composition layer applied on the support can be carried out on a hot plate or in an oven at a temperature of 50° C. to 140° C. for 10 seconds to 300 seconds.

<Exposure Step>

In the exposure step, the coloring composition layer formed in the coloring composition layer forming step is exposed patternwise through a mask having a predetermined mask pattern by using, for example, an exposure apparatus such as a stepper.

As the radiation (light) that can be used for the exposure, particularly, ultraviolet radiation such as g-line or i-line is preferably (particularly preferably, i-line) used. The amount of irradiation (exposure dose) is preferably 30 mJ/cm$^2$ to 1500 mJ/cm$^2$, more preferably 50 mJ/cm$^2$ to 1000 mJ/cm$^2$, and most preferably 80 mJ/cm$^2$ to 500 mJ/cm$^2$.

<Developing Step>

Subsequently, when an alkali development treatment is carried out, the coloring composition layer in the unexposed areas generated in the exposure step is dissolved out in an aqueous alkali solution, and only the photocured areas remain.

As the developer solution, an organic alkali developer solution which does not cause damage to the underlying image pickup element, circuit and the like, is desirable. The development temperature is usually 20° C. to 30° C., and the development time is conventionally 20 seconds to 90 seconds. In order to further remove the residue, development may be carried out for 120 seconds to 180 seconds in recent processes. Furthermore, in order to further enhance the residue removability, a step of shaking off the developer solution every 60 seconds and supplying a fresh developer solution, may be repeated several times.

Examples of the alkali agent used in the developer solution include organic alkaline compounds such as aqueous ammonia, ethylamine, diethylamine, dimethylethanolamine, tetramethylammonium hydroxide, tetraethylammonium hydroxide, choline, pyrrole, piperidine, and 1,8-diazabicyclo[5,4,0]-7-undecene. An alkaline aqueous solution prepared by diluting such an alkali agent with pure water to a concentration of 0.001% to 10% by mass, and preferably 0.01% to 1% by mass, is preferably used as a developer solution.

Meanwhile, an inorganic alkali may be used in the developer solution, and preferred examples of the inorganic alkali include sodium hydroxide, potassium hydroxide, sodium carbonate, sodium hydrogen carbonate, sodium silicate, and sodium metasilicate.

Meanwhile, in the case of using a developer solution formed from such an alkaline aqueous solution, generally, the color filter is washed (rinsed) with pure water after development.

Subsequently, it is preferable to perform a heating treatment (postbake) after drying the color filter. In the case of forming a colored pattern of multiple colors, cured films can be produced by sequentially repeating the process described above for each color. Thereby, a color filter is obtained.

The postbake is a heating treatment carried out after development, in order to complete curing, and a thermal curing treatment is carried out usually at 100° C. to 240° C., and preferably 200° C. to 240° C.

This postbake treatment can be carried out on the coating film obtained after development, in a continuous mode or a batch mode by using a heating means such as a hot plate, a convection oven (hot air circulation type dryer), or a high frequency heater under the conditions described above.

Meanwhile, if necessary, the production method of the present invention may have steps that are known in the methods for producing a color filter for solid-state image pickup elements, as steps other than the described above. For example, the method may include, if necessary, a curing step of curing the formed colored pattern by heating and/or exposure, after performing the coloring composition layer forming step, exposure step and developing step.

Furthermore, in the case of using the coloring composition according to the present invention, for example, contamination may occur due to the clogging of the nozzle or pipes of the discharge unit of a coating apparatus, or the attachment, sedimentation and drying of the coloring composition or pigment inside a coating machine. Thus, in order to efficiently wash the contamination caused by the coloring composition of the present invention, it is preferable to use a solvent related to the composition of the present invention described above as a washing liquid. Furthermore, the washing liquids described in JP 1995-128867A (JP H07-128867A), JP 1995-145652A (JP H07-128867A), JP 1996-278637A (JP H08-278637A), JP 2000-273370A, JP 2007-085140A, JP 2006-291191A, JP 2007-002101A, JP 2007-002102A, JP 2007-281523A and the like can also be suitably used for washing and removal of the coloring composition according to the present invention.

Among the washing liquids described above, alkylene glycol monoalkyl ether carboxylate and alkylene glycol monoalkyl ether are preferred.

These solvents may be used individually, or two or more kinds may be used as a mixture. In the case of mixing two or more kinds, it is preferable to mix a solvent having a hydroxyl group and a solvent which does not have a hydroxyl group. The mass ratio of the solvent having a hydroxyl group and the solvent which does not have a hydroxyl group is 1/99 to 99/1, preferably 10/90 to 90/10, and more preferably 20/80 to 80/20. A mixed solvent of propylene glycol monomethyl ether acetate (PGMEA) and propylene glycol monomethyl ether (PGME) at a ratio of 60/40 is particularly preferred. Meanwhile, in order to enhance the penetrability of the washing liquid to contaminants, the surfactant related to the composition of the present invention described above may also be added to the washing liquid.

Since the color filter for solid-state image pickup elements of the present invention is formed by using the azo compound represented by the formula (1), the spectral characteristics in terms of red color are excellent.

The thickness of the colored pattern (colored pixel) in the color filter for solid-state image pickup elements is preferably 2.0 μm or less, and more preferably 1.0 μm or less.

Furthermore, the size (pattern width) of the colored pattern (colored pixel) is preferably 2.5 μm or less, more preferably 2.0 μm or less, and particularly preferably 1.7 μm or less.

[Solid-State Image Pickup Element]

The solid-state image pickup element includes the color filter for solid-state image pickup elements of the present invention. The configuration of the solid-state image pickup element of the present invention is not particularly limited as long as it is a configuration which includes the color filter for solid-state image pickup elements of the present invention, and functions as a solid-state image pickup element, but for example, a configuration such as described below may be employed.

It is a configuration in which plural photodiodes and transport electrodes formed of polysilicon or the like that constitute the light-receiving areas of a solid-state image pickup element (a CCD image sensor, a CMOS image sensor or the like) are provided on a support; a light shielding film formed of tungsten or the like, which has openings only in the light-receiving areas of the photodiodes, is provided on the photodiodes and the transport electrodes; a device protecting film formed of silicon nitride or the like, which is formed so as to cover the entire surface of the light shielding film and the light-receiving areas of the photodiodes, is provided on the light shielding film; and the color filter for solid-state image pickup elements of the present invention is provided on the device protecting film.

Furthermore, a configuration having a light collecting means (for example, a microlens; hereinafter, the same applies) over the device protecting layer and under the color filter (closer to the support), or a configuration having a light collecting means on the color filter, may also be employed.

[Ink for Inkjet Recording]

Next, the ink for inkjet recording of the present invention will be explained.

The ink for inkjet recording of the present invention (hereinafter, may be referred to as "ink") preferably uses a pigment dispersion that will be described below. Preferably, a water-soluble solvent, water or the like is mixed to prepare the ink.

However, unless there are particular problems, the pigment dispersion of the present invention that will be described below may be used directly.

[Pigment Dispersion (2)]

The pigment dispersion of the present invention contains at least one kind of the azo pigment of the present invention (an azo compound represented by the formula (1), a tautomer thereof, and a salt or hydrate of the azo compound or the tautomer). Thereby, a pigment dispersion which is excellent in chromatic characteristics, durability and dispersion stability can be obtained.

The pigment dispersion of the present invention may be an aqueous system or a non-aqueous system, but a pigment dispersion of an aqueous system is preferred. The aqueous liquid used to disperse the pigment in the aqueous pigment dispersion of the present invention contains water as a main component, and if desired, a mixture obtained by adding a hydrophilic organic solvent can be used.

Examples of the hydrophilic organic solvent include alcohols such as methanol, ethanol, propanol, isopropanol, butanol, isobutanol, sec-butanol, t-butanol, pentanol, hexanol, cyclohexanol, and benzyl alcohol; polyhydric alcohols such as ethylene glycol, diethylene glycol, triethylene glycol, polyethylene glycol, propylene glycol, dipropylene glycol, polypropylene glycol, butylene glycol, hexanediol, pentanediol, glycerin, hexanetriol, and thiodiglycol; glycol derivatives such as ethylene glycol monomethyl ether, ethylene glycol monoethyl ether, ethylene glycol butyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monoethyl ether, and ethylene glycol monophenyl ether; amines such as ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine, and tetramethylpropylenediamine; formamide, N,N-dimethylformamide, N,N-dimethylacetamide, dimethyl sulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile, and acetone.

Furthermore, the pigment dispersion of an aqueous system of the present invention may contain an aqueous resin. Examples of the aqueous resin include water-soluble resins that dissolve in water, water-dispersible resins that disperse in water, colloidal dispersion resins, and mixtures thereof. Specific examples of the aqueous resins include acrylic resins, styrene-acrylic resins polyester-based resins, polyamide-based resins, polyurethane-based resins and fluororesins.

When the pigment dispersion of an aqueous system according to the present invention contains an aqueous resin, the content ratio is not particularly limited. For example, the content ratio of the aqueous resin can be adjusted to 0% to 100% by mass based on the pigment.

Furthermore, a surfactant and a dispersant may also be used in order to enhance dispersion of the pigment and the quality of images. Examples of the surfactant include anionic, nonionic, cationic and zwitterionic surfactants, and any surfactant may be used. However, it is preferable to use anionic or nonionic surfactants.

When the pigment dispersion of an aqueous system according to the present invention contains a surfactant, the content ratio is not particularly limited. For example, the content ratio of the surfactant can be adjusted to 0% to 100% by mass based on the pigment.

Examples of the anionic surfactant include fatty acid salts, alkylsulfuric acid ester salts, alkylbenzenesulfonates, alkylnaphthalenesulfonates, dialkylsulfosuccinates, alkyl diaryl ether disulfonates, alkylphosphates, polyoxyethylene alkyl ether sulfates, polyoxyethylene alkyl aryl ether sulfates, naphthalenesulfonate-formalin condensates, polyoxyethylene alkyl phosphoric acid ester salts, glycerol borate fatty acid esters, and polyoxyethylene glycerol fatty acid esters.

Examples of the nonionic surfactant include polyoxyethylene alkyl ether, polyoxyethylene alkyl aryl ether, polyoxyethylene-oxypropylene block copolymers, sorbitan fatty acid esters, polyoxyethylene sorbitan fatty acid esters, polyoxyethylene sorbitol fatty acid esters, glycerin fatty acid esters, polyoxyethylene fatty acid esters, polyoxyethylene alkylamines, fluorine-based surfactants, and silicon-based surfactants.

The pigment dispersion of an aqueous system of the present invention is a dispersion in which the azo pigment of the present invention is dispersed in a non-water-based vehicle. Examples of the resin used in the non-water-based vehicle include petroleum resins, casein, shellac, rosin-modified maleic acid resins, rosin-modified phenolic resins, nitrocellulose, cellulose acetate butyrate, cyclized rubber, chloride rubber, oxide rubber, hydrochloride rubber, phenolic resins, alkyd resins, polyester resins, unsaturated polyester resins, amino resins, epoxy resins, vinyl resins, vinyl chloride, vinyl chloride-vinyl acetate copolymers, acrylic resins, methacrylic resins, polyurethane resins, silicone resins, fluororesins, dry oil, synthetic dry oil, styrene/maleic acid resins, styrene/acrylic resins, polyamide resins, polyimide resins, benzoguanamine resins, melamine resins, urea resins, chlorinated polypropylene, butyral resins, and vinylidene chloride resins. Photocurable resins may also be used as the non-water-based vehicle.

Examples of the solvent used in the non-water-based vehicle include aromatic solvents such as toluene, xylene, and methoxybenzene; acetic acid ester-based solvents such as ethyl acetate, butyl acetate, propylene glycol monomethyl ether acetate, and propylene glycol monoethyl ether acetate; propionate-based solvents such as ethoxyethyl propionate; alcohol-based solvents such as methanol and ethanol; ether-based solvents such as butylcellosolve, propylene glycol monomethyl ether, diethylene glycol ethyl ether, and diethylene glycol dimethyl ether; ketone-based solvents such as methyl ethyl ketone, methyl isobutyl ketone, and cyclohexanone; aliphatic hydrocarbon-based solvents such as hexane; nitrogen compound-based solvents such as N,N-dimethylformamide, γ-butyrolactam, N-methyl-2-pyrrolidone, aniline, and pyridine; lactone-based solvents such as γ-butyrolactone; and carbamic acid esters such as a mixture of methyl carbamate and ethyl carbamate at 48:52.

The content proportion of the pigment dispersion in the ink of the present invention is preferably in the range of 1% to 100% by mass, particularly preferably in the range of 3% to 20% by mass, and among others, most preferably in the range of 3% to 10%, when the hue, color density, chroma, transparency and the like of the images formed on recording media.

It is preferable that the ink of the present invention contain the azo pigment of the present invention in an amount of from 0.1 parts by mass to 20 parts by mass, more preferably from 0.2 parts by mass to 10 parts by mass, and even more preferably from 1 part by mass to 10 parts by mass, relative to 100 parts by mass of the ink. Furthermore, in the ink of the present invention, another pigment may be used in combination with the azo pigment of the present invention. When two or more kinds of pigments are used in combination, the total content of the pigment is preferably in the range described above.

The ink of the present invention can be used not only in the formation of monochromatic images but also in the formation of full color images. In order to form full-color images, a magenta color ink, a cyan color ink, and a yellow color ink can be used, and also, in order to adjust the color tone, a black tone color may be further used.

Furthermore, the ink according to the present invention can simultaneously use another pigment in addition to the azo pigment according to the present invention described above. Examples of yellow pigments that can be applied include C.I. Pigment Yellow 74, C.I. Pigment Yellow 128, C.I. Pigment Yellow 155, and C.I. Pigment Yellow 213, and examples of magenta pigments that can be applied include C.I. Pigment Violet 19 and C.I. Pigment Red 122. Examples of cyan pigments that can be applied include C.I. Pigment Blue 15:3 and C.I. Pigment Blue 15:4. Apart from these, any arbitrary pigments can be used. Examples of black color material that can be applied include disazo pigments, trisazo pigments, tetraazo pigments, and dispersions of carbon black.

As the water-soluble solvents used in the ink for inkjet recording of the present invention, there are polyhydric alcohols, polyhydric alcohol derivatives, nitrogen-containing solvents, alcohols, and sulfur-containing solvents.

Specific examples of polyhydric alcohols include ethylene glycol, diethylene glycol, propylene glycol, butylene glycol, triethylene glycol, 1,5-pentanediol, 1,2,6-hexanetriol, and glycerin.

Examples of the polyhydric alcohol derivatives include ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, propylene glycol monobutyl ether, dipropylene glycol monobutyl ether, and ethylene oxide adduct of diglycerin.

Furthermore, examples of the nitrogen-containing solvents include pyrrolidone, N-methyl-2-pyrrolidone, cyclohexylpyrrolidone, and triethanolamine, and examples of the alcohols include ethanol, isopropyl alcohol, butyl alcohol, and benzyl alcohol. Examples of the sulfur-containing solvents include thiodiethanol, thiodiglycerol, sulfolane, and dimethyl sulfoxide. In addition to those, propylene carbonate, ethylene carbonate, and the like can also be used.

The water-soluble solvent used in the present invention may be used individually, or may be used as mixtures of two or more kinds. The content of the water-soluble solvent is from 1% by mass to 60% by mass, and preferably from 5% by mass to 40% by mass, based on the total amount of the ink. If the amount of the water-soluble solvent in the ink is less than 1% by mass, there may be occasions in which a sufficient optical density cannot be obtained. On the contrary, if the amount of the water-soluble solvent is larger than 60% by mass, there may be occasions in which the viscosity of the liquid may increase, and the spray characteristics of the ink liquid may be destabilized.

Preferred properties of the ink for inkjet recording of the present invention are as follows.

The surface tension of the ink is preferably from 20 mN/m to 60 mN/m, more preferably from 20 mN/m to 45 mN/m, and even more preferably from 25 mN/m to 35 mN/m. If the surface tension is less than 20 mN/m, since the liquid overflows to the nozzle surface of the recording head, printing may not be carried out normally. On the other hand, if the surface tension is greater than 60 mN/m, penetrability into recording media after printing is delayed, and the drying time may be prolonged.

Meanwhile, the surface tension was measured in an environment of 23° C. and 55% RH by using a Wilhelmy type surface tensiometer such as described above.

The viscosity of the ink is preferably equal to or higher than 1.2 mPa·s and equal to or lower than 8.0 mPa·s, more preferably equal to or higher than 1.5 mPa·s and lower than 6.0 mPa·s, and even more preferably equal to or higher than 1.8 mPa·s and lower than 4.5 mPa·s. If the viscosity is higher than 8.0 mPa·s, ejection properties may deteriorate. On the other hand, if the viscosity is lower than 1.2 mPa·s, long-term spray properties may deteriorate.

Meanwhile, the measurement of the viscosity (including the viscosity that will be described below) was carried out by using a rotary viscometer RHEOMAT 115 (manufactured by Contraves Advanced Devices Sdn. Bhd.) at 23° C. at a shear rate of 1400 s$^{-1}$.

In addition to the various components described above, water is added to the ink to the extent that preferred surface tension and viscosity are acquired. There are no particular limitations on the amount of water added, but the amount of water added is preferably from 10% by mass to 99% by mass, and more preferably from 30% by mass to 80% by mass, based on the total amount of the ink.

Furthermore, if necessary, for the purpose of characteristics control such as an improvement of ejection properties, polyethyleneimine, polyamines, polyvinylpyrrolidone, polyethylene glycol, cellulose derivatives such as ethyl cellulose and carboxymethyl cellulose, polysaccharides and derivatives thereof, other water-soluble polymers, polymer emulsions such as acrylic polymer emulsions, polyurethane-based emulsions and hydrophilic latex, hydrophilic polymer gels, cyclodextrin, macrocyclic amines, dendrimers, crown ethers, urea and derivatives thereof, acetamide, silicone-based surfactants, fluorine-based surfactants, and the like can be used.

Furthermore, in order to adjust electrical conductivity and pH, alkali metal compounds such as potassium hydroxide, sodium hydroxide, and lithium hydroxide; nitrogen-containing compounds such as ammonium hydroxide, triethanolamine, diethanolamine, ethanolamine, and 2-amino-2-methyl-1-propanol; alkaline earth metal compounds such as calcium hydroxide; acids such as sulfuric acid, hydrochloric acid, and nitric acid; salts of a strong acid and a weak alkali, such as ammonium sulfate; and the like can be used.

In addition, a pH buffer, an antioxidant, an antifungal agent, a viscosity adjusting agent, a conductive agent, an ultraviolet absorbent, and the like can also be added according to necessity.

EXAMPLES

Hereinafter, the present invention will be specifically described based on Examples, but the present invention is not intended to be limited to these Examples. Meanwhile, in the following Examples, unless particularly stated otherwise, the units "percent (%)" and "parts" represent "mass %" and "parts by mass".

Synthesis Example 1

Synthesis of Specific Compound Example D-21

Specific compound example D-21 was synthesized by the following route.

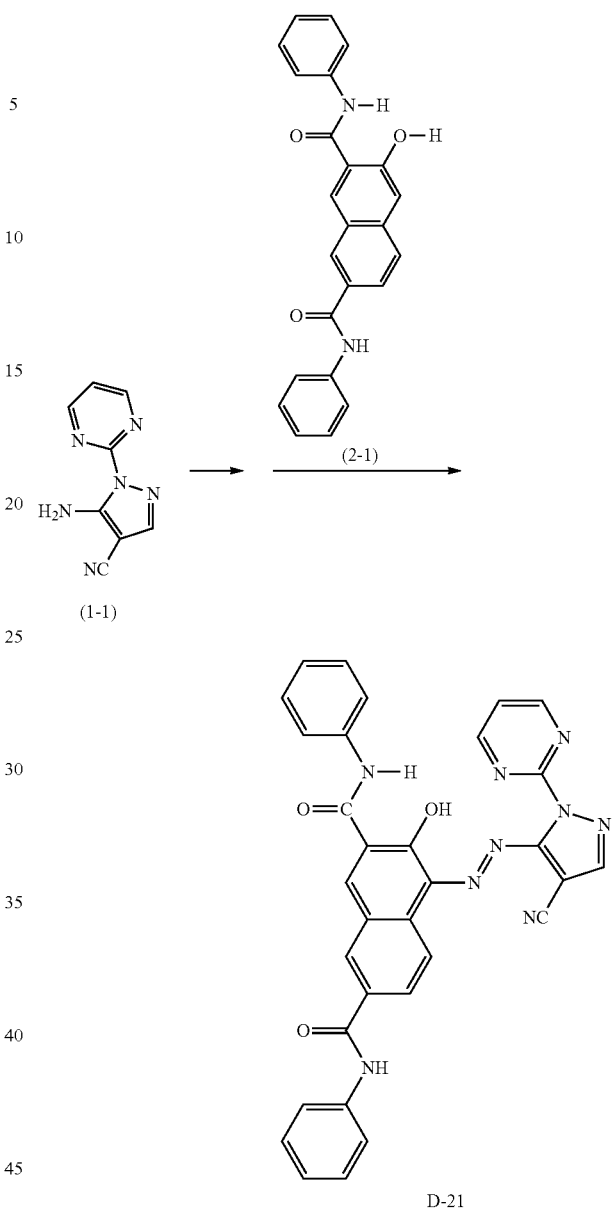

1.0 g of a compound (1-1) was added to 10 ml of phosphoric acid (manufactured by Wako Pure Chemical Industries, Ltd.; special grade reagent: purity 85%; hereinafter, the same), and the compound was dissolved therein by warming to 30° C. While keeping an obtained solution at 0° C. to 5° C. by ice-cooling, 0.38 g of sodium nitrite was added thereto, and the mixture was stirred for 1.5 hours to obtain a diazonium salt solution. This diazonium salt solution was added dropwise to a solution prepared by dissolving 1.2 g of a compound (2-1) in 5 ml of dimethylacetamide, while the system was maintained at 5° C. to 10° C. Thereafter, while the mixed solution thus obtained was maintained at 5° C. to 10° C., the mixed solution was stirred for 1 hour. Subsequently, the ice bath was removed, and the mixed solution was further stirred for 0.5 hours. 50 ml of water was added to the reaction liquid, and the reaction liquid was heated at 80° C. and completely dissolved. Crystals precipitated therefrom were separated by filtration and washed with 50 ml of water. The crystals were dried, and then 500 ml of dimethylacetamide was added to the crystals. The mixture was stirred for 3 hours at 80° C. and for 1 hour at room temperature. Crystals precipitated therefrom were filtered and washed with 500 ml of methanol. The crystals thus obtained were dried, and thus 1.5 g of a compound D-21 was obtained. Yield: 48%.

FIG. 1 shows an infrared absorption chart of the compound D-21 thus obtained.

Synthesis Examples 2 to 8

Synthesis of Specific Compound Examples D-22, D-23, D-24, D-25, D-26, D-28 and D-33

Compounds D-22, D-23, D-24, D-25, D-26, D-28 and D-33 were respectively obtained in the same manner as in [Synthesis Example 1] described above.

Infrared absorption charts of the compounds D-22, D-23, D-24, D-26 and D-28 are shown in FIG. 2 to FIG. 6.

Synthesis Example of Comparative Compounds 1

Synthesis of Comparative Compound 4

The synthesis of the comparative compound 4 was carried out by the following route.

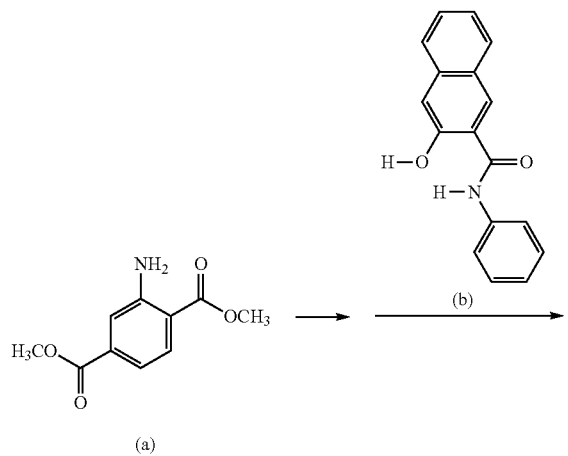

(a)

Comparative Compound 4

15 ml of water and 2.2 ml of concentrated hydrochloric acid were added to 2.1 g of a compound (a), and the mixture was stirred at −2° C. to 2° C. To this solution, a solution prepared by dissolving 0.72 g of sodium nitrite in 5 ml of water was added dropwise for 10 minutes, and thus a diazonium salt solution was obtained. Separately, a solution was obtained by adding 10 ml of dimethylacetamide (DMAc) to 2.50 g of a compound (b), and while the solution was maintained at 5° C. to 10° C. under stiffing, the diazonium salt solution described above was added thereto. Simultaneously with the completion of the addition, the ice bath was removed, and the mixture was further stirred for 2 hours. Crystals precipitated therefrom were separated by filtration, and were washed with 50 ml of water. The crystals thus obtained were recrystallized from 50 ml of methanol and cooled to 25° C., and the crystals precipitated therefrom were separated by filtration. The crystals thus obtained were dried, and thus 2.4 g of a comparative compound 4 was obtained. Yield: 51.8%.

Synthesis Example Comparative Compound 2

Synthesis of Comparative Compound 5

Synthesis of the comparative compound 5 was carried out by the following route.

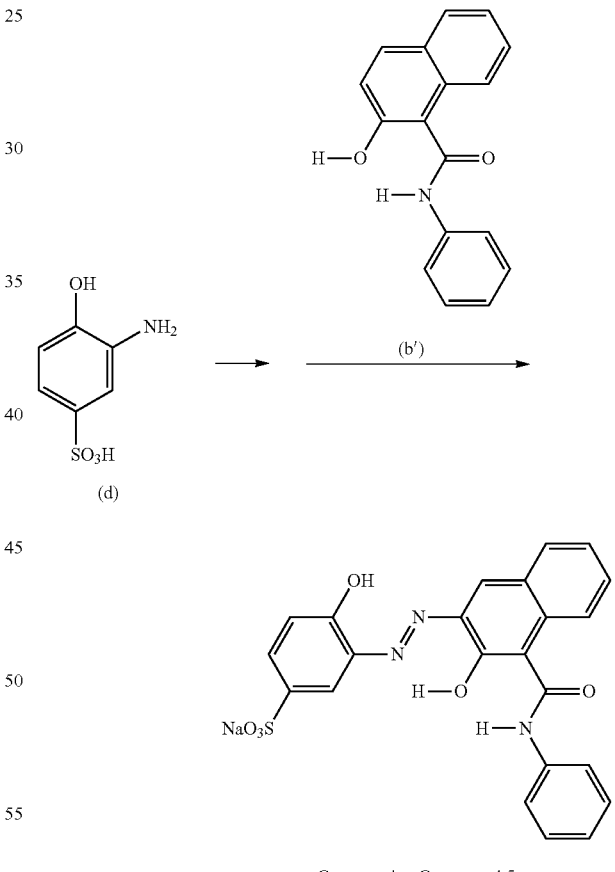

Comparative Compound 5

15 ml of water and 2.2 ml of concentrated hydrochloric acid were added to 1.9 g of a compound (d), and the mixture was stirred at −2° C. to 2° C. To this solution, a solution prepared by dissolving 0.72 g of sodium nitrite in 5 ml of water was added dropwise for 10 minutes, and thus a diazonium salt solution was obtained. Separately, a solution was obtained by adding 40 ml of water and 2 g of sodium carbonate to 2.6 g of a compound (b'), and while the solution was maintained at 5° C. to 10° C. under stirring, the diazonium salt solution described above was added thereto. Simultaneously with the completion of the addition, the ice bath was removed, and the mixture was further stirred for 2 hours. 200 ml of saturated brine was added to the reaction liquid. Crystals precipitated therefrom were separated by filtration, washed with 30 ml of saturated brine, and dried. The crystals thus obtained were heated in 100 ml of methanol, and insoluble materials were filtered. The solution was purified by Sephadex column chromatography, and the water/methanol solution was concentrated. Crystals precipitated therefrom were separated by filtration and washed with methanol. Thus, 1.7 g of the comparative compound 5 was obtained. Yield: 35.4%.

[Comparative Compounds 6 and 7]
Compounds Described in JP 3894726B

[Comparative compound 6]

[Comparative compound 7]

Example 1

2.5 parts of D-21 as a pigment, 0.5 parts of sodium oleate, 5 parts of glycerin, and 42 parts of water were mixed, and the mixture was dispersed for 6 hours together with 100 parts of zirconia beads with a diameter of 0.1 mm by using a planetary ball mill at a speed of rotation of 300 rotations per minute. After completion of the dispersion, the zirconia beads were separated, and thus a pigment dispersion 1 was obtained.

Examples 2 to 5

Pigment dispersions 2 to 8 were prepared in the same manner as in Example 1, except that the pigment was changed as indicated in Table 1.

Comparative Example 1

A red comparative pigment dispersion 1 was obtained in the same manner as in Example 1, except that C.I. Pigment Red 254 (P.R. 254) (BT-CF manufactured by BASF Corp.) was used instead of the pigment (D-21) used in Example 1.

Comparative Example 2

A yellow comparative pigment dispersion 2 was obtained in the same manner as in Example 1, except that C.I. Pigment Yellow 74 (P.Y. 74) (IRALITE YELLOW GO manufactured by BASF Corp.) was used instead of the pigment (D-21) used in Example 1.

Comparative Example 3

A yellow comparative pigment dispersion 3 was obtained in the same manner as in Example 1, except that C.I. Pigment Yellow 155 (P.Y. 155) (INKJET YELLOW 4G VP2532 manufactured by Clariant GmbH) was used instead of the pigment (D-21) used in Example 1.

Comparative Example 4

A red comparative pigment dispersion 4 was obtained in the same manner as in Example 1, except that the comparative compound 4 was used instead of the pigment (D-21) used in Example 1.

Comparative Example 5

A red comparative pigment dispersion 5 was obtained in the same manner as in Example 1, except that the comparative compound 5 was used instead of the pigment (D-21) used in Example 1.

Comparative Example 6

A red comparative pigment dispersion 6 was obtained in the same manner as in Example 1, except that the comparative compound 6 was used instead of the pigment (D-21) used in Example 1.

Comparative Example 7

A red comparative pigment dispersion 7 was obtained in the same manner as in Example 1, except that the comparative compound 7 was used instead of the pigment (D-21) used in Example 1.

(Evaluation)
<Dispersion Stability>
The volume average particle size of each of the pigment dispersions obtained as described above was measured by a routine method, by using a dynamic light scattering particle size analyzer (MICROTRACK UPA150 manufactured by Nikkiso Co., Ltd.). A pigment dispersion for which the volume average particle size measured 2 hours after the preparation of the pigment dispersion, and the volume average particle size after storage for 2 days at 70° C. were both 230 nm or less, was rated as G (good), and a pigment dispersion for which at least any one of the volume average particle sizes exceeded 230 nm was rated as NG (no good). The results are shown in Table 1.

<Evaluation of Light Fastness>

A coated material having an image density of 1.0 (measured by using a reflection densitometer (X-RITE 938 manufactured by X-Rite, Inc.)), which was obtained by applying each pigment dispersion on a photo matte paper <Exclusive for Pigment> manufactured by Seiko Epson Corp. using a No. 3 bar coater, was irradiated with xenon light (170,000 lux; in the presence of a filter having a cutoff of 325 nm or less) for 14 days by using a fadeometer. The image densities before and after the xenon irradiation were measured by using a reflection densitometer, and the colorant residual ratio [(density after irradiation/density before irradiation)×100%] was evaluated. The results are shown in FIG. 1.

<Evaluation of Solvent Resistance>

100 mg of each pigment was mixed with 100 ml of N-methylpyrrolidone (NMP), and the colored state of NMP was evaluated by visual inspection based on the following criteria. The results are shown in Table 1.

A: Almost not colored
B: Slightly colored, but almost transparent
C: Colored.

TABLE 1

| | Pigment dispersion | Pigment | Dispersion stability | Light fastness | Solvent resistance |
|---|---|---|---|---|---|
| Example 1 | Pigment dispersion 1 | D-21 | G | 92.0% | A |
| Example 2 | Pigment dispersion 2 | D-22 | G | 95.3% | A |
| Example 3 | Pigment dispersion 3 | D-23 | G | 93.8% | A |
| Example 4 | Pigment dispersion 4 | D-24 | G | 94.4% | A |
| Example 5 | Pigment dispersion 5 | D-25 | G | 92.1% | A |
| Example 6 | Pigment dispersion 6 | D-26 | G | 90.0% | A |
| Example 7 | Pigment dispersion 7 | D-28 | G | 92.2% | A |
| Example 8 | Pigment dispersion 8 | D-33 | G | 95.1% | A |
| Comparative Example 1 | Comparative pigment dispersion 1 | P.R. 254 | G | 62.3% | A |
| Comparative Example 2 | Comparative pigment dispersion 2 | P.Y. 74 | G | 12.5% | B |
| Comparative Example 3 | Comparative pigment dispersion 3 | P.Y. 155 | G | 51.9% | B |
| Comparative Example 4 | Comparative pigment dispersion 4 | Comparative compound 4 | G | 20.5% | C |
| Comparative Example 5 | Comparative pigment dispersion 5 | Comparative compound 5 | NG | 6.0% | C |
| Comparative Example 6 | Comparative pigment dispersion 6 | Comparative compound 6 | NG | 15.5% | C |
| Comparative Example 7 | Comparative pigment dispersion 7 | Comparative compound 7 | NG | 25.6% | C |

Example 101

Production of Color Filter According to Photolithographic Method 0.6 g of the pigment D-21, 5.0 g of 1,2-propanediol 1-monomethyl ether 2-acetate, and 10 g of zirconia beads (φ0.3 mm) were introduced into a 70-cc mayonnaise bottle, and this mixture was shaken for 6 hours in a shaking disperser (DAS200 manufactured by LAU GmbH). Thus, a pigment dispersion 101 was obtained.

The materials indicated in the following table were added to the pigment dispersion 101, and the mixture was further shaken for 30 minutes in the shaking disperser. Thus, a coloring composition 101 for color filters for photolithographic method was prepared.

TABLE 2

(Composition of coloring composition 101 for color filters)

| | |
|---|---|
| Pigment dispersion 101 | 15.6 g |
| Photosensitive resin | 2.5 g |
| (manufactured by Daicel Chemical Industries, Ltd., CYCLOMER P200) | |
| Pentaerythritol tetraacrylate | 0.2 g |
| (manufactured by Sigma-Aldrich Company) | |
| 2-Benzyl-2-dimethylamino-4'-morpholinobutyrophenone | 0.05 g |
| (manufactured by Sigma-Aldrich Company) | |
| 2,4-Diethyl-9H-thioxanthen-9-one | 0.05 g |
| (manufactured by Tokyo Chemical Industry Co., Ltd.) | |
| Propylene glycol monomethyl ether acetate | 0.8 g |
| (manufactured by Tokyo Chemical Industry Co., Ltd.) | |
| Cyclohexanone | 0.2 g |
| ((manufactured by Tokyo Chemical Industry Co., Ltd.) | |

The coloring composition 101 for color filters thus obtained was applied on a slide glass using a bar coater Rod No. 10, and then the coloring composition was dried for 5 minutes in an oven at 80° C. to obtain an ink coating film.

A portion of the coating film was appropriately masked, and then was exposed by irradiating with a high pressure mercury lamp under the conditions of 200 mJ/cm$^2$. Subsequently, development was carried out at 25° C. using a 0.5% aqueous solution of sodium carbonate, and the coating film was dried for 20 minutes in an oven at 220° C. Thus, a color filter of Example 101 was produced.

Examples 102 to 108

Coloring compositions 102 to 108 were prepared in the same manner as in Example 101, except that the pigment D-21 was changed to the pigments described in Table 3. Thus, color filters of Examples 102 to 108 were produced.

Comparative Examples 101 and 102

Comparative coloring compositions 101 and 102 were prepared in exactly the same manner as in Example 101, except that C.I. Pigment Red 254 (IRGAPHORE DPP RED, manufactured by BASF Corp.) and a pigment represented by the following formula [I] were respectively used instead of the pigment used in Example 101. Thus, color filters of Comparative Examples 101 and 102 were produced.

Formula [I]

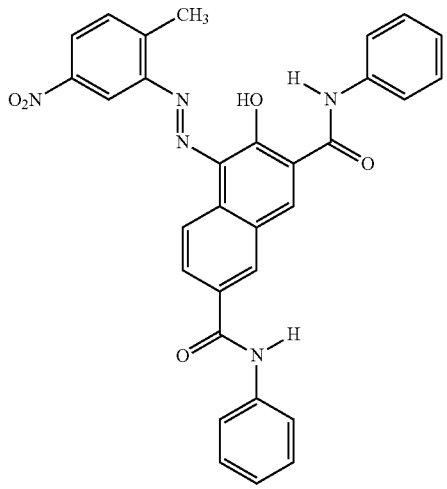

[Evaluation of Heat Resistance and Light Fastness]

Evaluations of heat resistance and light fastness were carried out by using the color filters obtained in Examples 101 to 108 and Comparative Examples 101 and 102.

<Evaluation of Heat Resistance>

A color filter was exposed for 90 minutes at 250° C. in the atmosphere, and the color difference before and after the exposure ($\Delta E^*_{ab}$) was measured with a spectrophotometer (MACBETH COLOREYE-3000 manufactured by Sakata Inx Corp.). An evaluation was made based on the following determination criteria, and the results are shown in Table 3.

<Determination Criteria>
A: $\Delta E^*_{ab} < 1.0$
B: $1.0 \leq \Delta E^*_{ab} < 1.1$
C: $1.1 \leq \Delta E^*_{ab}$

TABLE 3

| | Pigment | Heat resistance test results Color difference ($\Delta E^*_{ab}$) |
|---|---|---|
| Example 101 | D-21 | A |
| Example 102 | D-22 | A |
| Example 103 | D-23 | A |
| Example 104 | D-24 | A |
| Example 105 | D-25 | A |
| Example 106 | D-26 | A |
| Example 107 | D-28 | A |
| Example 108 | D-33 | A |
| Comp. Ex. 101 | P.R. 254 | C |
| Comp. Ex. 102 | Compound of formula [1] | B |

The color filters of Examples 101 to 108 produced by using the coloring compositions for color filters of the present invention containing the azo pigments of the present invention as a colorant, exhibited excellent heat resistance as compared with the color filters of Comparative Examples 101 and 102.

<Evaluation of Light Fastness>

A coated material having an image density of 1.0 (measured by using a reflection densitometer (X-RITE 938 manufactured by X-Rite, Inc.)), which was obtained by applying each pigment dispersion on a photo matte paper <Exclusive for Pigment> manufactured by Seiko Epson Corp. using a No. 3 bar coater, was irradiated with xenon light (170,000 lux; in the presence of a filter having a cutoff of 325 nm or less) for 20 days by using a fadeometer. The color difference before and after the exposure ($\Delta E^*_{ab}$) was measured with a spectrophotometer (MACBETH COLOREYE-3000 manufactured by Sakata Inx Corp.). An evaluation was made based on the following determination criteria, and the results are shown in Table 4.

<Determination Criteria>
A: $\Delta E^*_{ab} \leq 3.0$
B: $3.0 < \Delta E^*_{ab} \leq 6.0$
C: $6.0 < \Delta E^*_{ab}$

TABLE 4

| | Pigment | Heat resistance test results Color difference ($\Delta E^*_{ab}$) |
|---|---|---|
| Example 101 | D-21 | A |
| Example 102 | D-22 | A |
| Example 103 | D-23 | A |
| Example 104 | D-24 | A |
| Example 105 | D-25 | A |
| Example 106 | D-26 | A |
| Example 107 | D-28 | A |
| Example 108 | D-33 | A |
| Comp. Ex. 101 | P.R. 254 | C |
| Comp. Ex. 102 | Compound of formula [I] | B |

The color filters of Examples 101 to 108 produced by using the coloring compositions for color filters of the present invention containing the azo pigments of the present invention as a colorant, exhibited excellent light fastness as compared with the color filters of Comparative Examples 101 and 102.

(Evaluation of Contrast)

The contrast of the color filters thus obtained was measured by using a contrast tester CT-1 manufactured by Tsubosaka Electric Co., Ltd. The evaluation was carried out such that a color filter with contrast$\geq$23,000 was rated as A; a color filter with 23,000>contrast$\geq$18,000 was rated as B; and a color filter with 18,000>contrast was rated as C. The results are shown in Table 5.

TABLE 5

| | Pigment | Contrast |
|---|---|---|
| Example 101 | D-21 | A |
| Example 102 | D-22 | A |
| Example 103 | D-23 | A |
| Example 104 | D-24 | A |
| Example 105 | D-25 | A |
| Example 106 | D-26 | A |
| Example 107 | D-28 | A |
| Example 108 | D-33 | A |
| Comp. Ex. 101 | P.R. 254 | A |
| Comp. Ex. 102 | Compound of formula [I] | C |

The color filters of Examples 101 to 108 produced by using the coloring compositions for color filters of the present invention containing the azo pigments of the present invention represented by formula (1) as a colorant, exhibited excellent contrast as compared with the color filters of Comparative Examples 101 and 102.

(Evaluation of Stability of Dispersion Over Time)

The coloring compositions 101 to 108 and comparative coloring compositions 101 and 102 prepared in Examples 101 to 108 and Comparative Examples 101 and 102 were stored for 2 weeks in the dark at room temperature, and then the degree of precipitation of foreign materials was evaluated by visual inspection according to the following determination criteria. The results are shown in Table 6.

<Determination Criteria>
A: Precipitation was not recognized.
B: Slight precipitation was recognized.
C: Precipitation was recognized.

TABLE 6

|  | Pigment dispersion | Pigment | Stability of dispersion over time |
|---|---|---|---|
| Example 101 | Coloring composition 101 | D-21 | A |
| Example 102 | Coloring composition 102 | D-22 | A |
| Example 103 | Coloring composition 103 | D-23 | A |
| Example 104 | Coloring composition 104 | D-24 | A |
| Example 105 | Coloring composition 105 | D-25 | A |
| Example 106 | Coloring composition 106 | D-26 | A |
| Example 107 | Coloring composition 107 | D-28 | A |
| Example 108 | Coloring composition 108 | D-33 | A |
| Comp. Ex. 101 | Comparative coloring composition 101 | P.R. 254 | B |
| Comp. Ex. 102 | Comparative coloring composition 102 | Compound of formula [I] | C |

The pigment dispersions 101 to 108 prepared by using the coloring compositions for color filters of the present invention containing the azo compounds represented by the formula (1) as a colorant, exhibited excellent stability of dispersion over time while any foreign materials generated over time were not recognized, as compared with the pigment dispersions of Comparative Examples 101 and 102 prepared by using the comparative coloring compositions 101 and 102.

Example 201

Preparation of Green Pigment Dispersion Liquid
—Preparation of Green Pigment Dispersion Liquid P1—

A mixture liquid including 12.6 parts of a 100/55 (mass ratio) mixture of C.I. Pigment Green 36 and C.I. Pigment Yellow 139 as a pigment, 5.2 parts of BYK2001 (DISPERBYK; manufactured by BYK-Chemie GmbH, solids concentration: 45.1% by mass) as a dispersant, 2.7 parts of a benzyl methacrylate/methacrylic acid copolymer (acid value: 134 mg KOH/g, Mw=30,000) as a dispersing resin, and 78.3 parts of propylene glycol monomethyl ether acetate as a solvent, was mixed and dispersed for 15 hours by a bead mill. Thus, Green pigment dispersion liquid P1 was prepared.

<Preparation of Red Pigment Dispersion Liquid>
—Preparation of Red pigment dispersion liquid P2—

A mixture liquid including 12.1 parts of a 100/45 (mass ratio) mixture of D-21 and C.I. Pigment Yellow 139 as a pigment, 10.4 parts of BYK2001 (DISPERBYK; manufactured by BYK-Chemie GmbH, solids concentration: 45.1% by mass) as a dispersant, 3.8 parts of a benzyl methacrylate/methacrylic acid copolymer (acid value: 134 mg KOH/g, Mw=30,000) as a dispersing resin, and 73.7 parts of propylene glycol monomethyl ether acetate as a solvent, was mixed and dispersed for 15 hours by a bead mill. Thus, Red pigment dispersion liquid P2 was prepared.

<Preparation of Blue Pigment Dispersion Liquid>
—Preparation of Blue pigment Dispersion Liquid P3—

A mixture liquid including 14 parts of a 100/25 (mass ratio) mixture of C.I. Pigment Blue 15:6 and C.I. Pigment Violet 23 as a pigment, 4.7 parts of BYK2001 (DISPERBYK; manufactured by BYK-Chemie GmbH, solids concentration: 45.1% by mass) as a dispersant, 3.5 parts of a benzyl methacrylate/methacrylic acid copolymer (acid value: 134 mg KOH/g, Mw=30,000) as a dispersing resin, and 77.8 parts of propylene glycol monomethyl ether acetate as a solvent, was mixed and dispersed for 15 hours by a bead mill. Thus, Blue pigment dispersion liquid P3 was prepared.

<Preparation of Green Coloring Photosensitive Composition (Coating Liquid) A-1>

Components were mixed and stirred to obtain the following composition, by using green pigment dispersion liquid P1. Thus, a coloring photosensitive composition A-1 was prepared.

TABLE 7

| <Composition> | |
|---|---|
| Green pigment dispersion liquid P1 | 83.3 parts |
| Alkali-soluble resin: P-1 | 2.05 parts |
| OXE-01 (manufactured by BASF Corp.; photopolymerization initiator) | 1.2 parts |
| Monomer-1: KAYARAD DPHA (manufactured by Nippon Kayaku Co., Ltd.) | 1.4 parts |
| Monomer-2: M-305 (manufactured by Toagosei Co., Ltd.) | 1.4 parts |
| p-Methoxyphenol | 0.001 parts |
| Propylene glycol monomethyl ether acetate [PGMEA (hereinafter, referred to similarly): solvent] | 7.4 parts |
| Surfactant (trade name: F-781, manufactured by DIC Corp.) in 0.2% PGMEA solution | 4.2 parts |

<Preparation of Red Coloring Photosensitive Composition (Coating Liquid) B-1>

Components were mixed and stirred to obtain the following composition, by using red pigment dispersion liquid P2. Thus, a coloring photosensitive composition B-1 was prepared.

TABLE 8

| <Composition> | |
|---|---|
| Red pigment dispersion liquid P2 | 59.6 parts |
| Alkali-soluble resin: P-1 | 1.2 parts |
| OXE-02 (manufactured by BASF Corp.; photopolymerization initiator) | 0.7 parts |
| Monomer-1: KAYARAD DPHA (manufactured by Nippon Kayaku Co., Ltd.) | 1.6 parts |
| Monomer-2: SR-494 (manufactured by Sartomer USA, LLC) | 1.6 parts |
| p-Methoxyphenol | 0.002 parts |
| Propylene glycol monomethyl ether acetate [PGMEA (hereinafter, referred to similarly): solvent] | 31 parts |
| Surfactant (trade name: F-781, manufactured by DIC Corp.) in 0.2% PGMEA solution | 4.2 parts |

<Preparation of Blue Coloring Photosensitive Composition (Coating Liquid) C-1>

Components were mixed and stirred to obtain the following composition, by using blue pigment dispersion liquid P3. Thus, a coloring photosensitive composition C-1 was prepared.

TABLE 9

| <Composition> | |
|---|---|
| Blue pigment dispersion liquid P3 | 50.6 parts |
| Alkali-soluble resin: P-1 | 2.1 parts |
| OXE-01 (manufactured by BASF Corp.; photopolymerization initiator) | 1.2 parts |
| Monomer-1: KAYARAD DPHA (manufactured by Nippon Kayaku Co., Ltd.) | 1.2 parts |
| Monomer-2: SR-494 (manufactured by Sartomer USA, LLC) | 3.5 parts |

TABLE 9-continued

| <Composition> | |
|---|---|
| p-Methoxyphenol | 0.002 parts |
| Propylene glycol monomethyl ether acetate [PGMEA (hereinafter, referred to similarly): solvent] | 36 parts |
| Surfactant (trade name: F-781, manufactured by DIC Corp.) in 0.2% PGMEA solution | 4.2 parts |

The green coloring photosensitive composition A-1 prepared as described above was applied on an 8-inch silicon wafer in which hexamethyldisilazane had been sprayed in advance and device formation had been completed, and thus a photocurable coating film was formed. The silicon wafer was subjected to a heating treatment (prebake) for 180 seconds using a hot plate at 100° C., so that the dry thickness of this coating film would be 1.0 µm. Subsequently, the coating film was irradiated with light having a wavelength of 365 nm at a dose of 150 mJ/cm² through a Bayer pattern mask which measured 1.0 µm on each of the four sides, by using an i-line stepper exposure apparatus FPA-3000i5+ (manufactured by Canon, Inc.). Thereafter, the silicon wafer on which the irradiated coating film was formed, was placed on a horizontal rotating table of a spin shower developing machine (Model DW-30; manufactured by Chemitronics Co., Ltd.), and paddle development was carried out for 180 seconds at 23° C. by using a 40% dilution of CD-2000 (manufactured by Fujifilm Electronic Materials, Inc.). Thus, a colored pattern was formed on the silicon wafer.

The silicon wafer having a colored pattern formed thereon was fixed to the horizontal rotating table by a vacuum chuck method, and while the silicon wafer was rotated at a speed of rotation of 50 rpm by using a rotating apparatus, a rinsing treatment was carried out by supplying pure water through a discharge nozzle in a shower form from above the center of rotation. Thereafter, the silicon wafer was spray dried.

Next, the silicon wafer was heated for 5 minutes on a hot plate at 200° C., and thus a color filter having a pattern formed thereon was obtained.

Furthermore, a color filter having an RGB pattern formed thereon was formed by repeating the same process as in the case of the green color filter, except that the red coloring photosensitive composition B-1 and the blue photosensitive composition C-1 were used, and the exposed patterns were exposed through an island-patterned mask which measured 1.0 µm on each of the four sides.

When a camera module was produced by using a device in which this color filter was formed, it was confirmed that the camera module had satisfactory spectral characteristics.

The resin P-1 used in the preparation of the coloring photosensitive compositions is presented below. In the resin P-1, the ratio of the repeating units is expressed in a molar ratio.

Resin P-1

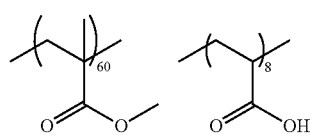

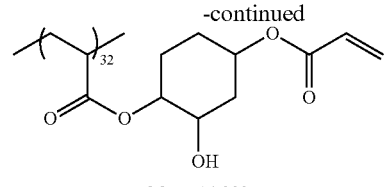

Mw = 14,000

This application claims priority under 35 U.S.C. §119 of Japanese Patent application JP 2011-176390, filed on Aug. 11, 2011, the entire contents of which are hereby incorporated by reference.

What is claimed is:

1. An azo compound represented by the following formula (1), a tautomer thereof, and a salt or hydrate of the azo compound or the tautomer:

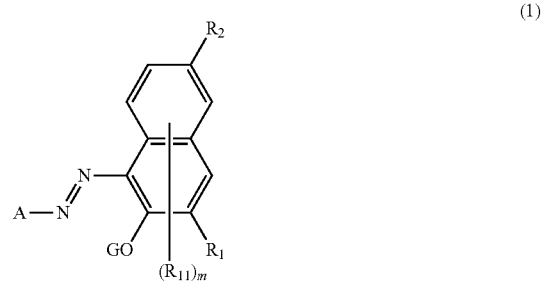

(1)

wherein in the formula (1),

A represents a heterocyclic group; G represents a hydrogen atom, an aliphatic group, an aromatic group, or a heterocyclic group; $R_1$ and $R_2$ each independently represent a group represented by the following formula (2) or (3):

(2)

(3)

wherein $R_3$ represents an amino group, an aliphatic oxy group, an aliphatic group, an aromatic group, an aromatic oxy group, or a heterocyclic group;

$X_1$ represents —O—, —S—, —NR— or —N=; R represents a hydrogen atom or an aliphatic group;

Y represents a divalent group which forms a heterocyclic ring together with the nitrogen atom and $X_1$;

$R_{11}$ represents a substituent, and when there are plural $R_{11}$'s, $R_{11}$'s may be identical with or different from each other;

* represents a bond that is bonded to the naphthalene ring in the formula (1); and m's each independently represent an integer of 0 to 4.

2. The azo compound, the tautomer thereof, and the salt or hydrate of the azo compound or the tautomer according to claim 1, wherein the compound represented by the formula (1) is represented by the following formula (4):

(4)
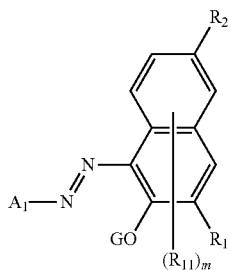
wherein in the formula (4),
$A_1$ represents a 5-membered or 6-membered aromatic heterocyclic group represented by any one of the following formulae (A-1) to (A-34);
G, $R_1$, $R_2$, $R_{11}$ and m have the same meanings as G, $R_1$, $R_2$, $R_{11}$ and m, respectively, defined in the formula (1);
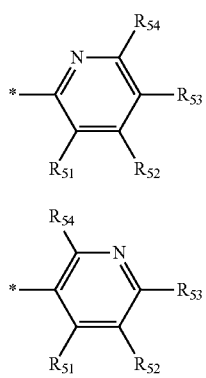
(A-1)
(A-2)
(A-3)
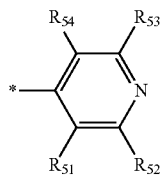
(A-4)
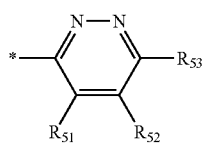
(A-5)
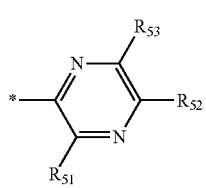
(A-6)
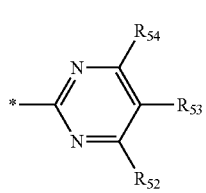
-continued
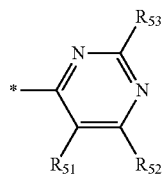
(A-7)
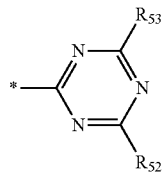
(A-8)
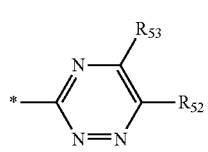
(A-9)
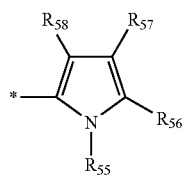
(A-10)
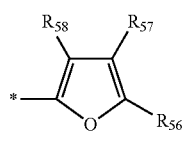
(A-11)
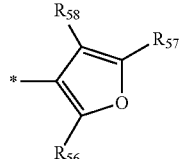
(A-12)
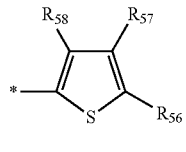
(A-13)
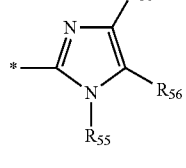
(A-14)
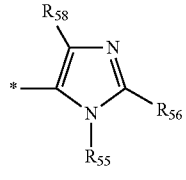
(A-15)

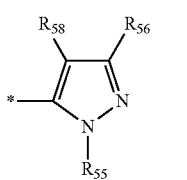 (A-16)

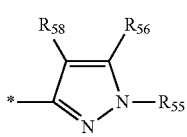 (A-17)

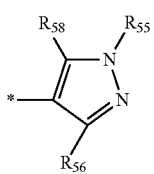 (A-18)

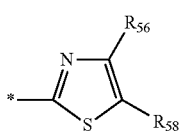 (A-19)

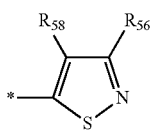 (A-20)

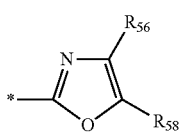 (A-21)

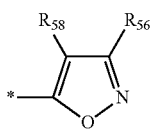 (A-22)

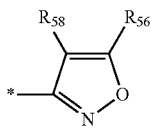 (A-23)

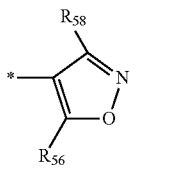 (A-24)

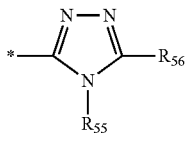 (A-25)

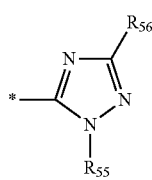 (A-26)

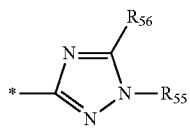 (A-27)

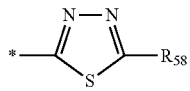 (A-28)

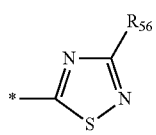 (A-29)

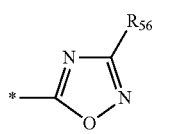 (A-30)

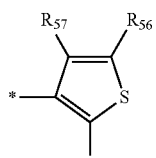 (A-31)

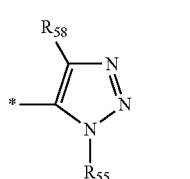 (A-32)

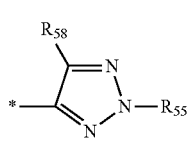 (A-33)

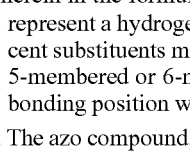 (A-34)

wherein in the formulae (A-1) to (A-34), $R_{51}$ to $R_{58}$ each represent a hydrogen atom, or a substituent, while adjacent substituents may be bonded to each other to form a 5-membered or 6-membered ring; and * represents the bonding position with the azo group of the formula (4).

3. The azo compound, the tautomer thereof, and the salt or hydrate of the azo compound or the tautomer according to claim 2, wherein in the azo compound represented by the formula (4), $A_1$ represents any one of the above formulae (A-14) to (A-16), (A-25) and (A-26).

4. The azo compound, the tautomer thereof, and the salt or hydrate of the azo compound or the tautomer according to claim 3, wherein the azo compound represented by the formula (1) is represented by the following formula (5):

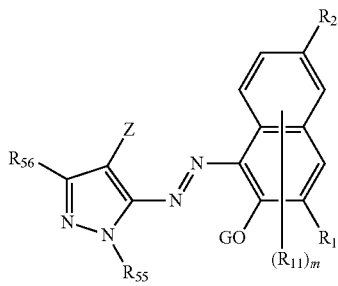

wherein in the formula (5), G, $R_1$, $R_2$, $R_{11}$, $R_{55}$, $R_{56}$ and m have the same meanings as G, $R_1$, $R_2$, $R_{11}$, $R_{55}$, $R_{56}$ and m, respectively, defined in the formula (4); and Z represents an electron-withdrawing group having a Hammett σp value of 0.2 or greater.

5. The azo compound, the tautomer thereof, and the salt or hydrate of the azo compound or the tautomer according to claim 2, wherein in the azo compound represented by the formula (4), $A_1$ represents any one of the formulae (A-17), (A-18), (A-20), (A-22) to (A-24), (A-27), (A-28), (A-31), and (A-32).

6. The azo compound, the tautomer thereof, and the salt or hydrate of the azo compound or the tautomer according to claim 5, wherein the azo compound represented by the formula (4) is represented by the following formula (6):

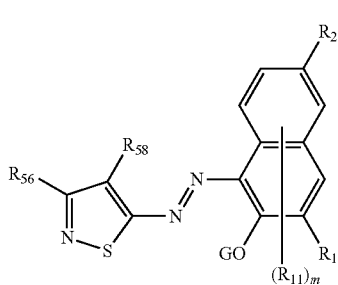

wherein in the formula (6), G, $R_1$, $R_2$, $R_{11}$, $R_{56}$, $R_{58}$ and m have the same meanings as G, $R_1$, $R_2$, $R_{11}$, $R_{56}$, $R_{58}$ and m, respectively, defined in the formula (4); and $R_{56}$ and $R_{58}$ may be bonded to each other to form a 5-membered or 6-membered ring.

7. The azo compound, the tautomer thereof, and the salt or hydrate of the azo compound or the tautomer according to claim 1, wherein in the formula (2), $R_3$ represents an amino group or an aliphatic oxy group; in the formula (3), $X_1$ represents —S— or —NR—; R represents a hydrogen atom or an aliphatic group; and in the formula (1), G represents a hydrogen atom.

8. The azo compound, the tautomer thereof, and the salt or hydrate of the azo compound or the tautomer according to claim 1, wherein in the formula (1), $R_1$ and $R_2$ each represent a group represented by the formula (3).

9. An azo pigment using the azo compound, the tautomer thereof, and the salt or hydrate of the azo compound or the tautomer according to claim 1.

10. A pigment dispersion containing at least one kind of the azo pigment according to claim 9.

11. A coloring composition comprising at least one kind of the azo pigment according to claim 9.

12. A coloring composition for color filters, using the coloring composition according to claim 11 for a color filter application.

13. The coloring composition for color filters according to claim 12, further comprising a polymerizable compound and a solvent.

14. The coloring composition for color filters according to claim 13, wherein the polymerizable compound is a photosensitive compound.

15. The coloring composition for color filters according to claim 13, wherein the solvent is a fatty acid ester.

16. The coloring composition for color filters according to claim 12, further comprising one or more dispersants selected from a surfactant, a silicone-based additive, a pigment-based additive, a silane-based coupling agent, and a titanium-based coupling agent.

17. A color filter formed by using the coloring composition for color filters according to claim 12.

18. The color filter according to claim 17, formed by a photolithographic method or an inkjet method.

19. A method for preparing the coloring composition for color filters according to claim 12, the method comprising:
  dispersing one or more dispersants selected from the group consisting of a surfactant, a silicone-based additive, a pigment-based additive, a silane coupling agent and a titanium coupling agent, and an azo compound represented by the formula (1), a tautomer, a salt or hydrate of the azo compound or the tautomer, in a portion of a solvent to obtain a pigment dispersion; and
  mixing the pigment dispersion with a polymerizable compound and the rest of the solvent.

20. An ink for inkjet recording using the pigment dispersion according to claim 10.

21. A printing ink comprising the azo compound, the tautomer thereof, and the salt or hydrate of the azo compound or the tautomer according to claim 1.

22. A coating material comprising the azo compound, the tautomer thereof, and the salt or hydrate of the azo compound or the tautomer according to claim 1.

23. A dye comprising the azo compound, the tautomer thereof, and the salt or hydrate of the azo compound or the tautomer according to claim 1.

24. A resist ink comprising the azo compound, the tautomer thereof, and the salt or hydrate of the azo compound or the tautomer according to claim 1.

* * * * *